United States Patent
Seng et al.

(10) Patent No.: US 12,365,918 B2
(45) Date of Patent: Jul. 22, 2025

(54) ENGINEERED REGULATORY T CELLS

(71) Applicants: The Children's Mercy Hospital, Kansas City, MO (US); The University of Kansas, Lawrence, KS (US)

(72) Inventors: Amara Seng, Kansas City, KS (US); Ryan Fischer, Shawnee, KS (US); Thomas Yankee, Overland Park, KS (US); Mary Markiewicz, Leawood, KS (US); John Szarejko, Liberty, MO (US)

(73) Assignees: The Children's Mercy Hospital, Kansas City, MO (US); The University of Kansas, Lawrence, KS (US)

( * ) Notice: Subject to any disclaimer, the term of this patent is extended or adjusted under 35 U.S.C. 154(b) by 967 days.

(21) Appl. No.: 17/488,702

(22) Filed: Sep. 29, 2021

(65) Prior Publication Data
US 2022/0008474 A1    Jan. 13, 2022

Related U.S. Application Data

(62) Division of application No. 16/924,950, filed on Jul. 9, 2020, now Pat. No. 11,160,832.

(60) Provisional application No. 62/871,946, filed on Jul. 9, 2019.

(51) Int. Cl.
| | |
|---|---|
| C12N 15/86 | (2006.01) |
| A61K 40/10 | (2025.01) |
| A61K 40/11 | (2025.01) |
| A61K 40/22 | (2025.01) |
| A61K 40/41 | (2025.01) |
| C12N 5/0783 | (2010.01) |

(52) U.S. Cl.
CPC .............. *C12N 15/86* (2013.01); *A61K 40/10* (2025.01); *A61K 40/11* (2025.01); *A61K 40/22* (2025.01); *A61K 40/418* (2025.01); *C12N 5/0637* (2013.01); *A61K 2239/31* (2023.05); *A61K 2239/38* (2023.05); *C12N 2506/11* (2013.01); *C12N 2510/00* (2013.01); *C12N 2740/10043* (2013.01)

(58) Field of Classification Search
None
See application file for complete search history.

(56) References Cited

U.S. PATENT DOCUMENTS

| | | |
|---|---|---|
| 9,421,230 B2 | 8/2016 | Honda et al. |
| 9,481,866 B2 | 11/2016 | Kim et al. |
| 9,801,911 B2 | 10/2017 | Tang et al. |
| 2003/0147865 A1 | 8/2003 | Salomon et al. |
| 2013/0071414 A1 | 3/2013 | Dotti et al. |
| 2013/0157363 A1 | 6/2013 | Kim et al. |
| 2013/0302276 A1 | 11/2013 | Cantor et al. |
| 2016/0151465 A1 | 6/2016 | Slawin et al. |
| 2016/0194605 A1 | 7/2016 | Scott et al. |
| 2019/0322983 A1 | 10/2019 | Rudensky et al. |
| 2020/0283530 A1 | 9/2020 | Zhou et al. |

FOREIGN PATENT DOCUMENTS

| | | |
|---|---|---|
| EP | 2532740 | 12/2012 |
| ES | 2675317 | 7/2018 |
| WO | 2016179288 | 11/2016 |
| WO | 2016196912 | 12/2016 |
| WO | 2017218850 | 12/2017 |
| WO | 2018136948 | 7/2018 |
| WO | 2018152306 | 8/2018 |

OTHER PUBLICATIONS

Fransson, M., Piras, E., Burman, J. et al. CAR/FoxP3-engineered T regulatory cells target the CNS and suppress EAE upon intranasal delivery. J Neuroinflammation 9, 112 (2012). https://doi.org/10.1186/1742-2094-9-112 (Year: 2012).*
Hye-Jung Kim et al. ,Stable inhibitory activity of regulatory T cells requires the transcription factor Helios.Science350,334-339(2015). DOI:10.1126/science.aad0616 (Year: 2015).*
Hori, et al, "Control of Regulatory T Cell Development by the Transcription Factor Foxp3", Science, Feb. 14, 2003, vol. 299, pp. 1057-1061.
Caruso, et al., "Flow Cytometric Analysis of Activation Markers on Stimulated T Cells and Their Correlation With Cell Proliferation", Cytometry, 1997, vol. 27, pp. 71-76.
Toh, et al., "Thymus and Autoimmunity: Production of CD25+ CD4+ Naturally Anergic and Suppressive T Cells as a Key Function of the Thymus in Maintaining Immunologic Self-Tolerance", J of Immu., Nov. 9, 1998, pp. 5317-5326.
Cao, et al., "Engineered regulatory T cells prevent graft-versus-host disease while sparing the graft-versus-leukemia effect after bone marrow transplantation", Leukemia Research, 2010, vol. 34, pp. 1374-1382.
Hill, et al., "Foxp3 Transcription-Factor-Dependent and -Independent Regulation of the Regulatory T Cell Transcriptional Signature", Immunity, Nov. 2007, vol. 27, pp. 786-800.
Fu, et al., "A multiple redundant genetic switch locks in the transcriptional signature of T regulatory cells", Nat Immunol., Oct. 2012, vol. 13, issue 10, p. 972-980.
Allan, et al., "Generation of Potent and Stable Human CD4+ T Regulatory Cells by Activation-independent Expression of FOXP3", Molecular Therapy, Jan. 2008, vol. 16, issue 1, pp. 194-202.

(Continued)

*Primary Examiner* — Tracy Vivlemore
*Assistant Examiner* — Catherine L McCormick
(74) *Attorney, Agent, or Firm* — Hovey Williams LLP; Crissa A. Cook

(57) ABSTRACT

Cell therapy compositions comprising engineered human regulatory T cells (eTregs) characterized by ectopic overexpression of FOXP3 and Helios protein, produced via introduction of separate nucleic acid constructs respectively encoding FOXP3 and Helios (FOXP3+Helios+ eTregs). Cell therapy compositions comprising mixed populations of CD4+ and CD8+ Treg cells each with ectopic overexpression of FOXP3 and Helios. Methods of making and use the same for therapies involving inflammation and/or a disorder of the immune system.

16 Claims, 28 Drawing Sheets
Specification includes a Sequence Listing.

(56) References Cited

OTHER PUBLICATIONS

Roncador, et al., "Analysis of FOXP3 protein expression in human CD4+CD25+ regulatory T cells at the single-cell level", Eur. J. Immunol., 2005, vol. 35, pp. 1681-1691.
Seng, et al., "Mesenchymal stromal cell infusions for acute graft-versushost disease: Rationale, data, and unanswered questions", Adv Cell Gene Ther., 2018, vol. 1 (15 pages).
Seng, et al., "The Role of the Ikaros Family of Transcription Factors in Regulatory T cell Development and Function",J Clin Cell Immunol, 2017, vol. 8, issue 2 (4 pages).
Montel-Hagen, et al., "Organoid-Induced Differentiation of Conventional T Cells from Human Pluripotent Stem Cells", Cell Stem Cell, 2019, vol. 24, pp. 376-389.
Khaitan, et al., "FOXP3+Helios+ regulatory T cells, immune activation and advancing disease in HIV infected children", J Acquir Immune Defic Syndr. Aug. 15, 2016; 72(5): 474-484 (18 pages).
Yarel, "CD4+ CD8+ Double Positive (DP) T Cells in Health and Disease", Autoimmun Rev. Mar. 2004;3(3):215-20 (abstract attached).
Churlaud, et al., "Human and mouse CD8+CD25+FOXP3+ regulatory T cells at steady state and during interleukin-2 therapy", Front. Immunol., Apr. 15, 2015 (10 pages).
Robb, et al., "Identification and expansion of highly suppressive CD8+FoxP3+ regulatory T cells after experimental allogeneic bone marrow transplantation", Blood, Jun. 14, 2012;119(24):5898-908.
Thornton, et al., "Helios expression defines two distinct populations of Foxp3+ regulatory T cells", J Immunol May 1, 2016, 196 (1 Supplement) (abstract attached).
Akimova, et al., "Helios Expression is a Marker of T Cell Activation and Proliferation", PLoS One, Aug. 2011, vol. 6, issue 8 (13 pages).
Elkord, et al., "Helios, and not FoxP3, is the marker of activated Tregs expressing GARP/LAP", Oncotarget. Aug. 21, 2015;6(24):20026-36.
Grzanka, et al., "FoxP3, Helios, and SATB1: Roles and relationships in regulatory T cells", Int Immunopharmacol. Jul. 2013;16(3):343-7.
Tran, "Helios is a Marker of Human Thymic-derived Foxp3+ Regulatory T Cells", J Allergy Clin Immunol, 2009, vol. 125, issue 2.
Khaja, et al., "Intratumoral FoxP3+Helios+ Regulatory T Cells Upregulating Immunosuppressive Molecules Are Expanded in Human Colorectal Cancer", Frontiers In Immun, May 2017, vol. 8 (11 pages).
Thornton, et al., "Helios: still behind the clouds", Immunology, 158, 2019, 161-170.
Sugimoto, et al., "Foxp3-dependent and -independent molecules specific for CD251CD41 natural regulatory T cells revealed by DNA microarray analysis", International Immunology, (18) (8), 2006, 1197-1209.
Getnet, et al., "A role for the transcription factor Helios in human CD4+CD25+ regulatory T cells", Mol Immunol., 47 (7-8), Apr. 2010, 1595-1600.
International Search Report and Written Opinion in corresponding PCT/US2020/041338, dated Jan. 15, 2021.
Takatori, et al., "Helios Enhances Treg Cell Function in Cooperation With FoxP3", Arthritis & Rheumatology, (67) (6), Jun. 2015, 1491-1502.
Office Action in corresponding U.S. Appl. No. 16/924,950, dated Dec. 7, 2020.
Office Action in corresponding U.S. Appl. No. 16/924,950, dated May 21, 2021.
Riviere, et al., "Effects of retroviral vector design on expression of human adenosine deaminase in murine bone marrow transplant recipients engrafted with genetically modified cells", Proc Natl Acad Sci USA, 1995, 92(15), pp. 6733-6737.
Fontenot, et al., "Foxp3 programs the development and function of CD4+CD25+ regulatory T cells", Nat Imm, 2003, 4(4), pp. 330-336.
Dotti, et al., "Design and Development of Therapies using Chimeric Antigen Receptor-Expressing T cells", Immunol Rev, 2014, 257(1), pp. 1-35.
Extended Search Report in co-pending European Patent Application Serial No. 20837311.8, dated Dec. 18, 2023.
Seng, et al., "Coexpression of FOXP3 and a Helios isoform enhances the effectiveness of human engineered regulatory T cells", Blood Advances, 2020,4(7), 1325-1339.

\* cited by examiner

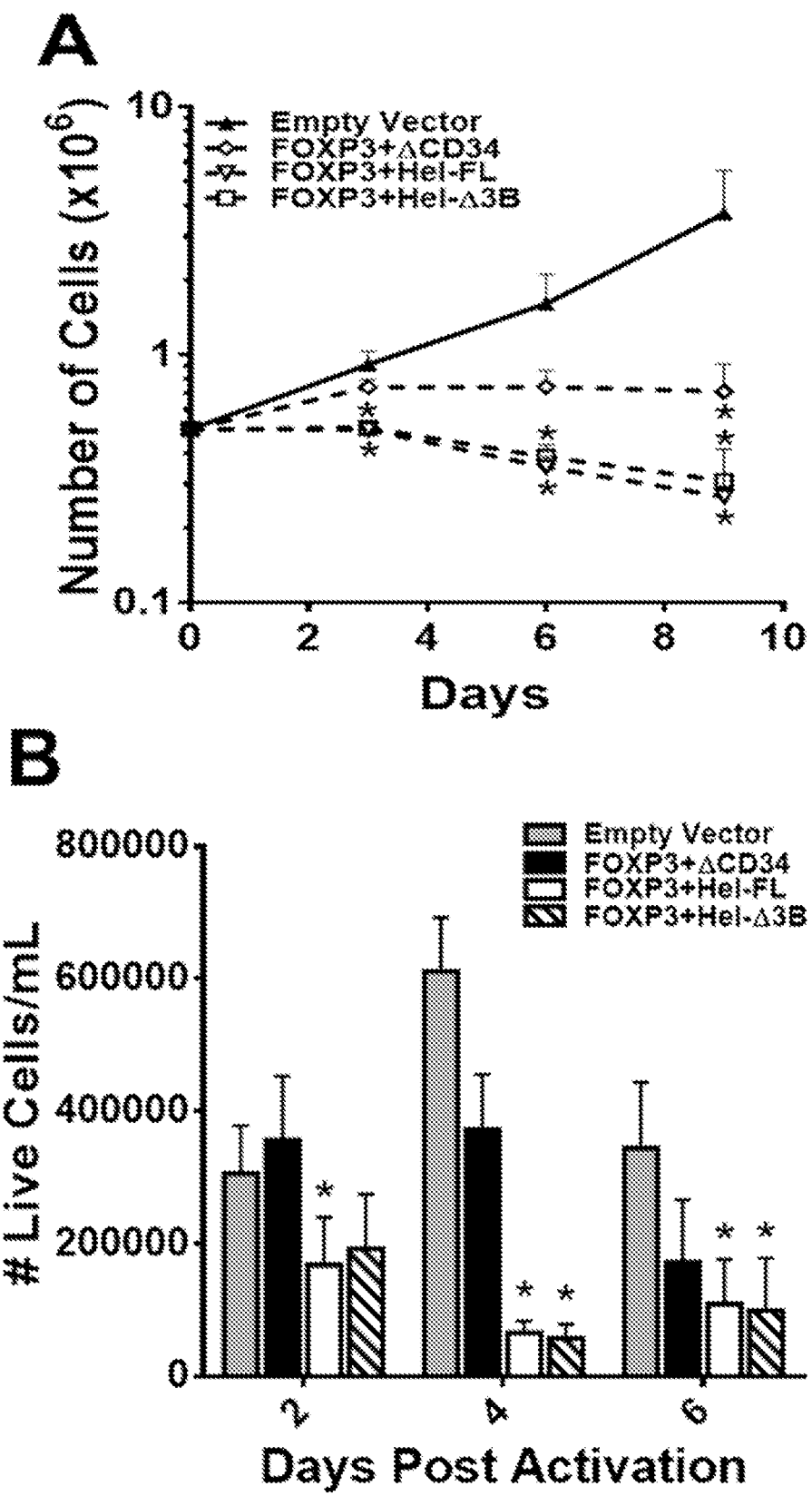
Fig. 7A-B

ENGINEERED REGULATORY T CELLS

CROSS-REFERENCE TO RELATED APPLICATIONS

The present application is a divisional of U.S. Nonprovisional patent application Ser. No. 16/924,950, filed Jul. 9, 2020, which claims the priority benefit of U.S. Provisional Patent Application Ser. No. 62/871,946, filed Jul. 9, 2019, entitled ENGINEERED REGULATORY T CELLS, each of which is incorporated by reference in its entirety herein.

SEQUENCE LISTING

The following application contains a Sequence Listing in computer readable format (CRF), which is submitted electronically via EFS-Web as an ASCII text file entitled "SequenceListing," created on Sep. 22, 2021, as 28,205 bytes. The content of the Sequence Listing CRF is hereby incorporated by reference in its entirety.

BACKGROUND OF THE INVENTION

Field of the Invention

The present invention relates to engineered regulatory T cells, therapeutic compositions, and methods related thereto.

Description of Related Art

Regulatory T cells (Tregs) mediate immune homeostasis through suppression of multiple aspects of immune activity including Tconv proliferation and cytokine secretion, expression of costimulatory molecules and antigen presentation by antigen presenting cells. Tregs can directly suppress proliferation and function of Tconvs following stimulation in vitro. The primary effect of Treg suppression is a reduction of Tconv IL-2 production, a key T cell growth factor as well as other pro-inflammatory cytokines such as IFN$\gamma$. In addition to affecting availability of cytokines, Tregs can also block Tconv activity through secretion of inhibitory cytokines. The primary Treg inhibitory cytokines that have been identified are TGF$\beta$, IL-10 and IL-35.

The immunosuppressive properties of Tregs have led to much research into utilization of Tregs as therapy for a variety of inflammatory diseases, such as graft-versus-host disease (GVHD). For example, allogeneic hematopoietic stem cell transplants (HSCT) have become a routine treatment for patients suffering from hematological malignancies such as leukemia. A significant complication of HSCT is GVHD, which affects approximately 50% of HSCT patients and is lethal in approximately half of the patients who suffer from GVHD. Symptoms of the disease include multi-organ failure, predominantly in the gut and the liver, and skin pathologies. GVHD occurs when donor-derived T cells transferred with the graft attack the recipient's own organs. GVHD can present as an acute rapid systemic inflammation and multi-organ dysfunction driven primarily by activated T cells, or as a chronic late-onset autoimmune-like disease mediated by both T cells and B cells. Thus, many HSCT patients receive grafts from partially matched donors and alloreactivity is kept under control with immunosuppressants. This immunosuppression increases the risk of infection and is ineffective in 30-50% of patients, resulting in GVHD. There is a critical need for improved GVHD therapies with minimal toxicity that promote long-term remission.

In cell therapy, Tregs are isolated from patients or a non-immunogenic, third-party source, such as umbilical cord blood (UCB), expanded ex vivo and transfused back into patients. Trials for multiple diseases such as GVHD, inflammatory bowel disease (IBD), and Type I diabetes have shown that Treg infusions are safe, but only moderately successful. A major challenge is expanding Tregs to numbers required for an effective treatment. Another difficulty of Treg therapy is isolating a pure population of Tregs. Tregs are commonly isolated by selecting CD4+ CD25+ T cells from the collected sample but these markers are also expressed by activated conventional T cells (Tconvs). This leads to potential contamination of Tregs with Tconvs that could exacerbate disease. Another limitation of Treg therapy is instability of the phenotype because Tregs can convert to Tconvs and lose immunosuppressive activity.

Given these challenges in utilizing expanded Tregs from blood for treatment of inflammatory disease, alternative approaches have been investigated. Because Tregs represent rare populations in vivo, attempts have been made to produce them in culture. For example, in vitro-induced Tregs (iTregs) can be generated by stimulating CD4+ T cells with various cytokines and drugs such as TGF$\beta$, rapamycin, and retinoic acid. However, current iTregs do not retain expression of the transcription factor protein forkhead box p3 (FOXP3) and do not effectively treat a humanized model of GVHD. Tregs from discarded human thymus (tTregs) have also been explored as a source of Tregs for therapy. Larger numbers of Tregs can be isolated from the thymus and remain stable under inflammatory conditions, unlike Tregs from peripheral blood. Furthermore, expanded tTregs have been shown to delay GVHD in a xenogeneic murine GVHD model more effectively than Tregs from peripheral blood. Another approach to overcome the limitations of Treg therapy is the generation of engineered Tregs (eTregs). eTregs are created by expressing known Treg genes via retroviral or lentiviral transduction of CD4+ T cells isolated from peripheral blood. Total CD4+ T cells make up about 4-20% of total leukocytes and can be isolated in greater numbers and expanded more quickly than naturally occurring Tregs.

Enforced FOXP3 expression in Tconvs is able to convey immunosuppressive function in both human and murine T cells. These FOXP3 expressing eTregs have been shown to reduce proliferation of responder cells and delay disease in murine colitis and GVHD models. However, when compared to endogenous Tregs in a murine arthritis model, FOXP3 eTregs were not as effective at reducing symptoms. Previous studies have demonstrated that ectopic FOXP3 expression in murine Tconv only partially conveys a Treg gene signature. Another characteristic of Tregs is the secretion of the immunosuppressive cytokine IL-10. Ectopic expression of IL-10 in Tconvs ameliorates disease in murine IBD models but not as efficiently as naturally occurring Tregs. Other Treg mechanisms that could be incorporated into eTregs are killing of immune cells via perforin or granzyme B and contact-dependent regulation of immune cells via molecules such as CTLA-4 or LAG-3.

The data indicate that Treg therapy has great potential, and the advantages of engineered Tregs are clear, but there remains much room for improvement in developing an effective cell therapy product.

SUMMARY OF THE INVENTION

The present invention is broadly concerned with cell therapy compositions comprising engineered human regulatory T cells (eTregs) characterized by ectopic overexpression of Ikaros transcription factor (preferably Helios) and FOXP3, mediated via introduction of IKZF2 and FOXP3 cDNA, generating FOXP3+Helios+ eTregs, and particularly mixed populations of CD4+ and CD8+ eTregs having these characteristics.

Also described herein are methods of prophylactically and/or therapeutically treating a disease or condition in which it is desirable to suppress the immune system or reduce pro-inflammatory responses in a subject. The methods generally comprise administering a composition comprising eTregs according to various embodiments described herein to a subject in need thereof.

Kits for carrying out embodiments of the invention are also described. The kit can include, among other things, nucleic acid constructs encoding for FOXP3 and/or Ikaros transcription factor (preferably Helios) and instructions for sequentially transducing total T cell populations to generate FOXP3+Helios+ eTregs according to the embodiments of the invention.

Also described herein are new methods for generating therapeutically effective amounts of eTregs for prophylactically and/or therapeutically treating a disease or condition in which it is desirable to suppress the immune system or reduce pro-inflammatory responses in a subject. The methods generally comprise providing a population of mononuclear cells, activating and expanding T cells from the mononuclear cells to yield a total T cell population, transducing the total T cell population with a first nucleic acid construct encoding for FOXP3 and with a second nucleic acid construct encoding for Ikaros transcription factor (preferably Helios) to yield FOXP3+ and Ikaros transcription factor+ (preferably Helios+) eTregs.

Uses for the eTreg compositions to prophylactically and/or therapeutically treat a disease or condition in which it is desirable to suppress the immune system or reduce pro-inflammatory responses in a subject are also described herein.

The described invention has a number of advantages over prior approaches for such cellular therapies. The eTregs maintain high levels of FOXP3 and Helios expression in vivo. Further, co-expression of Treg genes with specific transduction markers allows for purification of transduced cells and ensures homogeneity of the final product without a need for additional purification or isolation rounds. A separate (and preferably sequential) retroviral transduction protocol has been developed using total human T cell populations that enhances the efficacy of the technology in a number of ways. First, the generation of eTregs is not reliant on purifying a small number of cells from a patient sample. Endogenous human Tregs only represent approximately 2-5% of the peripheral lymphocyte population in healthy adults. Expanding this population to numbers needed for clinical efficacy requires several days or even weeks. Transduction of a patient's total T cell population circumvents this limitation and allows the more rapid development of adequate Treg numbers (and even storage of excess cells). Second, the dual transduction of the genes in a separate (and preferably sequential) way allows for dual expression of each gene without suppression of either product. This dual transduction has never been described for the generation of other human engineered Tregs. Third, transduction of total human T cells with both FOXP3 and Helios generates both CD4+ and CD8+ eTregs that are able to suppress T cell proliferation. Finally, the efficacy of this dually-transduced eTreg has been shown in a humanized model of graft-versus-host disease (GVHD) in a mouse. As such, this technology holds promise as a novel cell-based therapy for the treatment of GVHD and disordered inflammation in humans.

BRIEF DESCRIPTION OF THE DRAWINGS

FIG. 2A is an illustration of SFG retroviral vector containing genes of interest and respective transduction surface markers.

Figure 6A:
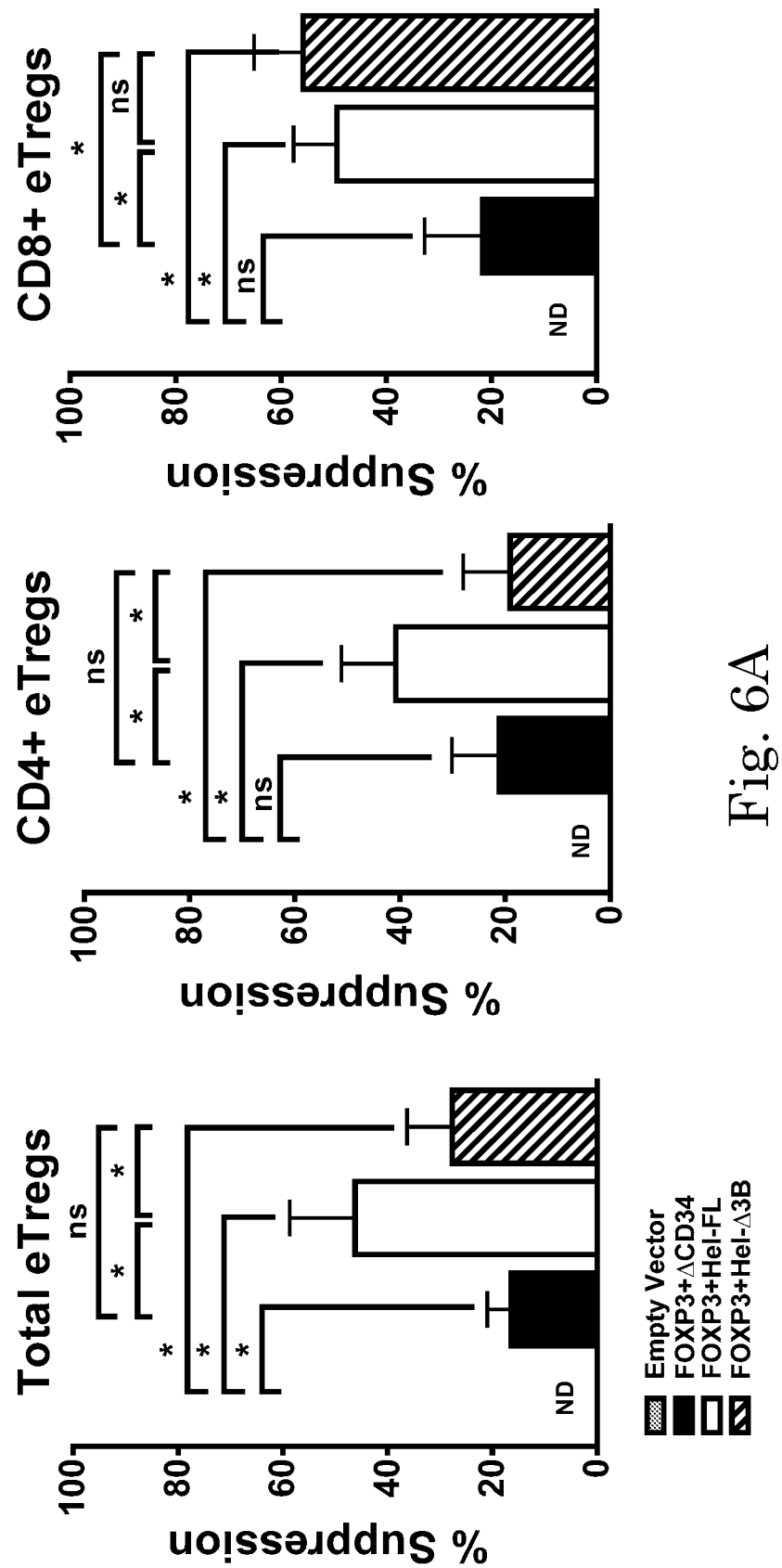

FIG. 6A shows graphs for percent suppression in eTreg populations. N=5-7 for each group with 4 different donors. Labeled autologous target Tconv cells were co-cultured with each eTreg cell strain or empty vector control cells with no stimulation or stimulation with anti-CD3 and anti-CD28 coated beads. CD4+ and CD8+ eTregs and empty vector cells were purified via antibody coated magnetic bead separation. Cells were plated at effector to target ratios of 1:1. After 96 hours, target cell proliferation was assayed via flow cytometry. Percent suppression is calculated by the following equation: [(percent responder proliferation alone)-(percent responder proliferation with transduced cells)]/(percent responder proliferation alone)×100. *=p<0.05 compared to empty vector control based on a one-tailed Wilcoxon test.

Figure 6B:
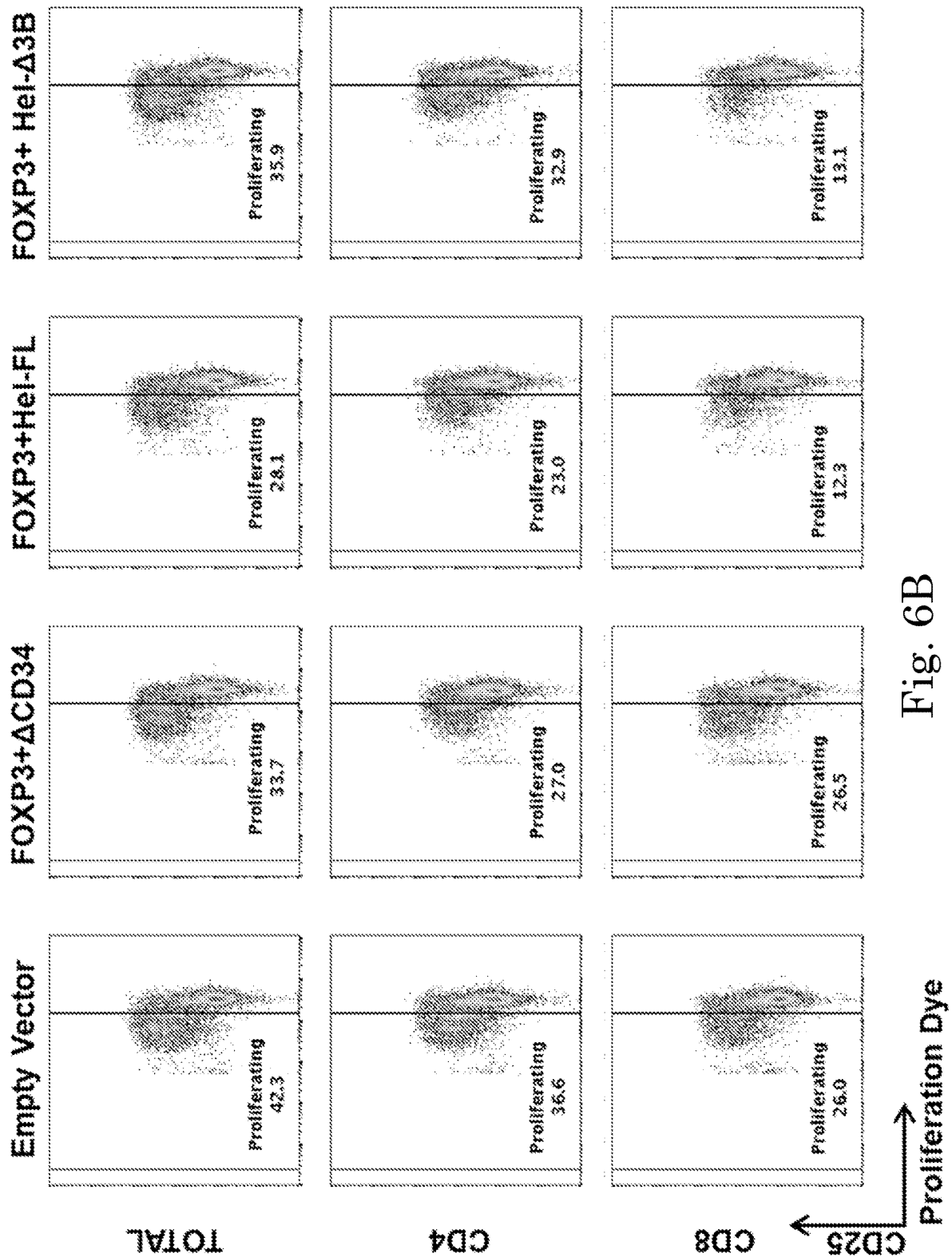

FIG. 6B shows representative dot plots of responder cell proliferation 96 hours after co-culture with eTregs or empty vector control (scale $10^0$ to $10^6$ for each x- and y-axis on each graph). As can be seen, FOXP3+Hel-FL and FOXP3+Hel-Δ3B differentially mediate CD4+ eTreg and CD8+ eTreg suppression.

FIG. 7A-B shows graphs of A) Cell counts of eTregs growing in IL-2 supplemented media over 9 days. n=4 for each group from 4 different donors. *=p<0.05 compared to empty vector control based on a one-tailed Mann-Whitney test for each time point. B) Numbers of live (Zombie Green and Annexin V negative) per mL eTregs following stimulation for 2, 4 and 6 days with anti-CD3 and anti-CD28 plate bound antibody. n=5-6 from 4-6 different donors for each group. * p<0.05 compared to empty vector control based on a one-tailed Mann-Whitney test.

Figure 7C:
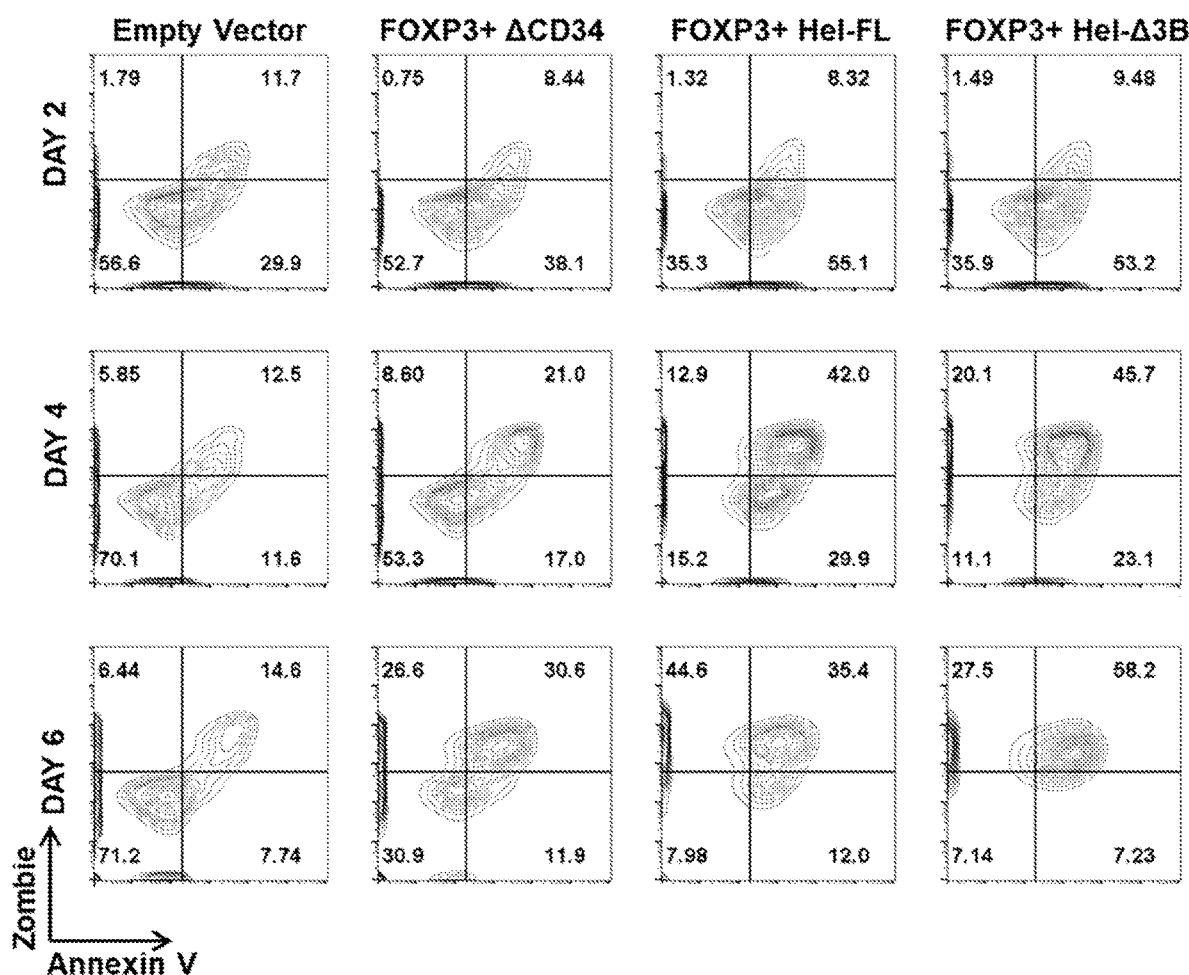

FIG. 7C shows representative contour plots of activation induced cell death in eTregs or empty vector control cells after stimulation for 2, 4 and 6 days (scale $10^0$ to $10^6$ for each x- and y-axis on each graph).

Figure 8A:
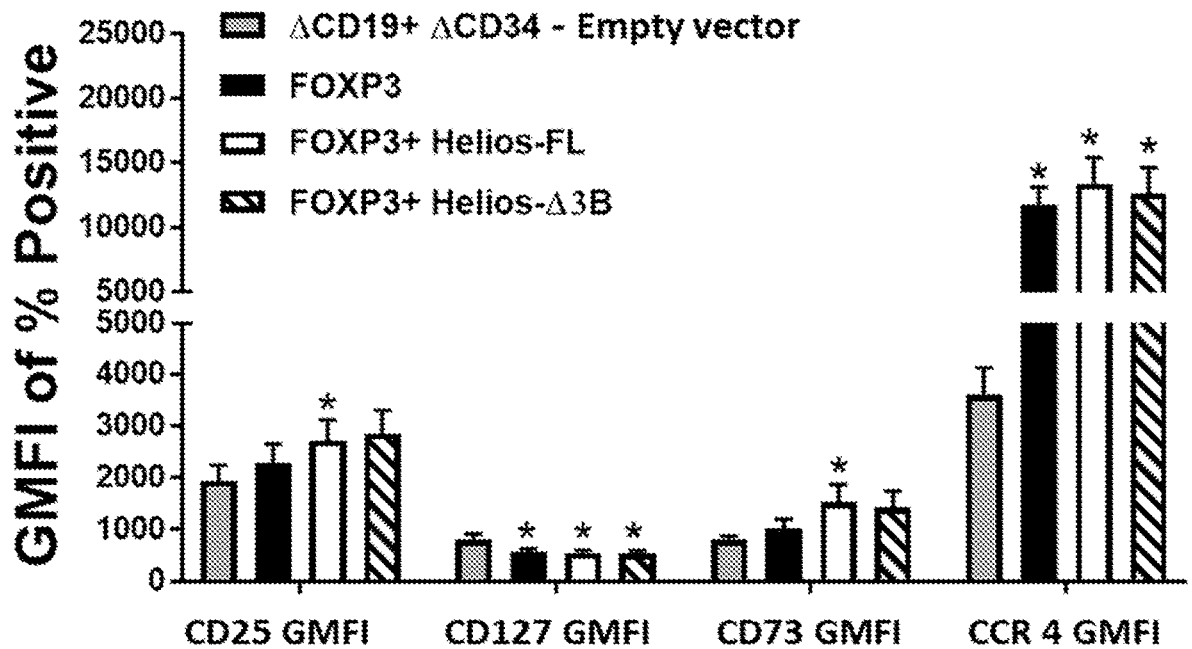
Figure 8A:
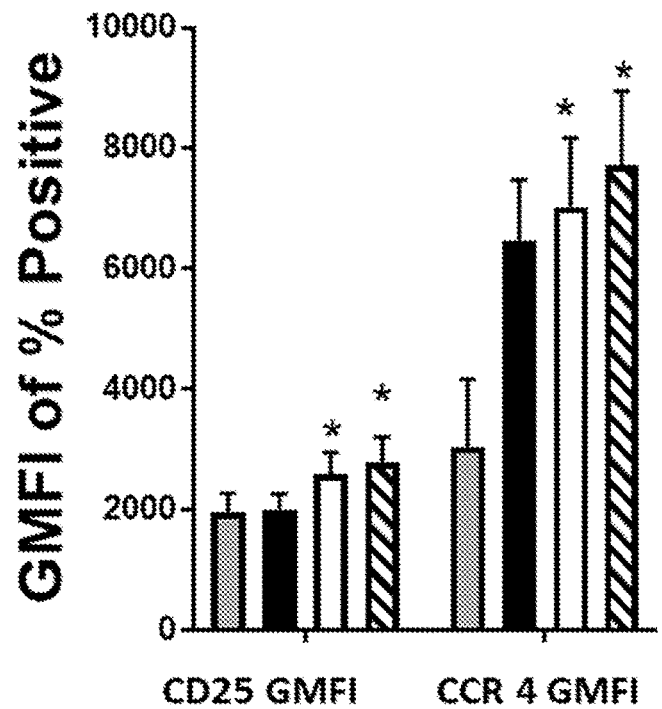

FIG. 8A shows graphs of the expression of different Treg markers by CD4+ eTregs and CD8+ eTregs. Marker expression was assessed via flow cytometry and plotted as GMFI of the population positive for the marker. n=3-7 and 5 different donors. * p<0.05 compared to empty vector control based on one-tailed Mann-Whitney test.

Figure 8B:
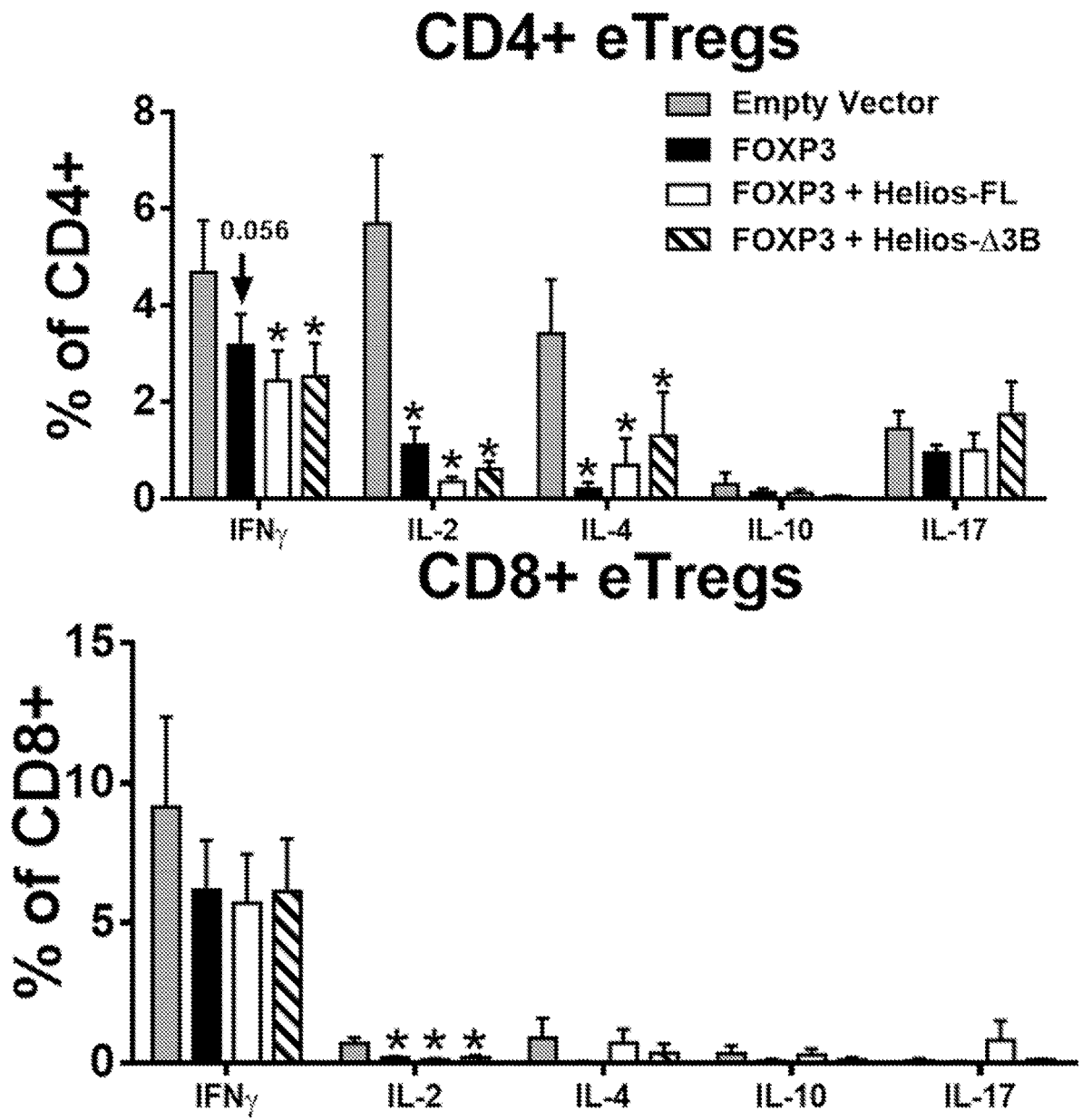

FIG. 8B shows graphs of the cytokine production profile for CD4+ eTregs and CD8+ eTregs. eTregs were stimulated for 6 hours with anti-CD3 and anti-CD28 plate bound antibody and Brefeldin A and Golgi Stop. Cells were assessed for cytokine production via intracellular cytokine staining and flow cytometry. Values normalized to empty vector control and n=4-9 with 4-6 different donors for each group. *p<0.05 compared to empty vector control based on one-tailed Mann-Whitney test.

Figure 9A:
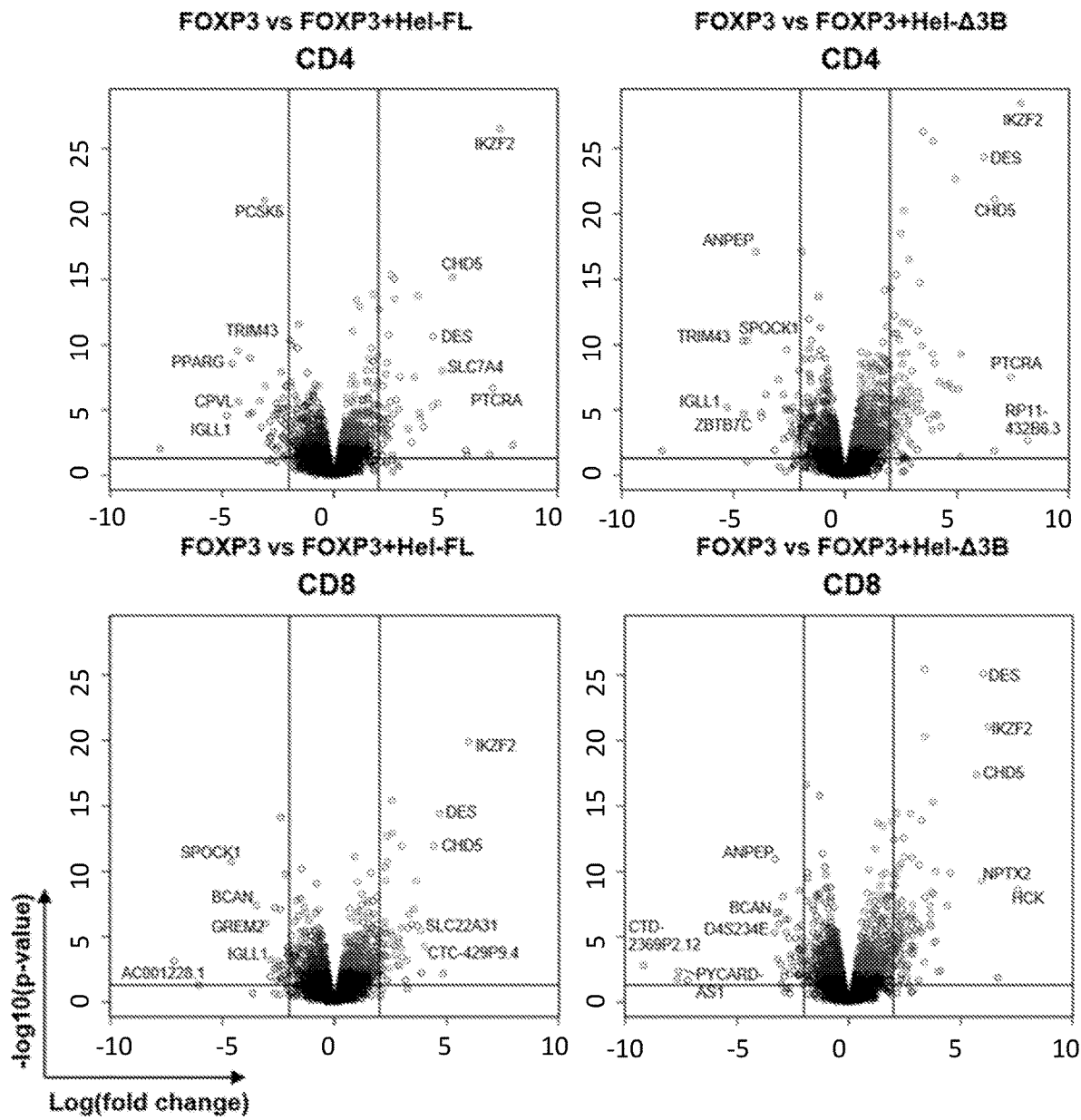

FIG. 9A Volcano plots depicting $-\log_{10}$p-value versus log Fold Change (FC) for impact on gene expression and pathway enrichment by Hel-FL or Hel-Δ3B co-expression with FOXP3 compared to FOXP3 alone. Within the volcano plots, genes were colored if they had a nominal, uncorrected p value less than 0.05. Blue color denotes down regulation while red color represents up regulation. The two vertical lines represent log FC=-2 and log FC=2. The horizontal line represents $-\log 10(0.05)$. All comparisons in this figure use FOXP3 eTregs as the baseline for comparison of CD4+ or CD8+ eTregs as indicated.

Figure 9B:
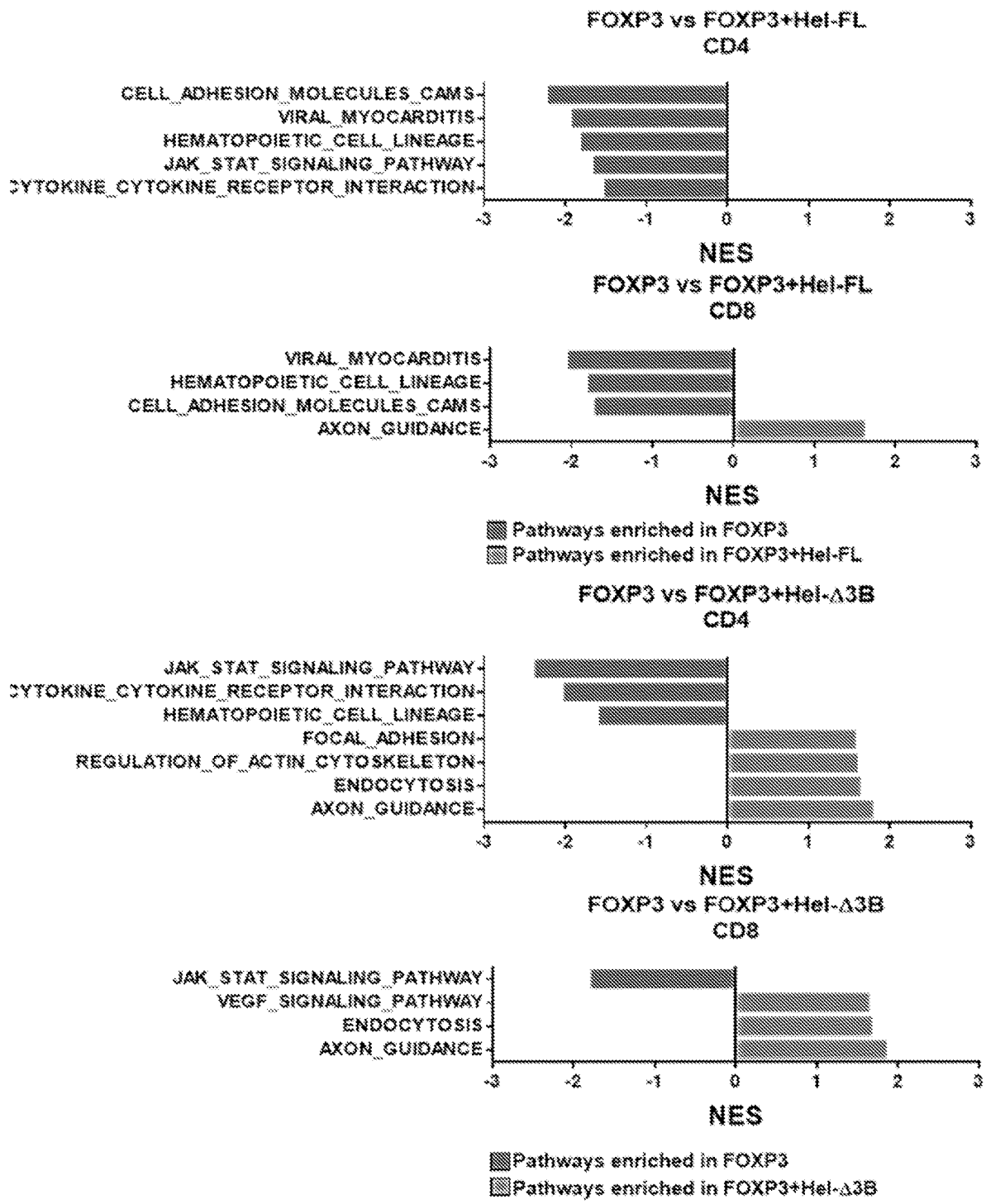

FIG. 9B provides a summary of normalized enrichment scores (NES) of KEGG pathways with p<0.05 that were enriched in the comparison of two eTreg cell strains indicated following gene set enrichment analysis (GSEA). Blue bars are pathways enriched in the baseline eTregs and red bars are pathways enriched in eTregs being compared.

Figure 10A:
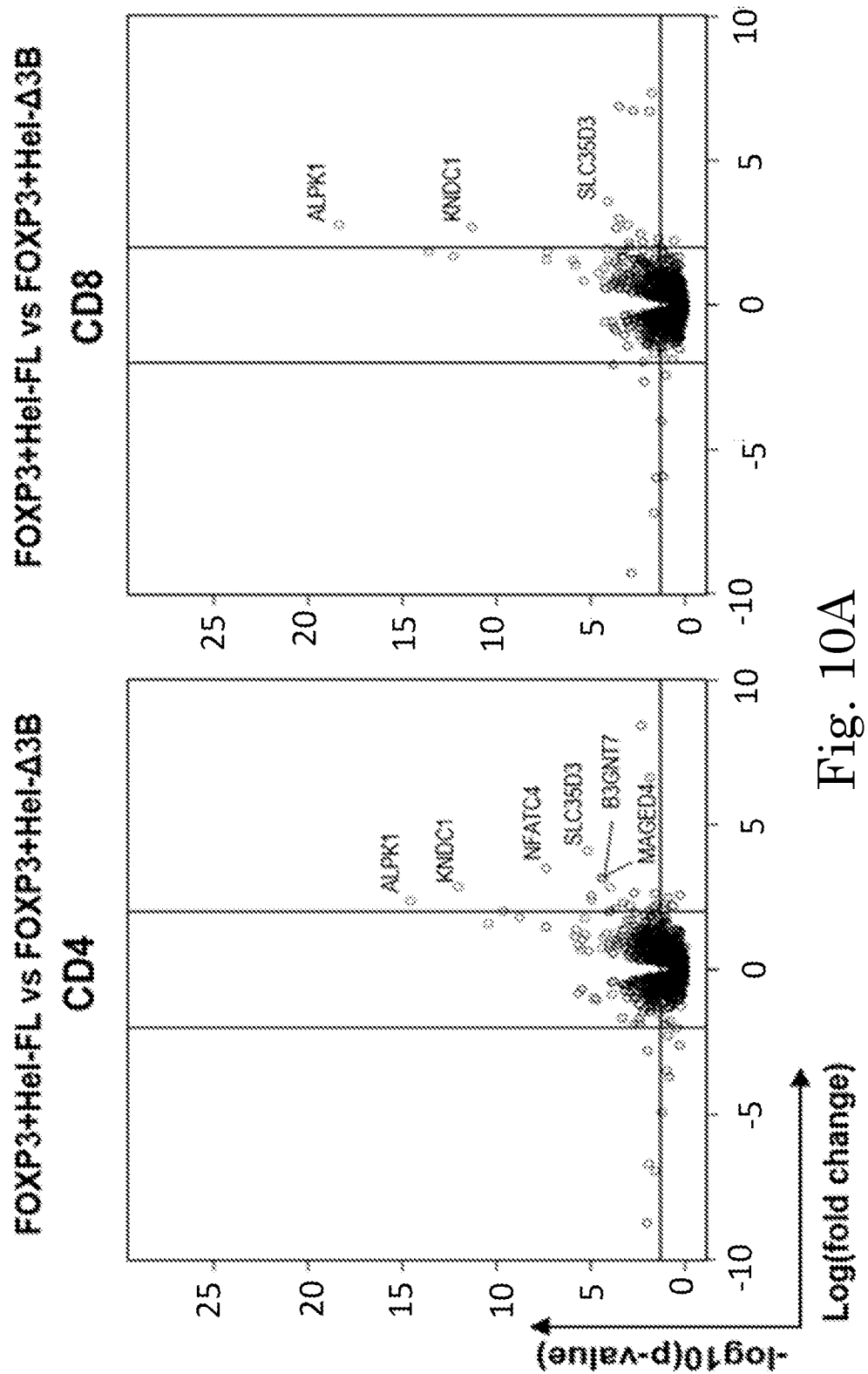

FIG. 10A shows volcano plots depicting $-\log_{10}$p-value versus log Fold Change (FC) for impact of FOXP3+Hel-Δ3B on gene expression and pathway enrichment in CD4+ and CD8+ eTregs compared to FOXP3+Hel-FL. Within the volcano plots, genes were colored if they had a nominal, uncorrected p value less than 0.05. Blue color denotes down regulation while red color represents up regulation. The two vertical lines represent log FC=-2 and log FC=2. The horizontal line represents $-\log 10(0.05)$. All comparisons in this figure use FOXP3+Hel-FL eTregs as the baseline for comparison, either CD4+ or CD8+ as indicated.

FIG. 10 B shows the summary of normalized enrichment scores (NES) of KEGG pathways with p<0.05 that were enriched in comparisons of two eTreg cell strains following GSEA. Blue bars are pathways enriched in the baseline eTregs and red bars are pathways enriched in eTregs being compared.

Figure 11A:
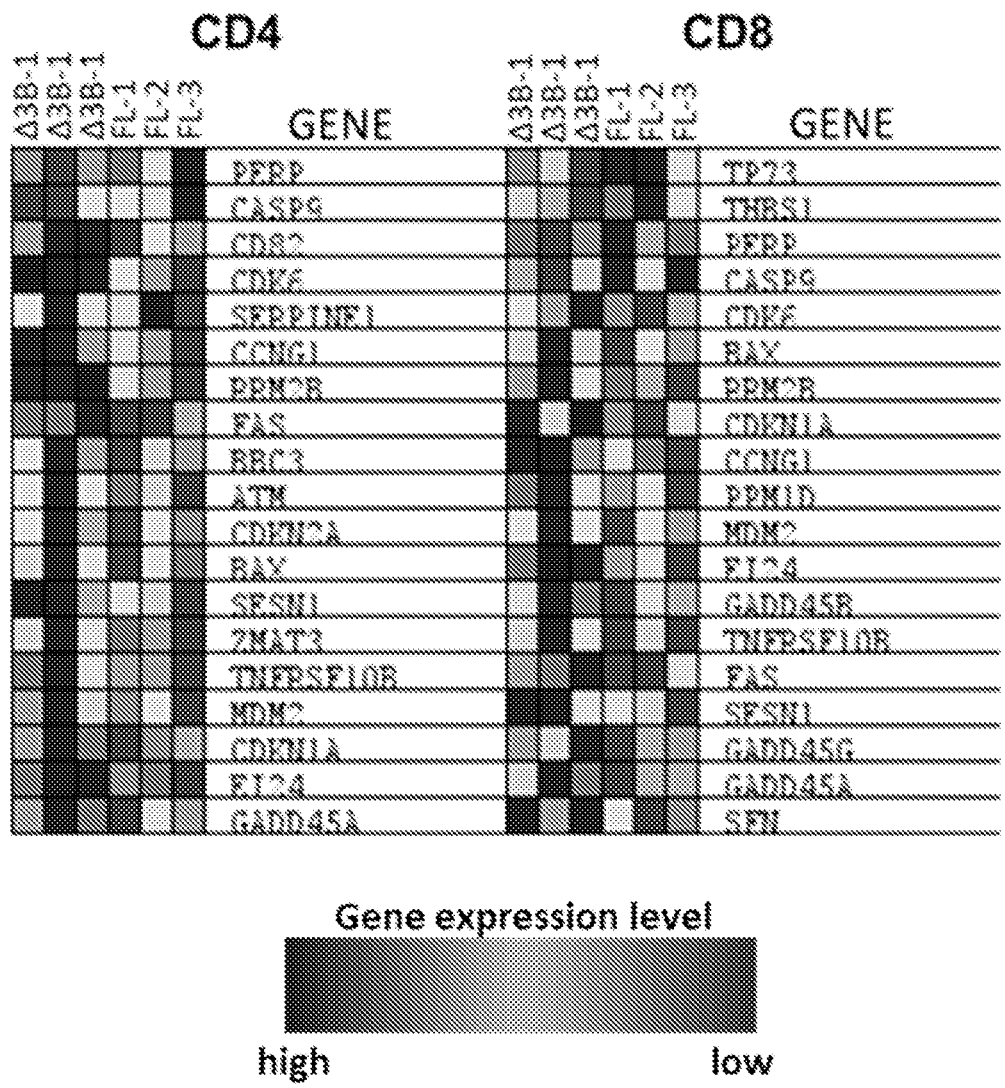

FIG. 11A is a heatmap of genes altered in p53 signaling enriched in CD4+ and CD8+ eTregs in each of the three donors for the FOXP3+Hel-FL (FL1-FL3) vs FOXP3+Hel-Δ3B (Δ3B1-Δ3B1) comparison.

Figure 11B:
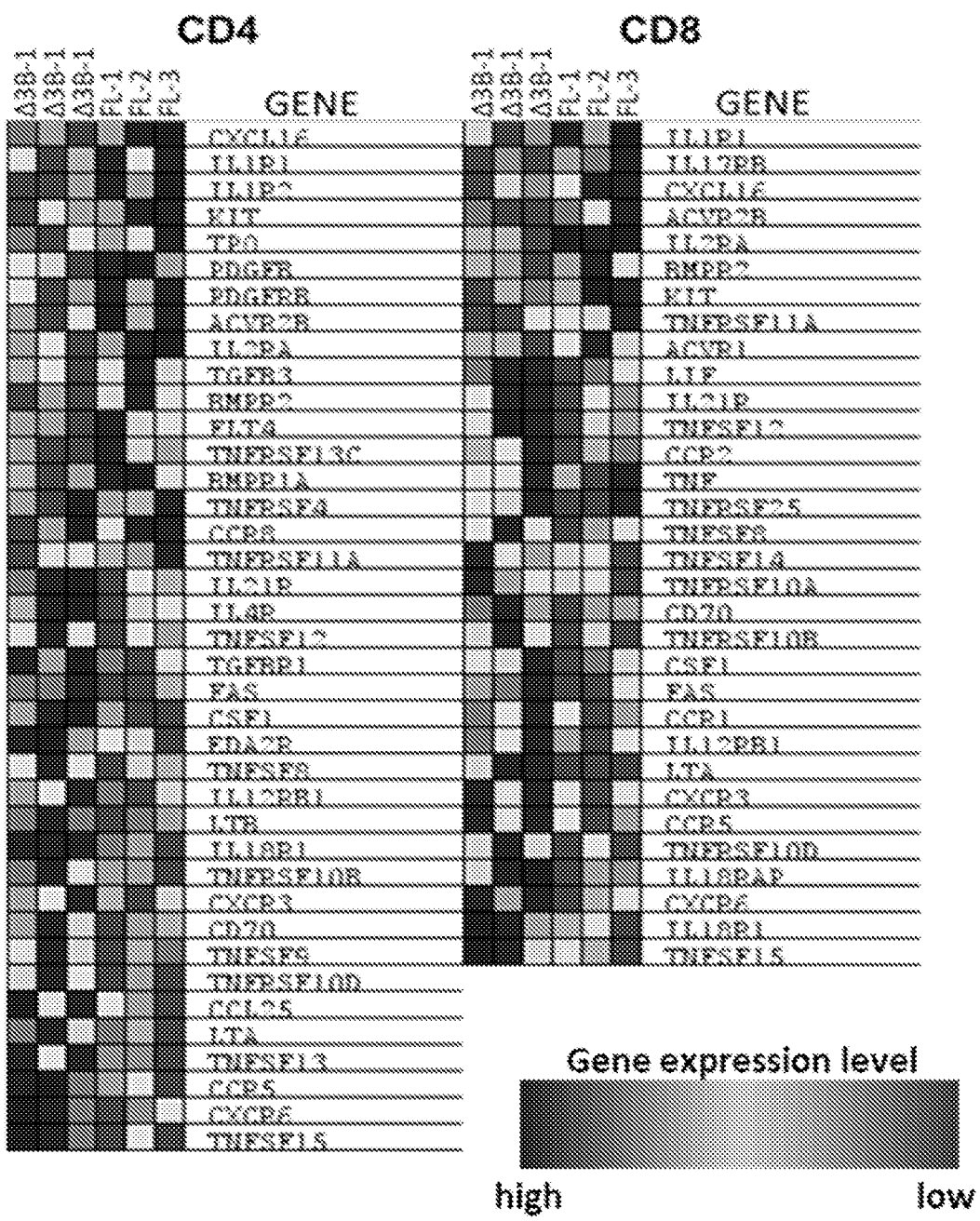

FIG. 11B is a heatmap of genes altered in cytokine-cytokine receptor interaction enriched in CD4+ and CD8+ eTregs in each of the three donors for the FOXP3+Hel-FL (FL1-FL3) vs FOXP3+Hel-Δ3B (Δ3B1-Δ3B1) comparison.

Figure 11C:
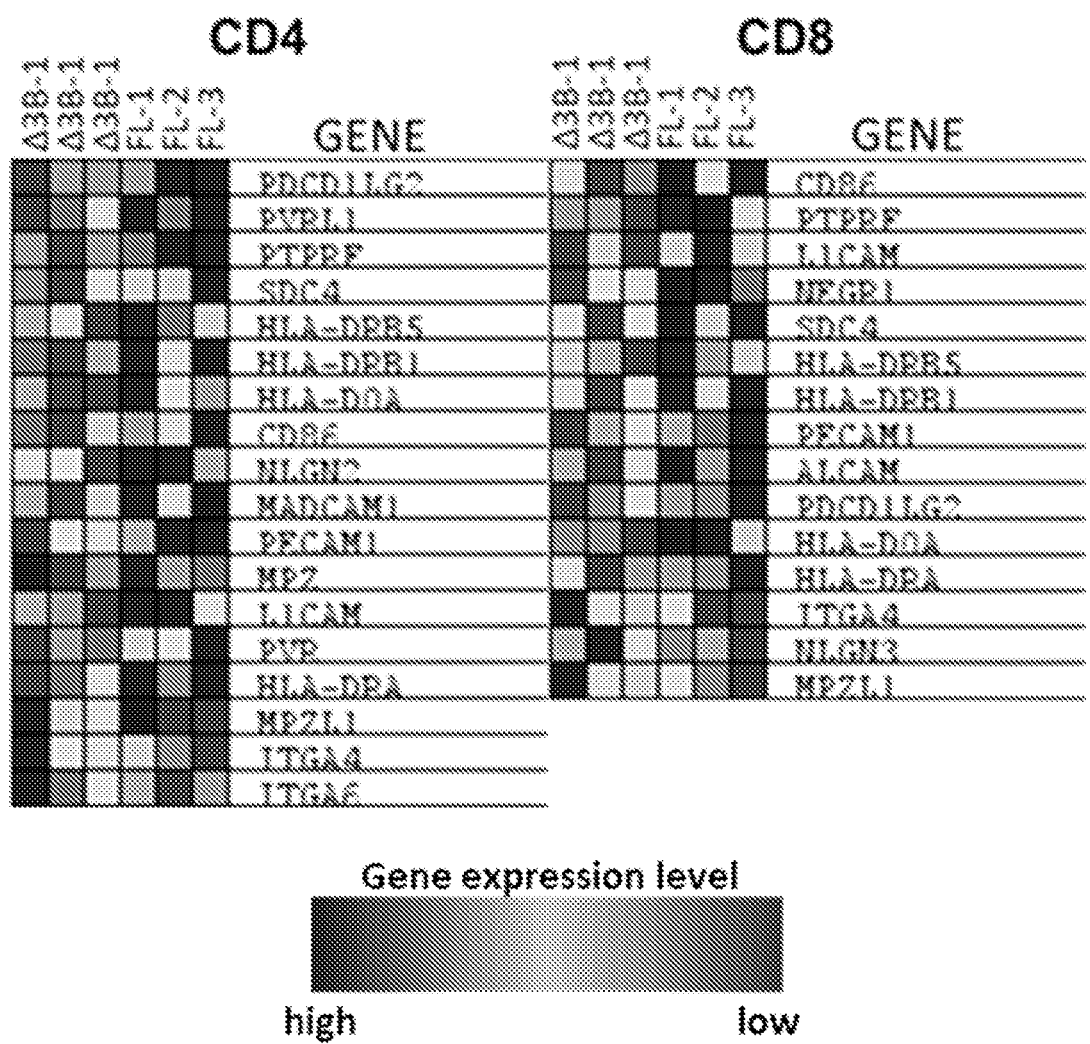

FIG. 11C is a heatmap of genes altered in cell adhesion molecules CAMs enriched in CD4+ and CD8+ eTregs in each of the three donors for the FOXP3+Hel-FL (FL1-FL3) vs FOXP3+Hel-Δ3B (Δ3B1-Δ3B1) comparison.

Figure 12A:
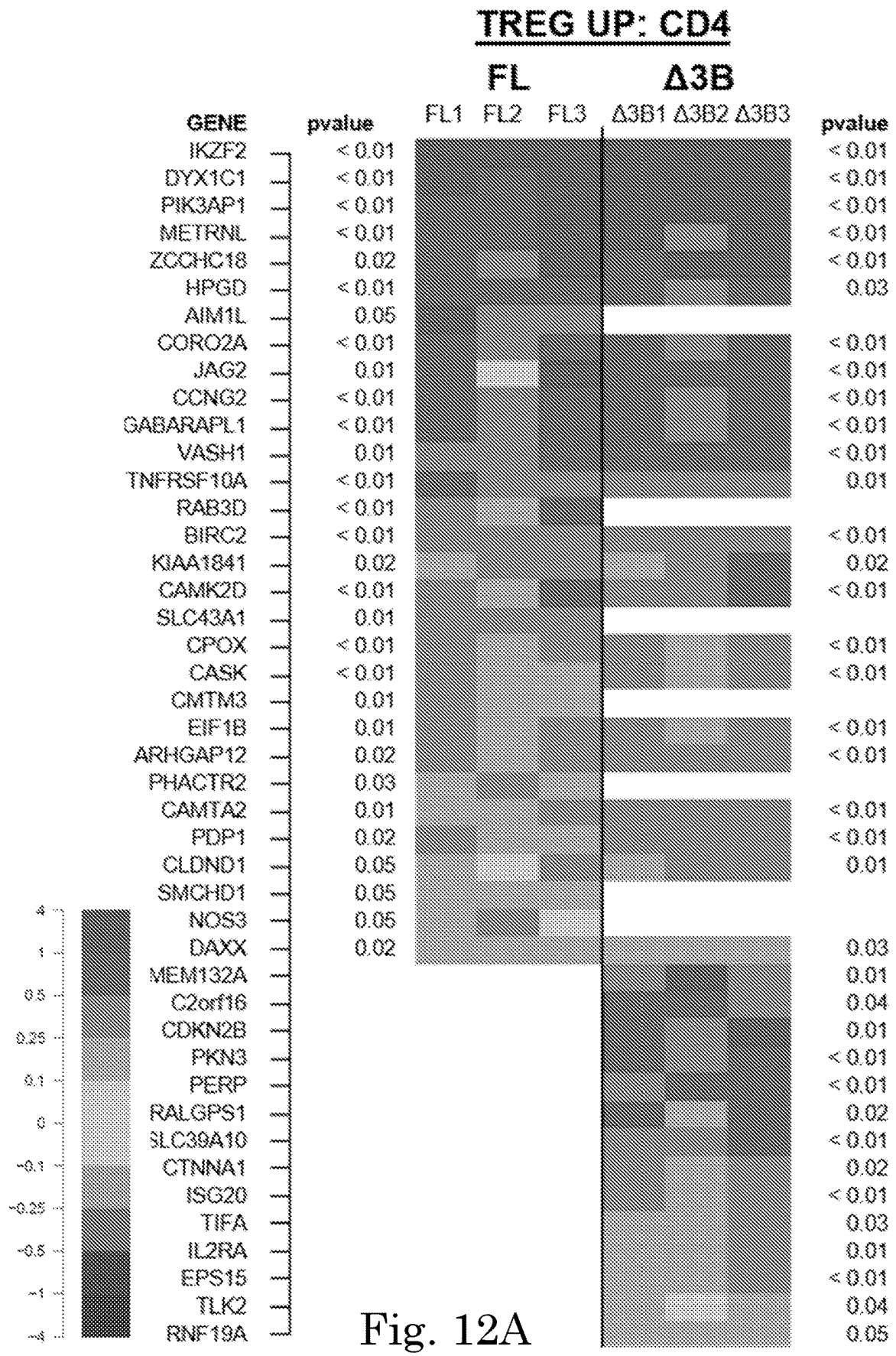

FIG. 12A is a heatmap comparing expression of Treg signature genes that are upregulated in CD4+ eTregs (TREG UP) compared to Tconv, showing differential expression of genes in each of the three donors for FOXP3 vs FOXP3+Hel-FL (FL, donors FL1-FL3) and FOXP3 vs FOXP3+Hel-Δ3B (Δ3B, donors d3b1-d3b3). For each cell in the heatmap, the difference of cpm values between two strains of cell for one subject was calculated and divided by average cpm value of that gene in all three subjects.

Figure 12B:
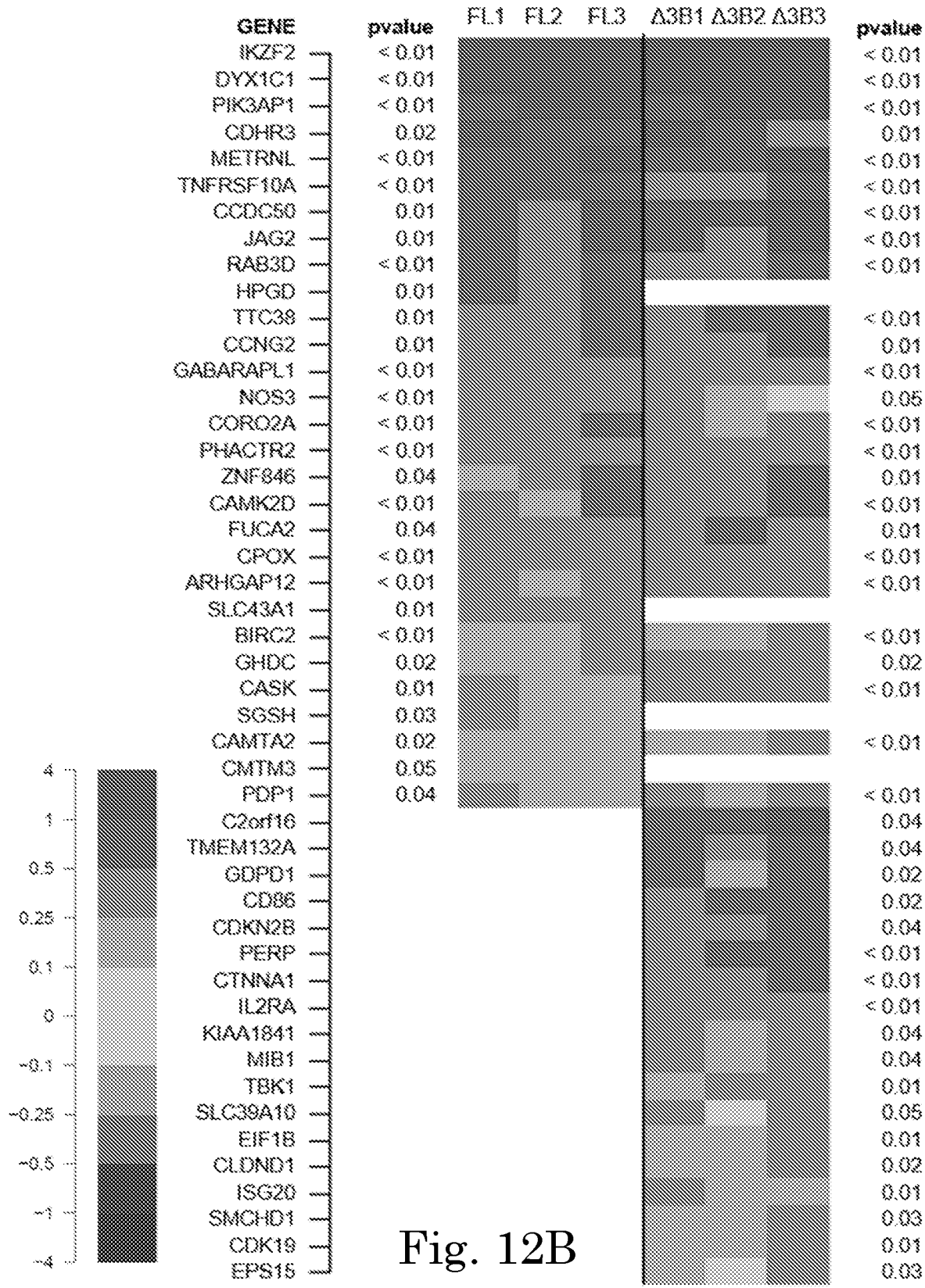

FIG. 12B is a heatmap comparing expression of Treg signature genes that are upregulated in CD8+ eTregs (TREG UP) compared to Tconv, showing differential expression of genes in each of the three donors for FOXP3 vs FOXP3+Hel-FL (FL, donors FL1-FL3) and FOXP3 vs FOXP3+Hel-Δ3B (Δ3B, donors d3b1-d3b3). For each cell in the heatmap, the difference of cpm values between two strains of cell for one subject was calculated and divided by average cpm value of that gene in all three subjects.

Figure 12C:
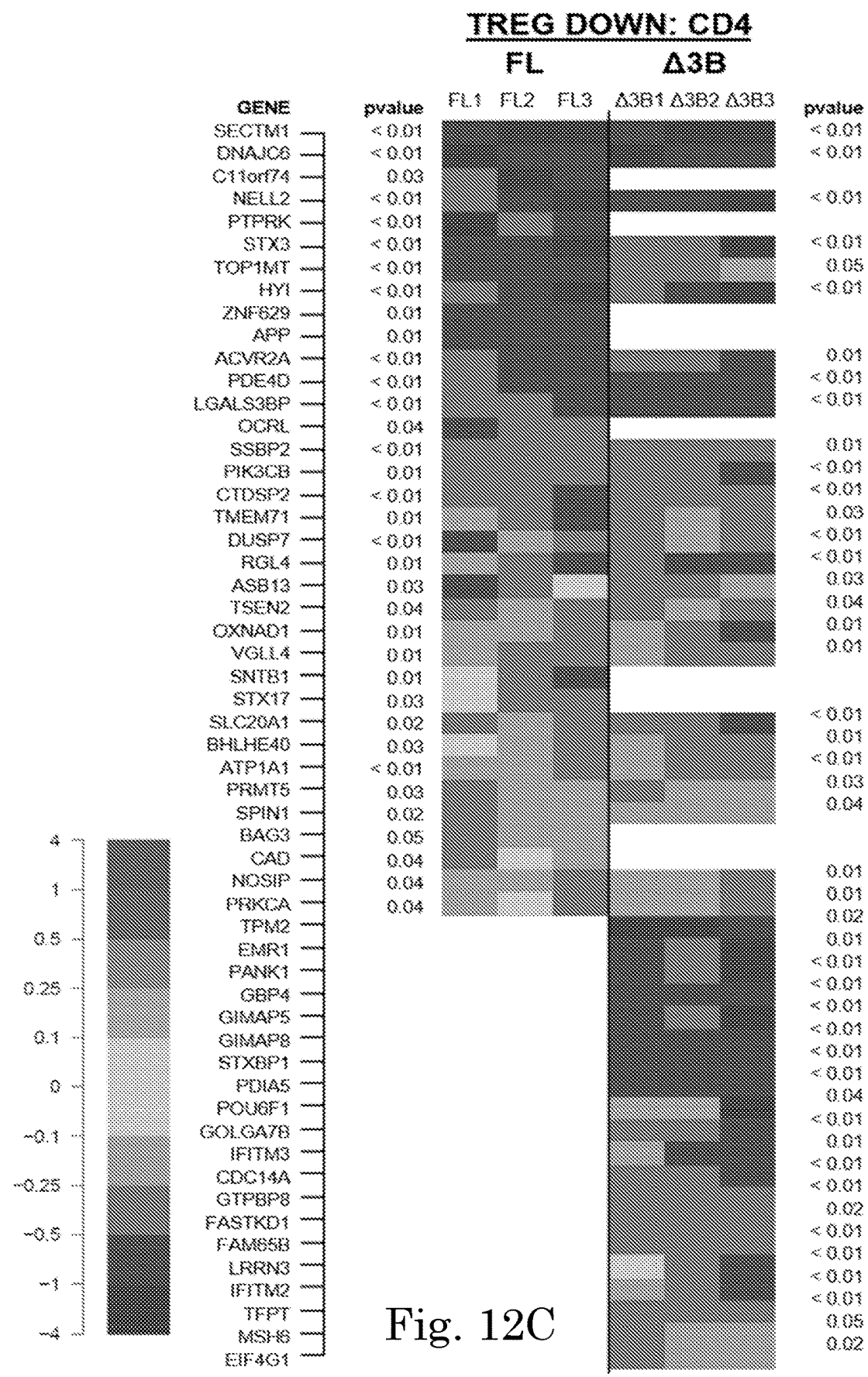

FIG. 12C is a heatmap comparing expression of Treg signature genes that are downregulated in CD4+ eTregs (TREG DOWN) compared to Tconv, showing differential expression of genes in each of the three donors for FOXP3 vs FOXP3+ Hel-FL (FL, donors FL1-FL3) and FOXP3 vs FOXP3+ Hel-Δ3B (Δ3B, donors d3b1-d3b3). For each cell in the heatmap, the difference of cpm values between two strains of cell for one subject was calculated and divided by average cpm value of that gene in all three subjects.

Figure 12D:
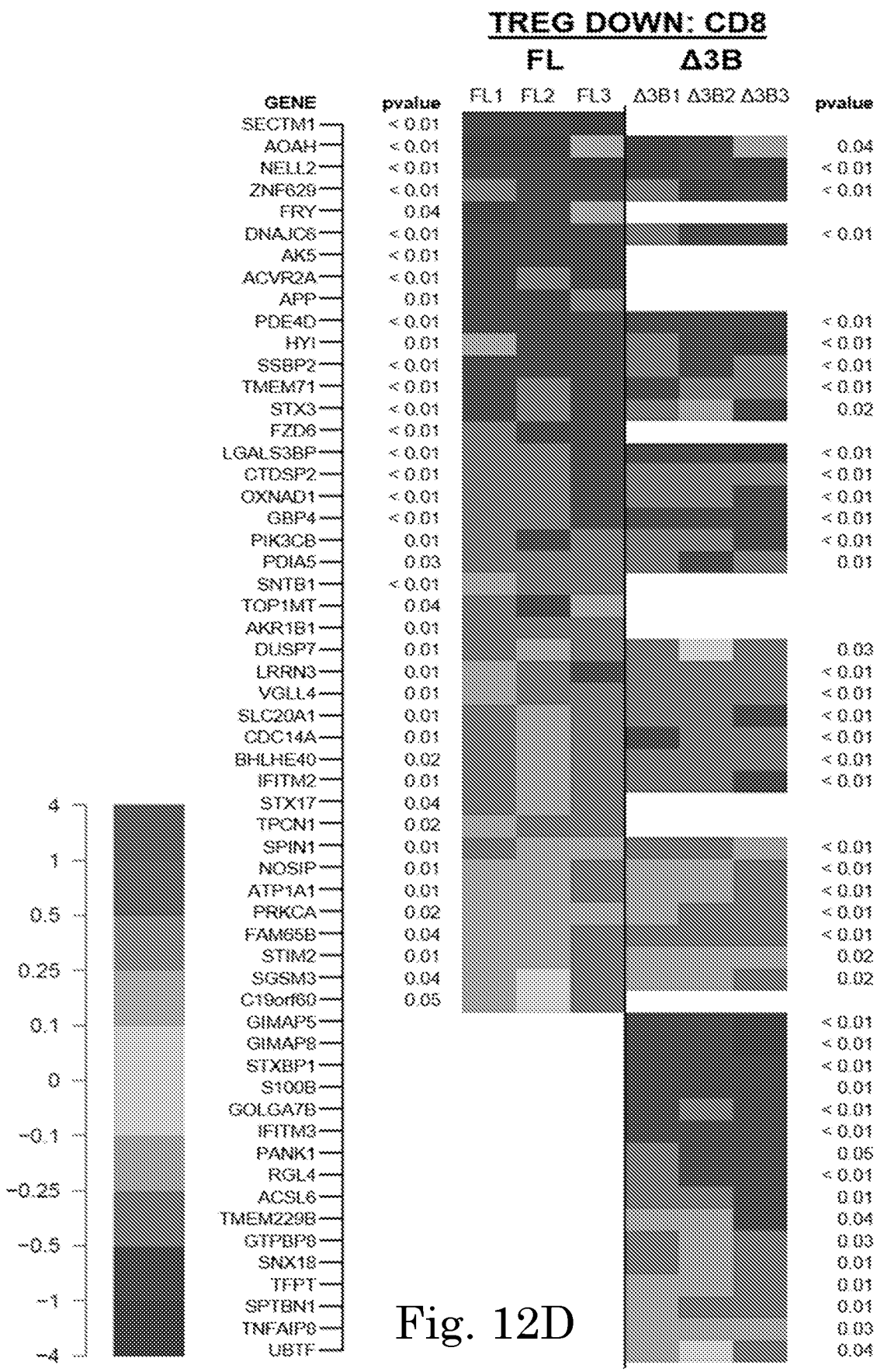

FIG. 12D is a heatmap comparing expression of Treg signature genes that are downregulated in CD8+ eTregs (TREG DOWN) compared to Tconv, showing differential expression of genes in each of the three donors for FOXP3 vs FOXP3+ Hel-FL (FL, donors FL1-FL3) and FOXP3 vs FOXP3+ Hel-Δ3B (Δ3B, donors d3b1-d3b3). For each cell in the heatmap, the difference of cpm values between two strains of cell for one subject was calculated and divided by average cpm value of that gene in all three subjects.

DETAILED DESCRIPTION

The present invention is concerned with cell therapy compositions comprising engineered human regulatory T cells (eTregs) characterized by ectopic overexpression of FOXP3 and Ikaros family transcription factors (preferably Helios), via introduction of nucleotide sequences (cDNA) for FOXP3 and preferably IKZF2 (aka FOXP3+Helios+ eTregs). FOXP3 is a member of the subfamily P of the FOX protein family. Members of the FOX protein family all have a forkhead/winged helix DNA binding region. Other structural features of FOXP3 include a central domain in the C terminus, which contains a C2H2 zinc finger and leucine zipper, and a repressor domain in the N-terminus. FOXP3 primarily mediates transcriptional regulation through interaction with other transcription factors. The forkhead domain of FOXP3 binds the target sequence of AP-1, a downstream transcription factor that is activated with TCR signaling. Consequently, binding of FOXP3 to this sequence blocks AP-1-NFAT interaction and inhibits T cell activation. FOXP3 alters T cell transcription through formation of oligomers with other transcription factors via the zinc finger and leucine zipper domains. The five members of the Ikaros family are Ikaros, Helios, Aiolos, Eos and Pegasus. Each Ikaros family member has four DNA-binding zinc finger motifs near the N-terminus and two C-terminal zinc fingers that mediate protein-protein interactions. Each family member can homodimerize or heterodimerize via the C-terminal zinc fingers in every possible combination. Furthermore, each member can undergo alternative splicing that eliminates one or more of the N-terminal zinc fingers. Helios and Eos are highly expressed in a majority of Tregs.

The eTregs are isolated from a total T cell transduced population of human cells, preferably primary T cells. Preferably, compositions of the invention comprise at least CD8+ Treg cells with ectopic overexpression of FOXP3 and Helios (CD8+ FOXP3+Helios+eTregs). More preferably, compositions of the invention comprise mixed populations of CD4+ and CD8+ Treg cells each with ectopic overexpression of FOXP3 and Helios (CD4+FOXP3+Helios+ eTregs and CD8+FOXP3+Helios+eTregs). These compositions are useful in treating individuals suffering from inflammatory and/or immune-mediated diseases and conditions.

Advantageously, eTregs in accordance with embodiments of the invention maintain stable overexpression of the FOXP3 and/or Helios gene products via stably expressed cDNA sequences, over several generations, and preferably stable co-expression of the gene products. In particular, natural (i.e., non-engineered) Tregs can lose FOXP3 expression over time converting them to a pro-inflammatory phenotype, which would be detrimental in the context of therapeutic applications. Thus, the eTregs according to embodiments of the invention preferably remain CD4+ FOXP3+Helios+ and/or CD8+FOXP3+Helios+ over several generations (i.e., rounds of replication). In one or more embodiments, the eTregs further express at least one additional marker selected from the group consisting of CD25, CD127, CD73, CCR4, and combinations thereof. Preferably, expression of CD127 in the inventive eTregs is significantly decreased compared to a control (empty vector-transduced) T cells for CD4+ eTregs. Further, expression of CCR4 and/or CD25 is preferably significantly increased compared to empty vector-transduced T cells for both CD4+ and CD8+ eTregs. These changes in these markers indicate that the inventive eTregs have Treg functionality, as compared to empty vector-transduced T cells. As used herein, a decrease or increase is considered "significant" if p≤0.05 using statistical tests indicated. In one embodiment, the eTregs in vitro maintain expression of at least FOXP3, as well as one or more additional markers noted above for at least 9 days post transduction, preferably at least 14 days, and more preferably at least 21 days post transduction. In one embodiment, eTregs maintain in vitro expression of at least FOXP3, as well as one or more additional markers noted above for at least 5 days, and preferably at least 9 days post transduction. In one embodiment, after administration, the eTregs preferably maintain in vivo expression of at least FOXP3, as well as one or more additional markers noted above for at least 10 days, and preferably at least 12 days.

In addition to ectopic overexpression of FOXP3 and Helios, the eTregs further exhibit expression of one or more transduction markers for subsequent isolation/purification as well as for in vivo tracking. Exemplary transduction markers include cell surface markers, such as CD19, preferably signaling deficient, truncated CD19, and/or CD34, preferably signaling deficient, truncated CD34, which are co-inserted into the cell during transduction.

The eTregs comprise nucleic acid constructs stably incorporated therein, each comprising respective nucleotide sequences encoding for Helios and FOXP3. That is, the eTregs comprise a first nucleic acid construct encoding for FOXP3 and a second (distinct) nucleic acid construct encoding for Helios, each stably incorporated therein. Preferably, the nucleic acid constructs comprise cDNA for Helios (SEQ ID NO:1 or 5) and codon optimized FOXP3 (SEQ ID NO:3) coding sequences, respectively. Preferably, the eTregs ectopically express only one isoform of Helios, unlike natural Tregs. More preferably, the eTregs comprise nucleic acid constructs stably incorporated therein comprising the full-length Helios coding sequence (SEQ ID NO:1), and even more preferably exclude a coding sequence for the short isoform of Helios (SEQ ID NO: 5, Hel-A3B). Each nucleic acid construct for FOXP3 and Helios preferably further comprises a coding sequence for a transduction/ selection marker as noted above to facilitate positive identification and selection/separation/purification of successfully transduced cells. In one or more embodiments, the marker sequences are linked to the FOXP3 or Helios sequence (respectively) via 2A linkers.

As noted, Tregs are genetically modified to encode desired expression products and yield the inventive eTregs. Tregs are found in a variety of biological samples, including peripheral blood, umbilical cord blood, plasma, lymph node, human thymus, as well as from cultured cells, such as in vitro induced Tregs (iTregs). Unlike prior methods, the inventive eTregs are generated from a total T cell transduced population of human cells, preferably primary T cells. Accordingly, methods of the invention include converting at least a portion of a total T cell population to eTregs, such that eTreg yield can be increased 2 to 8 times as compared to conventional processes for isolating Tregs. In general, to prepare eTregs from a sample, mononuclear cells are first isolated or separated from the sample (identified as any blood cell with a round nucleus), such as by using density gradient centrifugation. Having a lower density, the mononuclear cells remain in the upper fraction after centrifugation and can be removed, e.g., using a pipette or other filter method. The isolated or separated mononuclear cell fraction is then cultured or incubated under appropriate conditions to favor activation, stimulation, and/or expansion of at least a portion of the T cell population present in the isolated mononuclear cells. General methods of culturing T cells so that they are activated, grow, and/or expand are known to those skilled in the art, and are referred to herein as "T cell culture conditions." Exemplary T cell culture conditions are demonstrated in the Examples. For example, mononuclear cells collected from a patient are stimulated with monoclonal antibodies (MAb), such as anti-CD3 and anti-CD28, along with exogenous IL-2 to select for and further expand T cells within the mononuclear cell sample.

Thus, the initial mononuclear cell population is allowed to grow and divide such that cell numbers, including T cell numbers, are increased. More preferably, the initial mononuclear cell population is cultured under conditions (aka T cell culture conditions) that favor T cells, such that B cells, macrophages, and the like are reduced in the mononuclear cell population. Again, examples of such conditions include stimulation with anti-CD3 and anti-CD28 antibodies and culture in IL-2 supplemented media. The resulting cell population preferably consists essentially of T cells, more specifically, about 95% of the remaining cells (as identified by staining) in the population after being subjected to the T cell culture conditions are T cells, and is referred to herein as the "total T cell population." It will be appreciated that the total T cell population could be subjected to further techniques for enrichment and/or expansion of T cell numbers before applying the transduction protocol, if desired.

The total T cell population is then subjected to the transduction process. That is, unlike prior approaches, the inventive technique does not first involve purification, separation, and/or isolation of CD4+ and/or CD8+ cells before genetic modification. Rather, the total T cell population is transduced with the respective recombinant nucleic acid molecules. In one or more embodiments, transduction is initiated at least 1 day after subjecting the cell population to T cell culture conditions, preferably at least 2 days after, more preferably from about 2 days to about 10 days after subjecting the cell population to T cell culture conditions, even more preferably from about 2 to about 6 days, and even more preferably at about 2 to about 3 days when the cells are in their most active proliferation stage.

Each nucleic acid is usually incorporated into a vector, such as a recombinant viral vector (e.g., retroviral or lentiviral vector), a plasmid, etc., for introduction and stable incorporation into the cells. Thus, terms like "engineered" or "genetically modified" mean that the eTregs comprise a nucleic acid molecule not naturally present in natural Tregs, such that the introduced nucleic acid molecule is ectopically expressed in the eTregs. In the current invention, the cells are transduced with two separate vectors, which results in co-overexpression of FOXP3 and Helios in the eTregs conferring a number of beneficial traits not seen in natural Tregs. Importantly, in the eTregs, the ectopic nucleic acid molecule may have been introduced directly into a particular eTreg cell or into an ancestor thereof.

Preferably, virus-mediated gene transfer is used to introduce each nucleic acid molecule into the T cells. The nucleic acid molecules to be transferred are first introduced into a recombinant virus, and preferably a recombinant retrovirus, which is then used to transduce the Tregs in the total T cell population. Retroviruses facilitate stable integration of the genes of interest, and include lentivirus vectors, gamma retroviral vectors, alpha retroviral vectors, and the like. Particular examples of human retroviral transfer vectors include pSFG, pMIG, pBABE, pLenti, and the like. More specifically, retroviral vectors in accordance with the invention are first used to infect packaging cells, such as HEK cells, Phoenix-eco cells, and the like. The transfected packaging cells then produce recombinant viral particles that include the nucleic acid construct to be introduced into the T cells in the total T cell population. Methods for retroviral transfection are known in the art. After transfection, the recombinant viral particles/virions are then recovered from the media and used to infect the T cells in the total T cell population, by contacting the cells with the virion containing the retroviral vector described herein.

In general, each of the nucleic acid constructs will comprise respective nucleotide sequences (cDNA) encoding FOXP3 or Helios. Thus, at least two different/distinct nucleic acid constructs are contemplated herein for separate (and preferably sequential) transduction as described in more detail below. A preferred coding sequence for FOXP3 is exemplified in the working examples and has been codon-optimized for expression in human T cells. Preferred coding sequences (cDNA) for Helios are exemplified in the working examples. As noted in the examples, the eTregs preferably include ectopic expression of only one isoform of Helios (full length); in contrast to natural Tregs, which usually include two isoforms. The nucleic acid construct cloned into each vector typically comprises, in addition to a coding region, regulatory sequences, such as a promoter operably linked to each nucleotide sequence. Preferably, expression of the inserted coding sequences for FOXP3 or Helios are each driven by a constitutively expressed retroviral promoter in the 5' long terminal repeat (LTR) and thus, not affected by endogenous regulators of FOXP3 and Helios expression, to help facilitate high co-expression of the proteins from respective constructs. Constitutively expressing Treg transcription factors help stabilize the eTreg phenotype by out competing any other transcription factors that could convert the eTreg into a Tconv. Each nucleic acid construct further comprises at least one sequence encoding for a transduction marker. Exemplary marker sequences include sequences for ΔCD19 and ΔCD34. In one or more embodiments, truncated transduction markers encoding for ΔCD19 (SEQ ID NO:10) and ΔCD34 (SEQ ID NO:12) are used. In one or more embodiments, the transduction markers coding sequences comprise ΔCD19 (SEQ ID NO:9) and ΔCD34 (SEQ ID NO:11). Preferably, a different transduction marker is used for each of the FOXP3 and Helios nucleic acid constructs. Preferably, each transduction marker is linked to FOXP3 or Helios, respectively, via a 2A linker. The vectors can also include an inducible caspase that can act as a suicide gene should the eTregs result in any unwanted side effects.

The eTregs can also be engineered to express a variety of targeting moieties that can bias them to a specific tissue, resulting in localized immunosuppression. Targeting moieties include compounds, chemical entities, molecules, or parts of molecules, that confer a degree of specificity towards a target, such as a certain cell type, including those that have targeted binding with a useful degree of specificity to a target, or otherwise functionally interact with a binding site on a cell surface, such as cell surface receptors. Examples of targeting moieties are known in the art and include antibodies or fragments, receptor ligands, peptide moieties that facilitate receptor recognition, antigen receptors, carbohydrates, fatty acids, polymers, peptidomimetic molecules, and the like, including recombinant or synthetic versions thereof.

In one or more embodiments, the nucleotide sequences encoding FOXP3 and Helios are introduced into the total T cell population via separate and distinct vectors. Although simultaneous transduction with each separate vector can be carried out, preferably, a sequential transduction protocol is used, wherein the cell population is contacted with viral particles comprising the recombinant viral vector encoding for Helios followed by positive selection of successfully Helios transduced cells. Selection of successfully transduced cells is preferably carried out through selection of one or more transduction markers expressed by the Helios transduced cells (i.e., the transduction marker that was included in the Helios nucleic acid construct). Preferably, selection of successfully Helios transduced cells is via magnetic bead purification based upon surface markers co-expressed with Helios (from the nucleic acid construct). In one or more embodiments, the population of Helios transduced cells may be cultured, expanded/enriched, or even stored for a desired period of time before moving to the next transduction event, if desired. The Helios transduced cells are then contacted with viral particles comprising the recombinant viral vector encoding FOXP3, followed by positive selection of successfully FOXP3 transduced cells. Again, selection of successfully FOXP3 transduced cells is preferably carried out through selection of one or more transduction markers expressed by the FOXP3 transduced cells (i.e., the transduction marker that was included in the nucleic acid construct for FOXP3). Preferably, selection of successfully FOXP3 transduced cells is via magnetic bead purification based upon surface markers co-expressed with FOXP3 (from the nucleic acid construct).

In one or more embodiments, the sequential transduction protocol described above can be reversed, wherein cells are first transduced with nucleic acid constructs encoding FOXP3, followed by introduction of nucleic acid constructs encoding Helios, without departing from the scope of the invention. The order of transduction does not appear to affect overall expression of the gene products. Advantageously, the sequential transduction technique avoids suppression of FOXP3, which is observed when both genes are introduced via the same vector. Accordingly, prior to the inventive sequential transduction technique, it was not possible to achieve co-overexpression of both FOXP3 and Helios as achieved in the current invention.

The resulting cell population after both transduction and selection steps comprises a mixture of CD4+ eTregs and CD8+ eTregs, each with co-overexpression of both FOXP3 and Helios. As used herein "overexpression" of a gene product means that the level of expression transcripts are statistically significantly ($p \leq 0.05$) increased as compared to naturally occurring cells. Preferably, the eTregs have expression levels of FOXP3 of at least 5 times that of natural Tregs, more preferably at least 10 times that of natural Tregs, and even more preferably at least 12 times that of natural Tregs. Preferably, the eTregs have expression levels of Helios of at least 2 times that of natural Tregs, more preferably at least 3 times that of natural Tregs, and even more preferably at least 4 times that of natural Tregs. Preferably, the resulting eTreg cell population after the transduction and selections steps consists essentially or even consists of a mixture of CD4+ eTregs and CD8+ eTregs, each with co-overexpression of both FOXP3 and Helios. That is, further purification is not necessary to yield a substantially pure population of CD4+ eTregs and CD8+ eTregs. If desired, CD4+ eTregs can be further separated from CD8+ eTregs via magnetic bead purification. It will be appreciated that by transducing total T cell populations, higher numbers of therapeutic Treg cells can be achieved than with previous protocols, which focused solely on initially purified CD4+CD25+ cells. Prior to the invention, such compositions were impractical, or even impossible, to produce. Further, as demonstrated in the working examples, the development of CD8+ eTregs further enhances the therapeutic efficacy of prior approaches, which relied solely on CD4+ cell populations.

The eTreg cell compositions can be used to treat a disease or condition in which it is desirable to suppress the immune system or reduce pro-inflammatory responses (e.g., cytokine storm) in a subject. In one or more embodiments, autologous treatment methods are contemplated which involve first collecting or obtaining a biological sample from the patient or subject to be treated, such as peripheral blood, umbilical cord blood, lymph node, thymus, and the like. The treatment method includes isolation of mononuclear cells and ex vivo expansion of T cell populations from the autologous sample as noted above. The subject's T cells can then be transduced and selected as noted above to generate eTregs specific to the patient, before being infused or injected back into the patient as part of the therapy. In one or more embodiments, autologous treatment methods are contemplated, which involve ex vivo expansion/activation/stimulation of a donor biological sample and/or cultured cells, followed by transduction and the selection of successfully transduced cells as described above for use in "off the shelf" allogeneic therapies. In one or more embodiments, the sample may be one that has been collected from the subject or the donor at an earlier timepoint, and stored for later use, for example umbilical cord blood from birth of the subject (or donor), banked for later use. In one or more embodiments, the sample is cryopreserved. In one or more embodiments, the mononuclear cells from the sample may be isolated/cultured before cryopreservation. In one or more embodiments, the mononuclear cells may be isolated/cultured from the sample after cryopreservation (and thawing). In one or more embodiments, the treatment method involves expansion/activation/stimulation of an induced T cell population artificially generated from pluripotent stem cells (Montel-Hagen et al., *Organoid-Induced Differentiation of Conventional T Cells from Human Pluripotent Stem Cells*, 24 Cell Stem Cell 376-389 (2019)). The induced T cell population can then be transduced and selected as describe above. In any event, the resulting eTreg cell compositions comprise eTregs with ectopic overexpression of both FOXP3 and Helios.

The compositions may be used prophylactically and/or therapeutically. Thus, methods of the invention include prophylactic and/or therapeutic administration of a composition according to embodiments of the invention for the purpose of preventing, mitigating/reducing, alleviating, or delaying a disease or condition involving inflammation and/or a disorder of the immune system. As used herein, "prophylactic" refers to administration of the composition before the subject exhibits observable (e.g., visually or through diagnostic tests) symptoms of the disease or condition, but is identified as being at risk for developing the disease or condition. It includes use in a subject that may already have early onset of the disease or condition, but which again, does not yet exhibit detectable symptoms or has not been diagnosed as such. It also includes prophylactic administration to inhibit or minimize symptoms, such as in the case of prophylactic administration of the eTregs in a transplant recipient before surgery. In contrast, "therapeutic" uses of the composition refer to administration of the composition to a subject that is or has exhibited symptoms of the disease or condition. Accordingly, a prophylactic treatment method refers to administration of the composition in advance of the disease or condition, and does not necessarily mean that the composition "prevents" the disease or condition, but instead may only inhibit, reduce, mitigate, delay, or alleviate one or more symptoms of the disease or condition. Further, compositions of the invention are intended to be used both prophylactically and therapeutically as part of the same treatment regimen for many diseases or conditions, wherein treatment is started prior to the onset of the disease or condition and continues after or throughout the course of the disease or condition (e.g., repeatable dosing regimens).

Compositions of the present invention are particularly useful for prophylactically and/or therapeutically treating autoimmune diseases or inflammatory diseases, such as diabetes, multiple sclerosis, graft vs. host disease (GVHD), allograft/transplant rejection, IBD, lupus, rheumatoid arthritis, and other chronic inflammatory diseases, and the like. Compositions may be administered as part of a treatment for inhibition of transplant rejection or GVHD after a transplant of tissues, such as bone marrow, hematopoietic stem cells, lymphocytes, heart, liver, eye (cornea), kidney, lung, pancreas, etc. Compositions of the present invention can also be administered to a subject at risk for developing an autoimmune disease, for example, due to exposure to environmental contaminants (e.g., chemicals, drugs), genetic factors, and the like, which may be revealed through diagnostic and/or genetic testing. The compositions may also find use in combatting inappropriate immune responses (e.g., cytokine storm) in supportive treatments for infectious disease.

Various administration routes and protocols may be used to carry out the treatment processes. In general, the eTregs according to the various embodiments of the invention are suspended in a pharmaceutically acceptable medium or vehicle suitable for therapeutic or prophylactic administration to create the treatment composition. In general, administration may be systemic or local/direct, including an intravenous infusion or an intraarterial, intraperitoneal, intramuscular, or subcutaneous injection. The composition may be administered before, during, and/or after transplantation or graft in the subject, such via intravenous infusion and/or direct local injection during surgery. Repeated administrations are also contemplated after transplantation to further delay or inhibit onset of the disease or condition associated with an unsuitable immune response to the transplant or graft. In the case of various chronic and/or acute immune conditions, the compositions can be administered repeatedly over designated intervals of time (e.g., every 12 hours, every 30 days, etc.), if warranted. The composition is administered in a suitable dosage based upon the age and weight of the patient, such that the composition contains a sufficient number of eTregs to provide a therapeutically effective dosage. A dosage is considered "therapeutically effective" if it inhibits, reduces, mitigates, delays, or alleviates one or more symptoms of the disease or condition in the subject. Advantageously, the eTregs according to the invention have decreased expression of at least one or more of the following pro-inflammatory proteins, including IL-2, IL-4, and/or IFNγ. Further, eTregs mediate suppression of T cell proliferation further suppressing any undesired or overactive immune response in the patient.

Embodiments of the invention also include kits useful for practicing the disclosed methods of the present invention. For example, kits may include nucleic acid sequences for generating nucleic acid constructs and eTregs from a patient sample (e.g., cDNA encoding FOXP3, Helios, transduction markers, etc.), and instructions for using the kit, along with various reagents, such as buffers, media, and materials for stimulation/activation of collected T cells and ex vivo expansion. Kits may also include suitable equipment for collection and/or processing of patient samples.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Co-Expression of FOXP3 and a Helios Isoform Enhance the Effectiveness of Human Engineered Regulatory T Cells Summary Regulatory T cells (Tregs) are a subset of immune cells that suppress the immune response. Treg therapy for inflammatory diseases is being tested in the clinic with moderate success. However, it is difficult to isolate and expand Tregs to sufficient numbers. Engineered Tregs (eTregs) can be generated in larger quantities by genetically manipulating conventional T cells (Tconv) to express FOXP3. These eTregs have been shown to suppress the immune response in vitro and in vivo but not as effectively as endogenous Tregs. In this work, we demonstrate that ectopic expression of the transcription factor Helios along with FOXP3 is required for optimal eTreg immunosuppression. We generated eTregs by retrovirally transducing total human T cell populations with cDNA encoding FOXP3 without and with cDNA encoding the full length isoform of Helios (Hel-FL) and/or Δ3B Helios (Hel-Δ3B), a relevant splice variant of Helios. FOXP3+Hel-FL (aka FOXP3+Helios+) eTregs were the only eTregs able to delay disease in a xenogenic GVHD model. In vitro, FOXP3+Hel-FL CD4+ and CD8+ eTregs suppressed T cell proliferation more effectively than FOXP3+ CD4+ and CD8+ Tregs and FOXP3+ Hel-Δ3B CD4+ eTregs. However, both FOXP3+Hel-FL CD8+ eTregs and FOXP3+Hel-Δ3B CD8+ eTregs were more effective than FOXP3+ alone. RNA Sequencing of the CD4+ and CD8+ eTregs demonstrated that the addition of Hel-FL to FOXP3 in eTregs changed gene expression in cellular pathways and the Treg signature compared to FOXP3 alone or FOXP3+Hel-Δ3B. Thus, overexpression of Hel-FL with FOXP3 in eTregs changed gene expression in Tconvs and mediated immunosuppression in vivo and in vitro. Additionally, there is a functional difference between the endogenous splice variants of Helios in mediating CD4+ and CD8+ T cell immunosuppression.

Introduction

Tregs are a subset of T cells that promote immune tolerance and suppress the immune response. Tregs represent 3-5% of CD4+ T cells in the blood and are characterized by the expression of the FOXP3 transcription factor, high CD25 and low CD127 expression. A majority of Tregs are thymus-derived Tregs (tTregs), generated in the thymus during T cell development. Naïve T cells can also differentiate into peripherally-derived Tregs (pTregs). Tregs mediate immune homeostasis through suppression of immune activity. Tregs down-regulate the immune response via a variety of mechanisms such as inhibiting pro-inflammatory conventional T cell (Tconv) proliferation and activation, secretion of immunosuppressive cytokine, killing of reactive immune cells, and induction of anergy.

The immunosuppressive properties of Tregs have led to much research into utilization of Tregs as a cellular therapeutic. The most numerous clinical trials are aimed at preventing Graft versus host disease (GVHD). GVHD is a common complication in allogeneic hematopoietic stem cell transplant (HSCT) that results in about 15-30% of the deaths following transplantation. GVHD manifests when donor immune cells, primarily T cells, attack recipient organs. Various studies have used Tregs isolated from leukopheresed blood and co-infused with hematopoietic stem cells Alternatively, Tregs can be expanded from cord blood. Other clinical trials are testing Tregs as treatments for IBD, type I diabetes and transplant rejection. These trials have shown that Treg infusions are safe, but only moderately successful. A major challenge is expanding Tregs to numbers required for effective treatment.

Engineered Tregs (eTregs) are generated by transducing Tconv populations with genes known to convey Treg activity. T cell transduction technology is currently being used to express chimeric antigen receptors in T cells for cancer immunotherapy and has been proven to be safe. eTregs provide solutions to many of the limitations of endogenous Tregs. As demonstrated herein, co-expression of Treg genes with a transduction marker allows for purification of transduced cells and ensures homogeneity of the cell population. Constitutively expressing Treg transcription factors stabilizes Treg phenotype. Finally, eTregs can be modified to express targeting moieties, such as chimeric antigen receptors, that can target them to a specific tissue resulting in localized immunosuppression.

High expression of the transcription factor FOXP3 is a hallmark of Tregs. FOXP3 is necessary for Treg-mediated immune homeostasis, as mice and humans deficient in FOXP3 develop severe autoimmune diseases. Enforced FOXP3 expression in human CD4+ T cells mediates suppression of Tconv proliferation in vitro. FOXP3-transduced cells can reduce symptoms in murine colitis and GVHD models. However, in a study using a murine arthritis model, FOXP3-transduced cells were not as effective as endogenous Tregs at reducing joint destruction or decreasing the number of pathogenic Th17 cells in the joint. Additionally, microarray data has shown that FOXP3 is not sufficient to convey complete Treg gene regulation in murine T cells. These observations indicate that FOXP3-expressing eTregs show promise, but expression of additional genes is required to generate engineered cells that function as well as endogenous Tregs.

In addition to FOXP3, the transcription factor Helios, a member of the Ikaros family, is highly expressed in about 70% of FOXP3+ Tregs. In humans, FOXP3+ Helios+ Tregs more effectively suppress Tconv cytokine secretion and are more stable under inflammatory conditions than FOXP3+ Helios− Tregs. We demonstrate here that ectopic expression of Helios with FOXP3 is required for optimal eTreg immunosuppression activity. Here, we report that through dual retroviral transduction, total human T cell populations can be genetically modified to ectopically express high levels of both FOXP3 and Helios. We generated eTregs that co-expressed FOXP3 with and without the following two endogenous splice variants of Helios found in human Tregs: full length Helios (Hel-FL) and a shorter form, Δ3B Helios (Hel-Δ3B). FOXP3+Hel-FL eTregs were the most effective at immunosuppression in vivo in a xenogeneic GVHD model and in an in vitro suppression assay. Adding Hel-FL to FOXP3 in eTregs was able to convey immunosuppressive properties to both CD4+ and CD8+ human Tregs and these eTregs had differential gene expression and enrichment of cellular pathways at a transcriptional level compared to FOXP3 and FOXP3+ Hel-Δ3B eTregs. Thus, we were able to improve current eTreg production and generate both CD4+ and CD8+ eTregs by ectopically over expressing FOXP3 and Hel-FL in total T cell populations.

Materials and Methods

Isolation of Human Peripheral Blood Mononuclear Cells (PBMC)

All studies involving human subjects were conducted in accordance with the guidelines of the World Medical Association's Declaration of Helsinki. Blood was collected from healthy adult volunteer donors with signed informed consent and approval from the Institutional Review Board of the University of Kansas Medical Center. Blood was collected in heparin tubes and PBMCs were isolated via Ficoll-Paque (GE Healthcare, Chicago, IL) density centrifugation with SepMate tubes (STEMCELL Technologies Inc., Vancouver, BC).

Construction of Retroviral Vectors and Production of Retroviral Particles

Retroviral constructs were generated to express cDNA for full length Helios (SEQ ID NO:1, "Hel-FL"), a shortened isoform of Helios (SEQ ID NO:5, "Hel-Δ3B"), or FOXP3 (SEQ ID NO:3), (FIG. 2A). The NCBI Reference Sequences for FOXP3, Hel-FL and Hel-Δ3B are NM_014009.3, NM_016260.2 and NM_001079526.1, respectively, incorporated by reference herein. The SFG retroviral vector, RDF and pEQPAM3 retroviral packaging plasmids were generously donated by Dr. Malcom Brenner at Baylor College of Medicine. cDNA was cloned into the SFG vector via Gibson Assembly. The expression of cDNA is driven by a strong retroviral promoter in the 5' LTR. Multiple genes of interest were expressed by linking them in frame with a picornavirus 2A ribosomal skip peptide, which ensures equivalent expression of multiple proteins. The FOXP3 construct contains truncated CD19 (ΔCD19) cDNA and the Hel-FL and Hel-Δ3B contains truncated CD34 (ΔCD34) cDNA which act as transduction markers and allowed for purification of transduced cells via antibody-bound magnetic beads. The NCBI Reference Sequences for CD19 and CD34 are NM_001178098.1 and NM_001025109.1 respectively, incorporated by reference herein. The truncated ΔCD19 (SEQ ID NO:9 & 10) and ΔCD34 (SEQ ID NO:11 & 12) sequences only contain the signal peptide, extracellular, and transmembrane regions of the protein. ΔCD19 and ΔCD34 alone vectors were also generated as negative controls. FOXP3 (SEQ ID NO:3), ΔCD19, and ΔCD34 cDNAs were codon optimized with the Invitrogen GeneArt Gene Synthesis service (Thermo Fisher Scientific, Waltham, MA) prior to being cloned into the SFG vector. Hel-FL and Hel-Δ3B gene cDNA sequences (SEQ ID NO:1, 5) were not altered prior to cloning. Viral particles were generated by transfecting HEK 293T cells with SFG vectors containing the genes of interest and the retroviral packaging vectors. Transfection was carried out with Fugene HD Transfection Reagent (Promega, Madison, WI). Viral supernatants were collected 2 and 3 days after transfection and stored at −80° C. until use.

Activation of Primary T Cells from PBMCs

Human T cells were activated in complete media containing Aim V medium (Thermo Fisher Scientific, Waltham, MA) and 2% human AB serum (Bio-Techne, Minneapolis, MN). $3 \times 10^6$ PBMCs at $10^6$/mL were stimulated with plate bound anti-CD3 (2 μg/mL OKT3; Bio X Cell, West Lebanon, N.H.) and anti-CD28 (2 μg/mL 9.3; West Lebanon, NH). Briefly, human PBMCs were isolated from the collected blood via Ficoll separation. Stock solutions of Anti-CD3 antibody (clone OKT3; Bio X Cell) and Anti-CD28 antibody (clone 9.3; Bio X Cell) at 10 μg/μl were each prepared and stored at −20° C. A stock solution of human recombinant IL-2 (Peprotech) at 2000 U/μl was prepared and stored at −20° C.

Next, a 6-well non-tissue culture plate was coated with 2.5 ml per well of anti-CD3+anti-CD28 in PBS at 2 ug/ml each at 4° C. overnight or RT for at least 2 hours. Each well contained 10 μl of stock anti-CD3 at 0.5 μg/μl, 10 μl stock anti-CD28 at 0.5 μg/μl, and ~2.5 ml of PBS. The number of wells coated is based upon the total number of cells to be activated, with a target of $3 \times 10^6$ PBMCs per well. The isolated PMBCs were resuspended in complete Aim V (with 2% Human Serum AB) without IL-2. Cells were allowed to proliferate for 2 days. After 2 days of activation, cells were collected and complete medium was supplemented with 200 U/mL of recombinant human IL-2 (rhIL-2) (PeproTech, Rocky Hill, NJ), by replacing half the media with complete Aim V with IL-2 at 400 U/ml (40 ng/ml) to a final concentration of IL-2 at 200 U/ml (20 ng/ml). A high percentage of cells die at day 2. Proliferating T cells are characterized as being round and tending to clump together. Cells were then re-plated on the antibody coated plates, 3 mL per well, and cultured for another day. The cells were then collected and counted. The cells are resuspended at $10^6$ cells/ml in fresh complete Aim V with IL-2 at 200 U/ml (20 ng/ml). Cells were passed every 2-3 days at $1-2 \times 10^6$ cells/ml in complete AimV supplemented with rhIL-2 at 200 U/mL.

Transduction of Human T Cells

Figure 1A:
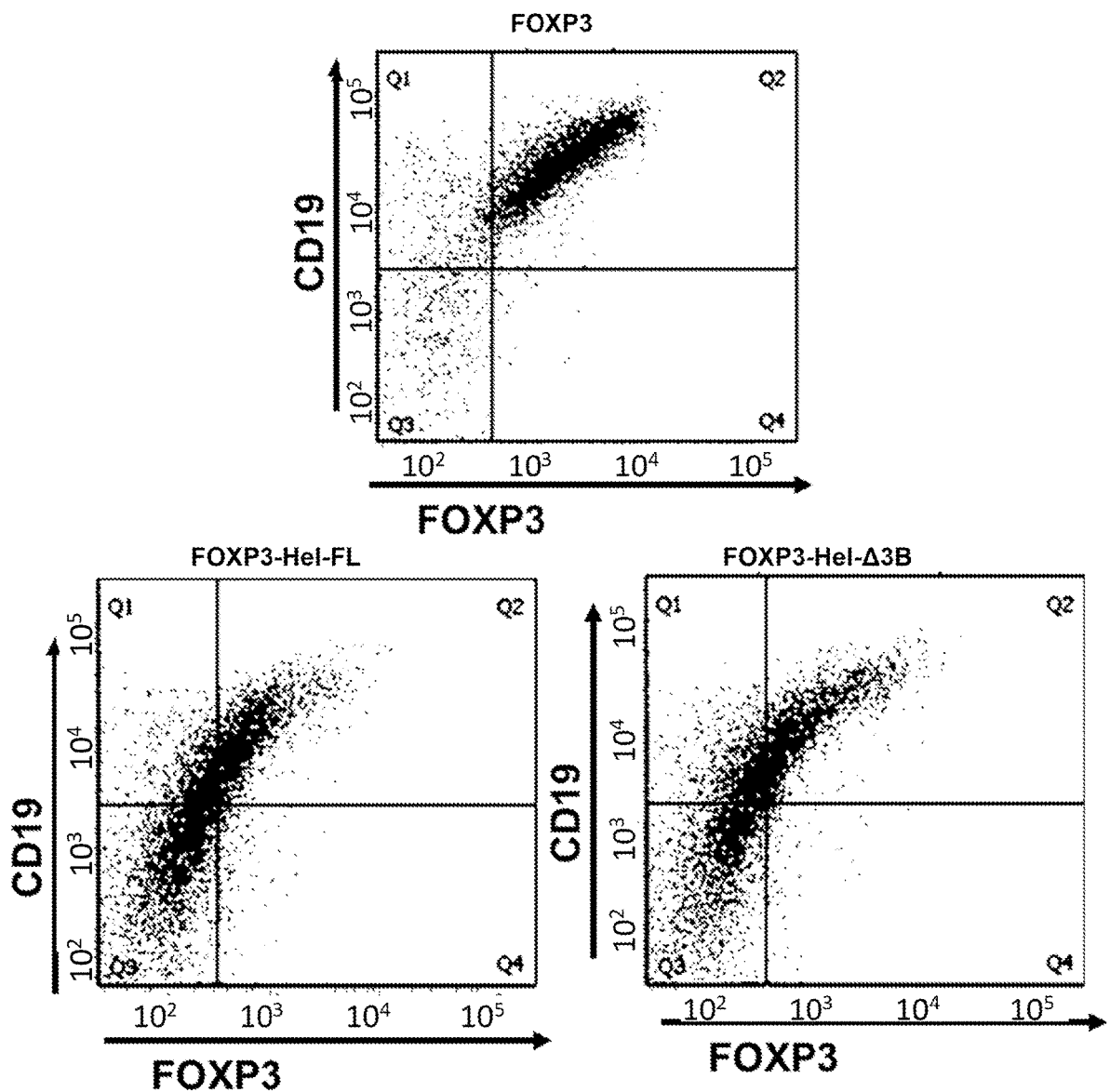
FIG. 1A shows representative dot plots. of CD19 and FOXP3 expression for FOXP3, FOXP3-Hel-FL and FOXP3-Hel-Δ3B transduced eTregs.
Figure 1B:
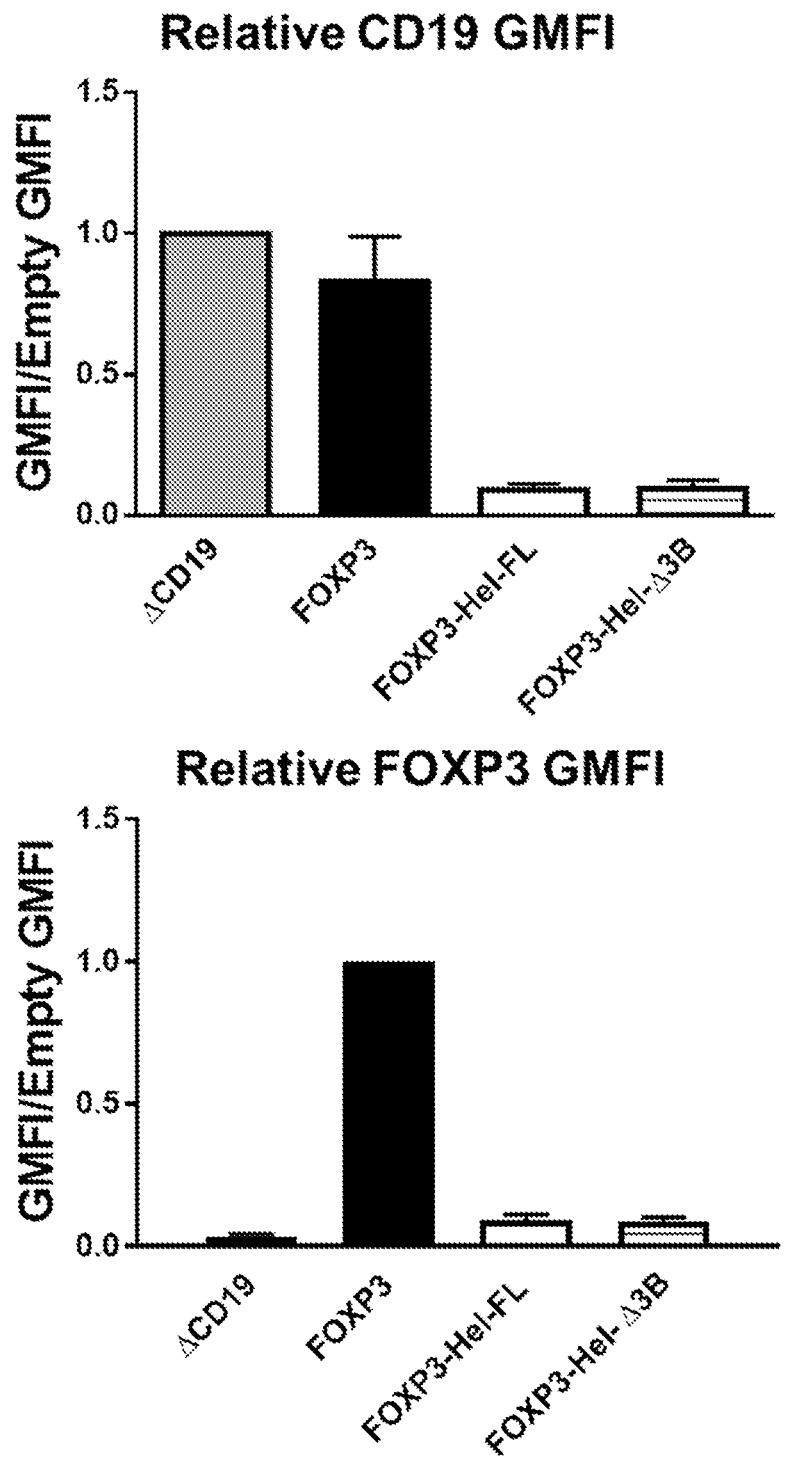
FIG. 1B shows graphs summarizing the geometric mean fluorescence intensity (GMFI) of FOXP3 and CD19 of the indicated eTreg population normalized to empty vector control cells. N=2.

The eTregs were generated from PBMCs isolated from three different healthy human donors. T cells were activated with anti-CD3 and anti-CD28 antibody stimulation, cultured in IL-2 containing media and transduced with retroviral particles containing cDNA for genes of interest. The cDNA on these cells were expressed on a single SFG retroviral vector. Transduced cells were purified with antibody-coated magnetic bead particle separation specific for the transduction marker ΔCD19. FIG. 1A shows representative dot plots of CD19 and FOXP3 expression for FOXP3, FOXP3-Hel-FL and FOXP3-Hel-Δ3B transduced eTregs. GMFI of FOXP3 and CD19 in the eTreg populations are shown in FIG. 1B.

In more detail, activated T cells were transduced with viral supernatants containing ΔCD34 vectors 5-6 days post activation. Non-tissue culture 6 well plates were coated in Retronectin (Takara Bio Inc., Kusatsu, Shiga Prefecture, Japan) at 20 μg/mL in PBS overnight at 4° C. or 2 hours at room temperature. 1.5 mL of viral supernatant per well was bound to Retronectin coated plates by centrifuging plates for 2 hours at 2000×g at 32° C. Viral supernatant was removed and 1.5 mL of viral supernatant along with $2.5-3 \times 10^6$ T cells were added to each well. T cells were in complete medium with rhIL-2 at 200 U/mL at $10^6$ cells/mL. Transduced cells are positively selected 2 days post transduction with anti-human CD34 CELLection magnetic beads (Thermo Fisher Scientific, Waltham, MA). Beads were removed with a magnet 2 days later and cells were then transduced with viral supernatants containing ΔCD19 vectors. Transduced cells were positively collected 2-3 days post transduction with CELLection Biotin Binder Kit beads (Thermo Fisher Scientific, Waltham, MA) coated with biotinylated anti-human CD19 (HIB19, Biolegend, San Diego, CA). Beads were removed 2 days later and used in assays up to 10 days post the last transduction. The resulting cell strains are summarized in Table 1.

TABLE 1

| Engineered Treg Strains | Transgenes Expressed |
|---|---|
| Control/Empty | ΔCD19 + ΔCD34 |
| FOXP3+ | FOXP3 + ΔCD19 + ΔCD34 |
| FOXP3+ & Full-length Helios | FOXP3 + ΔCD19 + Hel-FL-ΔCD34 |
| FOXP3+ & Truncated Helios | FOXP3 + ΔCD19 + Hel-Δ3B-ΔCD34. |

Real Time PCR

Helios splice variants were detected in transduced cell strains using real time PCR. RNA was isolated from cells using the Qiagen RNeasy Mini Kit (Qiagen, Germany). RNA was converted to cDNA using the Taqman High Capacity RNA to cDNA kit (Thermo Fisher Scientific, Waltham, MA). Real time PCR was performed using the forward (SEQ ID NO:7) and reverse (SEQ ID NO:8) primers for Helios. Splice variants were visualized using gel electrophoresis.

Mice and Xenogeneic Murine GVHD Model

All animal studies were performed in compliance with the U.S. Department of Health and Human Services Guide for the Care and Use of Laboratory Animals. NOD-SCID IL-2Rγ null (NSG) mice were purchased from Jackson Laboratories and bred at the University of Kansas Medical Center. Mice were maintained under specific pathogen-free conditions using sterile food, water, bedding, and caging.

NSG mice (8-12 weeks old) of both sexes received 1.5 Gy of whole-body irradiation. The next day, the mice were anesthetized via 2% inhaled isoflurane and injected retro-orbitally with $10^7$ human PBMC alone, $10^7$ PBMCs with $5 \times 10^6$ eTregs or PBS alone. Cells were re-suspended in 100 μl of sterile PBS. Mice were examined for signs of GVHD, using an established GVHD scoring system. Briefly, five categories were assessed on a scale of 0, 1, or 2 for each.

Weight loss: 0=<10% change, 1=10-25% change, 2=>25% change, Posture: 0=normal, 1=hunching at rest, 2=hunching impairs movement, Fur texture: 0=normal, 1=mild to moderate ruffling, 2=severe ruffling, Skin integrity: 0=normal, 1=scaling of paws/tail, 2=obvious areas of denuded skin, Activity: 0=normal, 1=mild to moderately decreased, 2=stationary unless stimulated. Mice were sacrificed when they reached a GVHD score of ≥7 or lived until 42 days. The researcher assessing score was blinded to the treatment of each mouse. Serum was collected to be analyzed for cytokines, the spleen was collected for flow cytometry and samples from the ear, lung, liver and kidney were frozen for digital PCR.

Flow Cytometry

Culture cells or single cell suspensions of spleens from mice were stained with various combinations of the following anti-human antibodies: CD3 APC-Cy7, CD4 PE-Cy7, CD4 eFluor-610, CD8 Alexa Fluor 488, CD8 Brilliant Violet 785, CD19 Brilliant Violet 421, CD34 Brilliant Violet 605, CD39 Brilliant Violet 510, CD25 PerCPCy-5.5, CD127 Brilliant Violet 650, CD73 APC-Cy7, CCR4 PE-Cy7, GITR PE-Cy5, CTLA-4 PE, CD62L AF700 (BioLegend, San Diego, CA). Intracellular transcription factor staining was done using the eBioscience™ FOXP3 Staining Buffer kit (Thermo Fisher Scientific, Waltham, MA) with anti-human FOXP3 PE, anti-human Helios Alexa Fluor 647, anti-Helios Brilliant Violet 421(BioLegend, San Diego, CA). Samples were run on a Becton-Dickson LSRII (Becton-Dickson, Franklin Lakes, NJ) or Attune NxT (Thermo Fisher Scientific, Waltham, MA).

Activation Induced Cell Death Assay

Cells were resuspended at a concentration of $10^6$ cells/mL in complete Aim V media. $2 \times 10^5$ cells from each cell strain were stimulated with plate-bound anti-CD3 (10 µg/mL OKT3; Bio X Cell, West Lebanon, NH) and anti-CD28 (1 µg/mL 9.3; West Lebanon, NH) for 2, 4 or 6 days. Cells were collected at each time point and stained with Zombie Green Fixable Viability Dye and Annexin V PE (Biolegend, San Diego, CA) and assessed for cell death via flow cytometry.

Intracellular Cytokine Staining

Cells were resuspended at a concentration of $10^6$ cells/mL in complete Aim V media. $2 \times 10^5$ cells from each cell strain were stimulated with plate-bound anti-CD3 (10 µg/mL OKT3; Bio X Cell, West Lebanon, N.H.) and anti-CD28 (1 µg/mL 9.3; West Lebanon, NH) for 6 hours in the presence of Golgi Stop (Becton-Dickson, Franklin Lakes, NJ) and Brefeldin A (Sigma Aldrich, St. Louis, MO). Cells were stained with the following extracellular antibodies: anti-human CD4 PE-eFluor610 (Becton-Dickson, Franklin Lakes, NJ), anti-human CD8 Brilliant Violet 785 and anti-human CD19 APC-Cy7 (Biolegend, San Diego, CA). Afterwards, cells were fixed with 2% paraformaldehyde (Sigma Aldrich, St. Louis, MO) and permeabilized with permeabilization buffer from the eBioscience™ FOXP3 Staining Buffer kit (Thermo Fisher Scientific, Waltham, MA) and stained with the following antibodies: anti-human IL-2 FITC, anti-human IFNγ Pacific Blue, anti-human IL-10 Alexa Fluor 647 or anti-human IL-21 Alexa Fluor 647, anti-human IL-4 PE-Cyanine-7, anti-human IL-17A Brilliant Violet 605 (Biolegend, San Diego, CA).

Suppression Assay

Autologous target T cells were labeled with the eBioscience™ Cell Proliferation Dye eFluor670 from (Thermo Fisher Scientific, Waltham, MA) and co-cultured with each eTreg cell strain at a 1:1 ratio with no stimulation or stimulation with anti-CD3 and anti-CD28 coated DYNAL™ Dynabeads™, Human T-Activator (Thermo Fisher Scientific, Waltham, MA.) at 1:10 bead: target cell ratio. The final concentration of cells was at $5 \times 10^5$ cells/ml. After 96 hours, target cell proliferation was assayed via flow cytometry. Cells were also stained with Zombie Green Fixable Viability Die and anti-human CD4 PE-Cy7, anti-human CD8 PE, anti-human CD19 APC-Cy7, anti-human CD25 PerCPCy5.5 (Biolegend, San Diego, CA).

RNA Sequencing

FOXP3+, FOXP3+Hel-FL, and FOXP3+Hel-Δ3B Tregs were generated from PBMCs isolated from three different healthy human donors. Cells were collected Day 5 after the second transduction and stained with anti-human CD4 Pacific Blue and anti-CD8 Alexa Fluor 488 (Biolegend, San Diego). CD4+ and CD8+ cells were isolated via flow cytometry assisted cell sorting on a BD FACS Aria III. RNA was isolated using a Qiagen RNeasy Mini Kit (Qiagen, Germany). TruSeq stranded mRNA sequencing libraries were performed using the Illumina TruSeq Sample preparation kits and NuGEN sample preparation kit and paired end RNA sequencing data was generated using an Illumina NovaSeq 6000 Sequencing System (Illumina, San Diego, CA).

Adaptor removal was performed by cutadapt. After adaptor removal, QC was done with fastqc (bioinformatics.babraham.ac.uk/projects/fastqc). Samples were then aligned to human genome (hg38) with RSEM and bowtie2, after which transcript counts were obtained. Using the Bioconductor package "edgeR", we first normalized the data by library size and then filtered out genes that have low expression. Genes were retained if their cpm (count per million) value was larger than 1 for at least two samples out of the 18 total considered in this study. After filtering low/non-expressed genes, 13,955 remained for subsequent statistical analysis. Next, we performed a series of differential expression analyses, comparing gene expression between different pairs of cell types. There were a total of six comparisons being performed: FOXP3+CD4+ vs FOXP3+ Hel-FL CD4+, FOXP3+CD4+ vs FOXP3+ Hel-Δ3B CD4+, FOXP3+CD8+ vs FOXP3+ Hel-FL CD8+, FOXP3+CD8+ vs FOXP3+Hel-Δ3B CD8+, FOXP3+ Helios-FL CD4+ vs FOXP3+ Hel-Δ3B CD4+, FOXP3+ Helios-FL CD8+ vs FOXP3+ Hel-Δ3B CD8+. For each comparison, a volcano plot depicting the −log(p-value) as a function of log-fold change in expression, was generated.

We further filtered genes with differential expression by taking 2,000 genes with the lowest false discovery rate (FDR). We then restricted this gene list to genes with an expression change that was the same direction in all 3 donors. We made these filtered lists for each donor and comparison and used the CPMs to carry out gene set enrichment analysis (GSEA) with the GSEA v3.0 software from the Broad Institute. We looked at enrichment in the KEGG pathway gene sets (c2.cp.kegg.v6.2.symbols.gmt) to identify and visualized significantly enriched pathways in different eTreg cell strain comparisons.

In order to examine the Treg related gene expression, we generated heatmaps based the cpm value from count data. More specifically, we compiled two lists of Treg genes based on published comparisons of Tconvs vs Tregs referred to as the "up gene list" and the "down gene list". On the basis of the differential expression results generated for gene expression comparisons of specific cell types, we first subset the genes that had a nominal, uncorrected p value <0.05 based on either up or down Treg gene list. Then, we filtered genes that only showed expected expression patterns, that is, all three subjects were up regulated in an up_gene comparison or vice versa, so that we kept up regulated genes in an up_gene heatmaps and kept down regulated genes in down gene heatmaps. Further, we merged two comparisons of heatmaps into one. The two heatmaps merged have differences in the type of cell strain and share the same cell type (CD4 or CD8) and gene list (up or down gene list). The merged heatmap contains all genes in either of the two comparisons. For each cell in the heatmap, we calculated the difference of cpm values between two strains of cell for one subject and divided by average cpm value of that gene in all three subjects.

Data/Statistical Analysis

Data were collected and analyzed with GraphPad Prism 7 (GraphPad Software, [La Jolla, CA]). Data reported at each time point for GVHD score and weight loss were an average of the scores and weights of the mice left alive and the last scores and weights of any deceased mice in each group. Mann-Whitney tests were done to compare GVHD scores at each time point. The log-rank (Mantel-Cox) test was used for analysis of Kaplan-Meier curves. Differences between groups were compared via Mann Whitney tests. Differences between groups with data normalized to a control were compared using the Wilcoxon test. p≤0.05 was considered to be significant. Results show mean±standard error mean unless otherwise indicated.

Results

Dual Retroviral Transduction can Convey FOXP3 and Helios Expression in Human T Cells In order to generate human eTregs that express both FOXP3 and Helios, we developed a dual, sequential transduction protocol. In initial work, transduction of human T cells with a vector that contained both Helios and FOXP3 resulted in downregulation of FOXP3 expression and the truncated ΔCD19 transduction marker. There were multiple Helios binding sites present in the cDNA construct containing Helios and FOXP3 (data not shown) and Helios can downregulate gene expression upon promoter binding. Notably, switching the order of FOXP3 and Helios on the same vector did not change expression levels. FOXP3 expression was still reduced when included in Helios-expressing vectors.

With the dual, sequential transduction protocol, Helios-overexpressing cells had high expression of the truncated ΔCD34 transduction marker until about four days post-transduction (data not shown). This is likely due to the kinetics of Helios-mediated suppression of gene expression. Thus, it was possible to use magnetic bead separation to purify Helios+ ΔCD34+ cells two days post-transduction followed by removal of the magnetic beads. Then, we transduced these cells with the SFG-FOXP3-ΔCD19 retroviral vector and repeated magnetic bead purification to obtain human eTregs with ectopic overexpression of Helios (SEQ ID NO:2 or 6) and FOXP3 (SEQ ID NO:4). FIG. 1A and FIG. 1B.

Figure 2B:
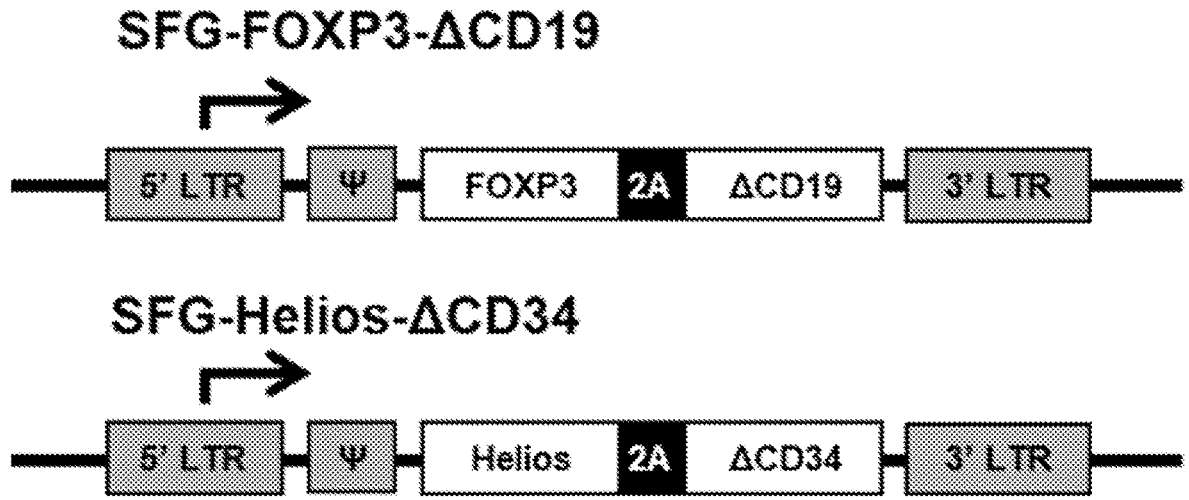
FIG. 2B is a graph of the GMFI of FOXP3 and Helios in the CD4+ eTreg population positive for the protein of interest, eTregs were assessed via intracellular transcription factor staining and flow cytometry, N=8-9 and 5 different donors.
Figure 2B:
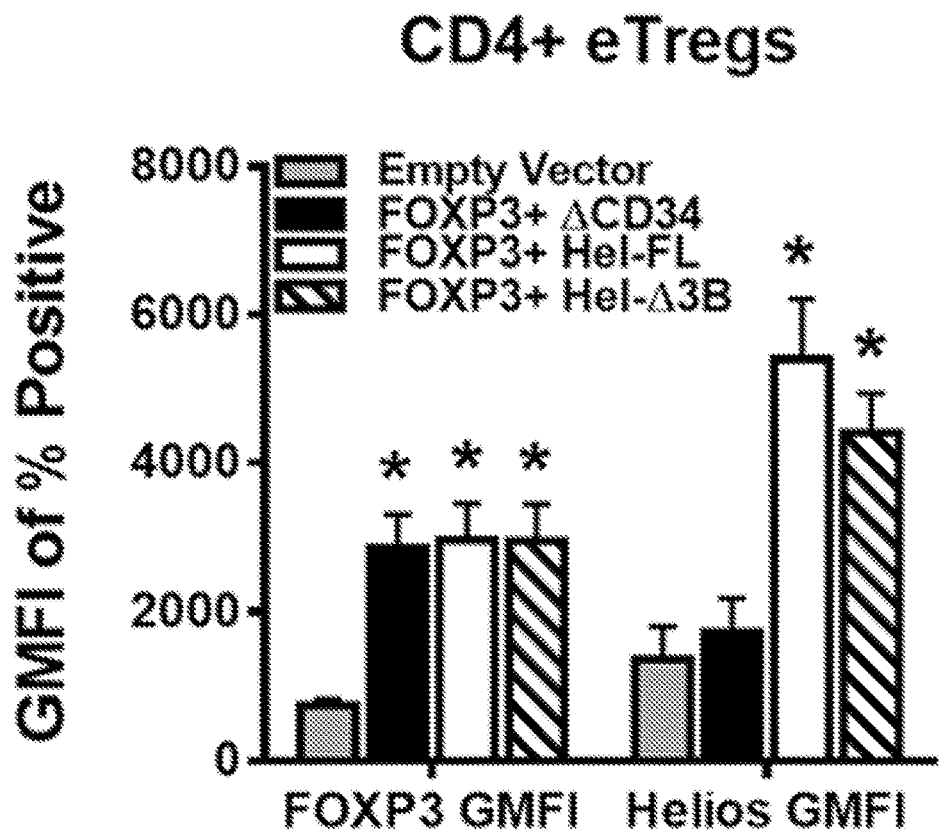
Figure 2C:
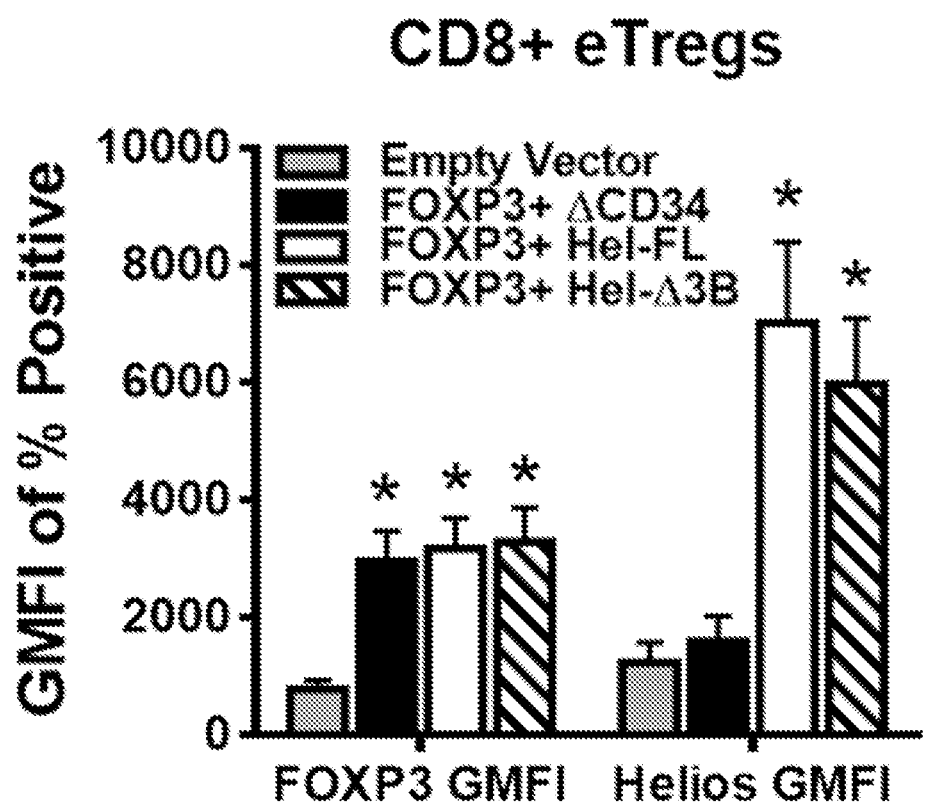
FIG. 2C is a graph of the GMFI of FOXP3 and Helios in the CD8+ eTreg population positive for the protein of interest, eTregs were assessed via intracellular transcription factor staining and flow cytometry, N=8-9 and 5 different donors.
Figure 2D:
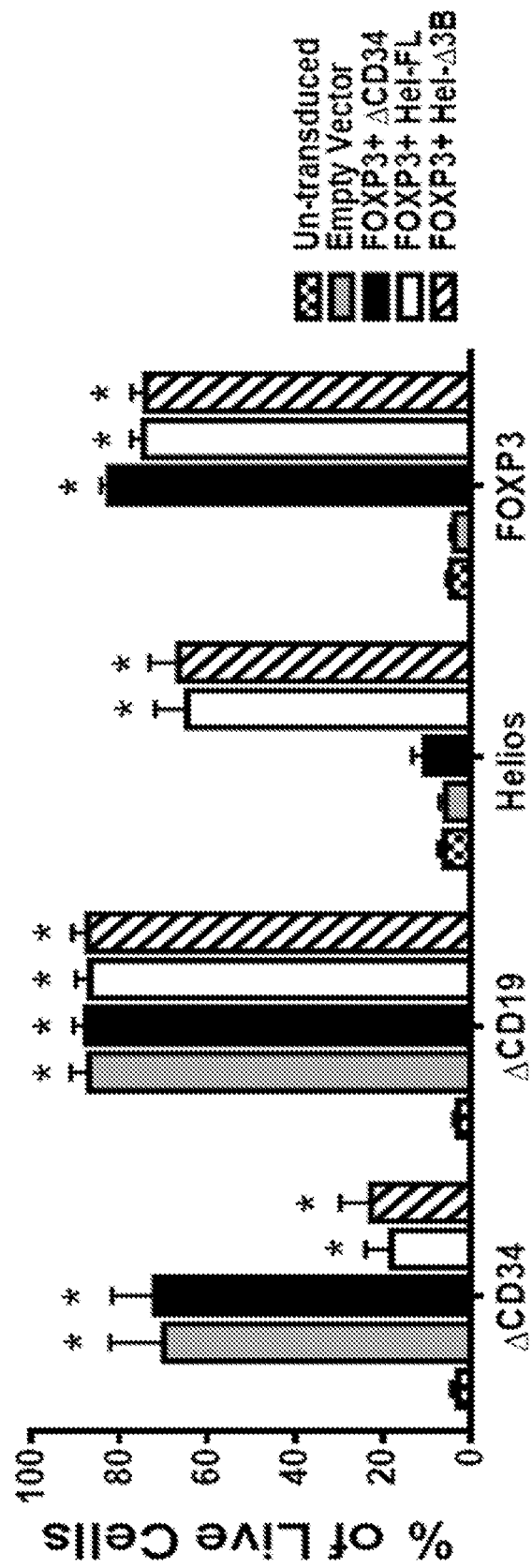
FIG. 2D is a graph of the summary of the percentage of eTregs positive for ΔCD34, ΔCD19, FOXP3, and Helios of total live cells, after assessment of protein expression via surface and intracellular transcription factor staining and flow cytometry. Cells were assessed after the second transduction and magnetic bead purification for CD19.
Figure 2E:
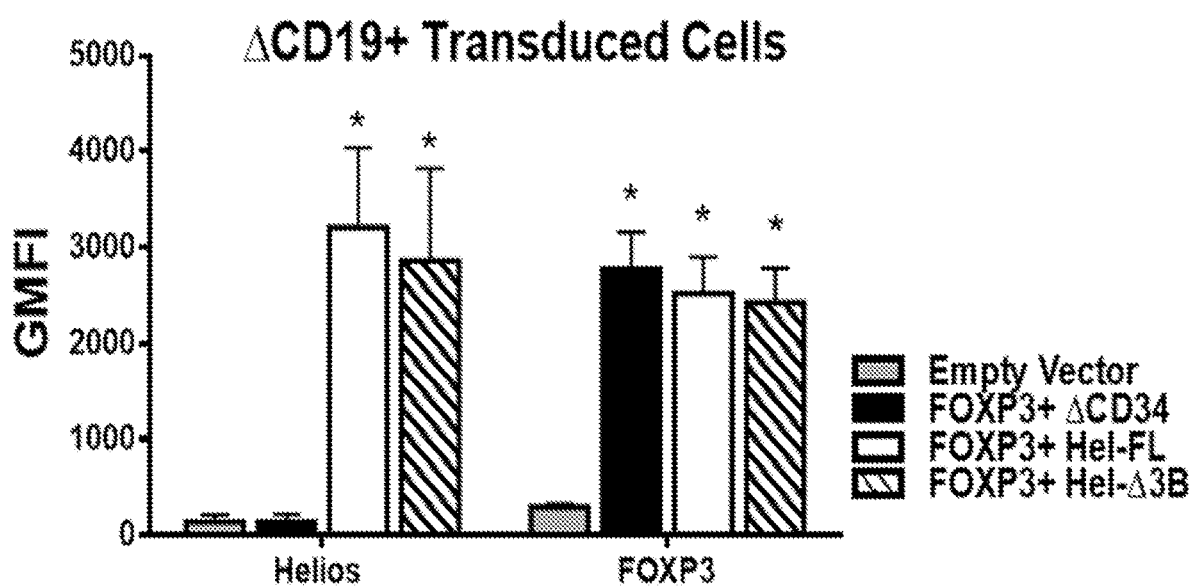
FIG. 2E is a graph of the GMFI of FOXP3 and Helios in transduced cells gated on ΔCD19 expression.
Figure 2F:
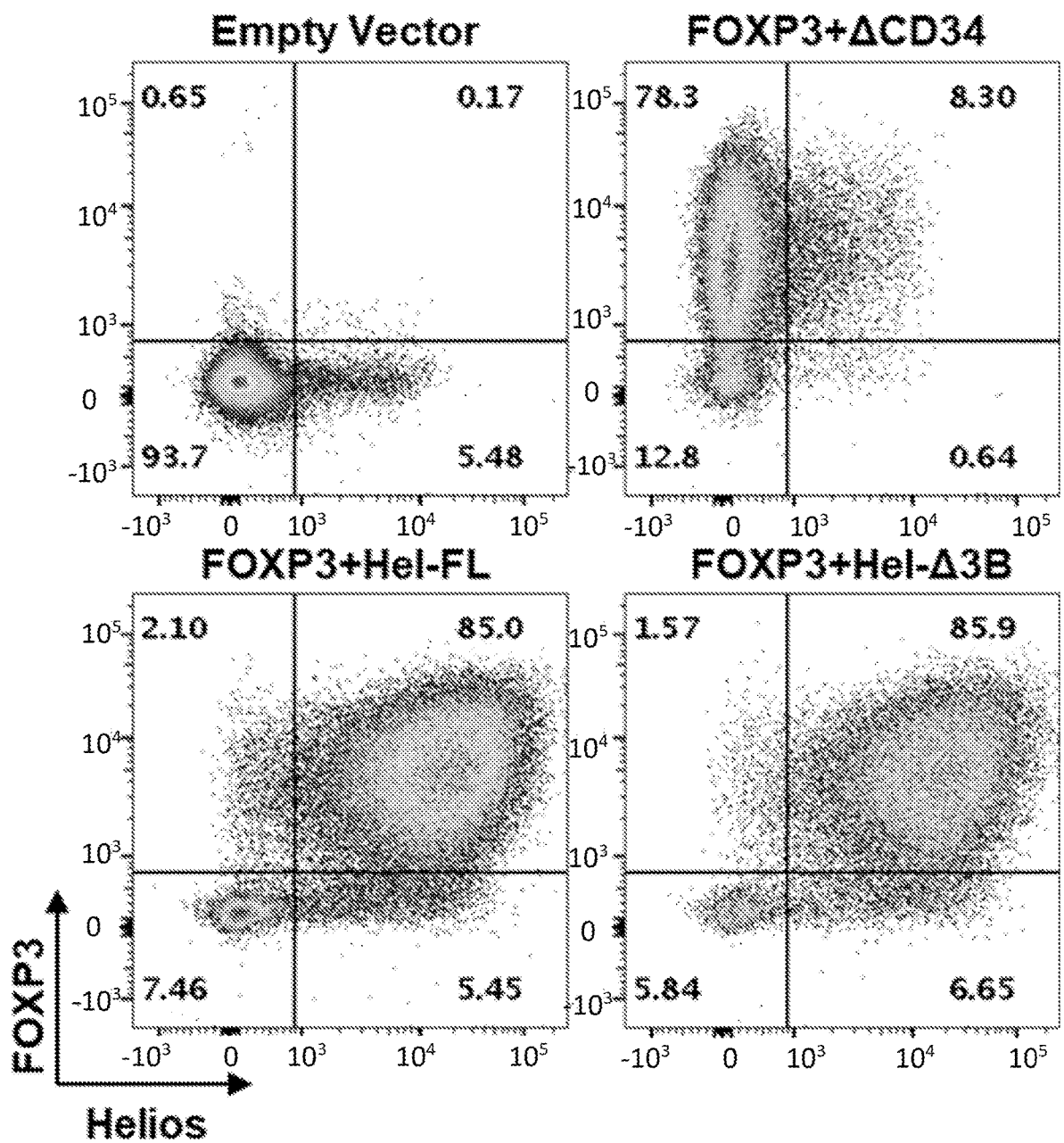
FIG. 2F representative figures of ΔCD34 and ΔCD19 expression following the second transduction and CD19 bead purification.
Figure 2G:
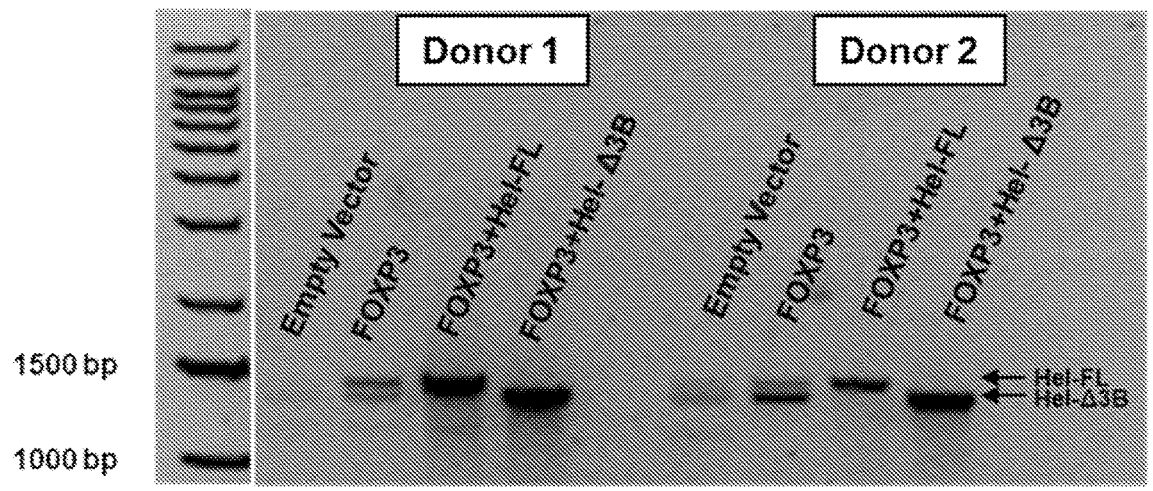
FIG. 2G is a representative figure of Helios mRNA expression assessed via real-time polymerase chain reaction (RT-PCR) and visualized via gel electrophoresis.
Figure 2H:
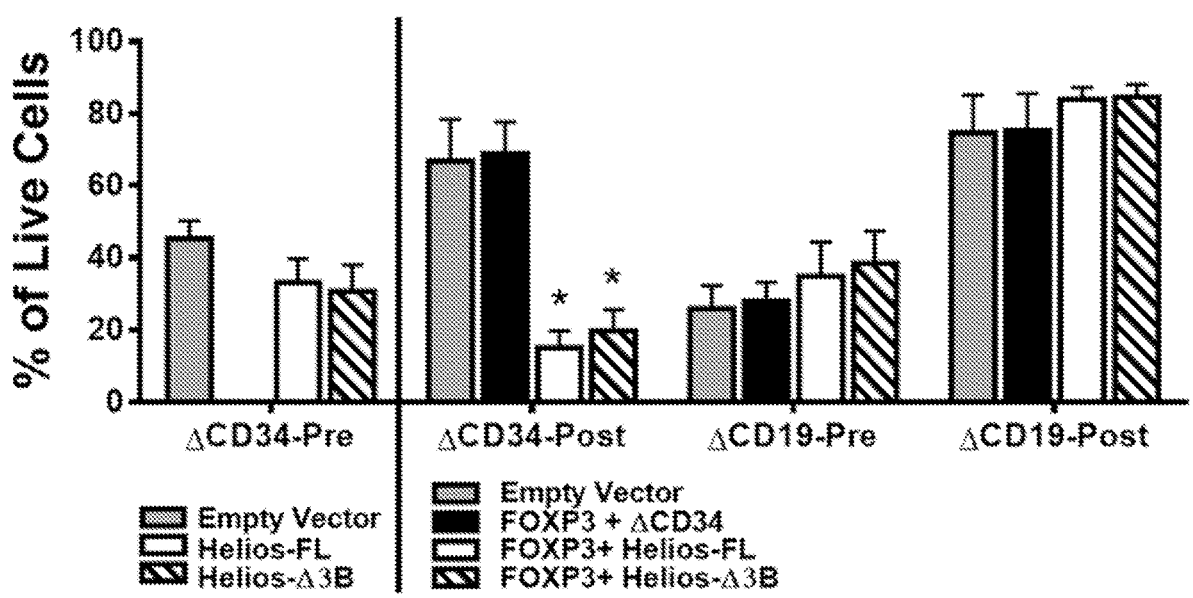
FIG. 2H is a graph if the results of expression of transduction markers ΔCD34 and ΔCD19 before CD34 and CD19 magnetic bead purification (Pre) and after CD19 bead purification (Post).

In contrast to previously published eTreg studies, we transduced total human T cells rather than purified CD4+ T cells. This work demonstrates that co-expression of FOXP3 and Helios conveys immunosuppressive function to human CD8+ T cells. Additionally, transduction of total T cells reduces purification steps required to generate these eTregs in a clinical setting. Both CD4+ and CD8+ T cells within the total T cell population expressed high levels of Helios and FOXP3 (FIG. 2B-C). We also chose to investigate the two different endogenous splice variants of Helios, Hel-FL and Hel-Δ3B, in eTreg function. We transduced either Hel-FL or Hel-Δ3B with a truncated CD34 marker (ΔCD34) and FOXP3 with a truncated CD19 marker (ΔCD19) into T cells purified from peripheral blood to obtain a mixed population of CD4+ and CD8+ T cells that highly expressed both Helios and FOXP3 (FIG. 2D-E). Although ΔCD34 expression was downregulated in transduced cells with Helios, there was still higher expression of Helios compared with an empty vector control (FIG. 2F). Further, RT-PCR gel electrophoresis (FIG. 2G) showed that the overexpressed full length isoform of Helios was the predominant splice variant of Helios expressed in each eTreg compared to the expression of both full length and the shorter isoform of Helios in FOXP3+ eTregs. The expression of transduction markers ΔCD34 and ΔCD19 before CD34 and CD19 magnetic bead purification (Pre) and after CD19 bead purification (Post) was also assessed. Marker expression was assessed via flow cytometry and plotted as percent of total eTregs positive for the indicated marker (FIG. 2H). Values are expressed with % positive of non-transduced control subtracted out. n=3-7 and 5 different donors. Some experiments were performed with two separated cell transductions with the same donor cells and some groups did not have all eTreg cell types. * p<0.05 compared to empty vector control based on one-tailed Mann-Whitney test.

Figure 3:
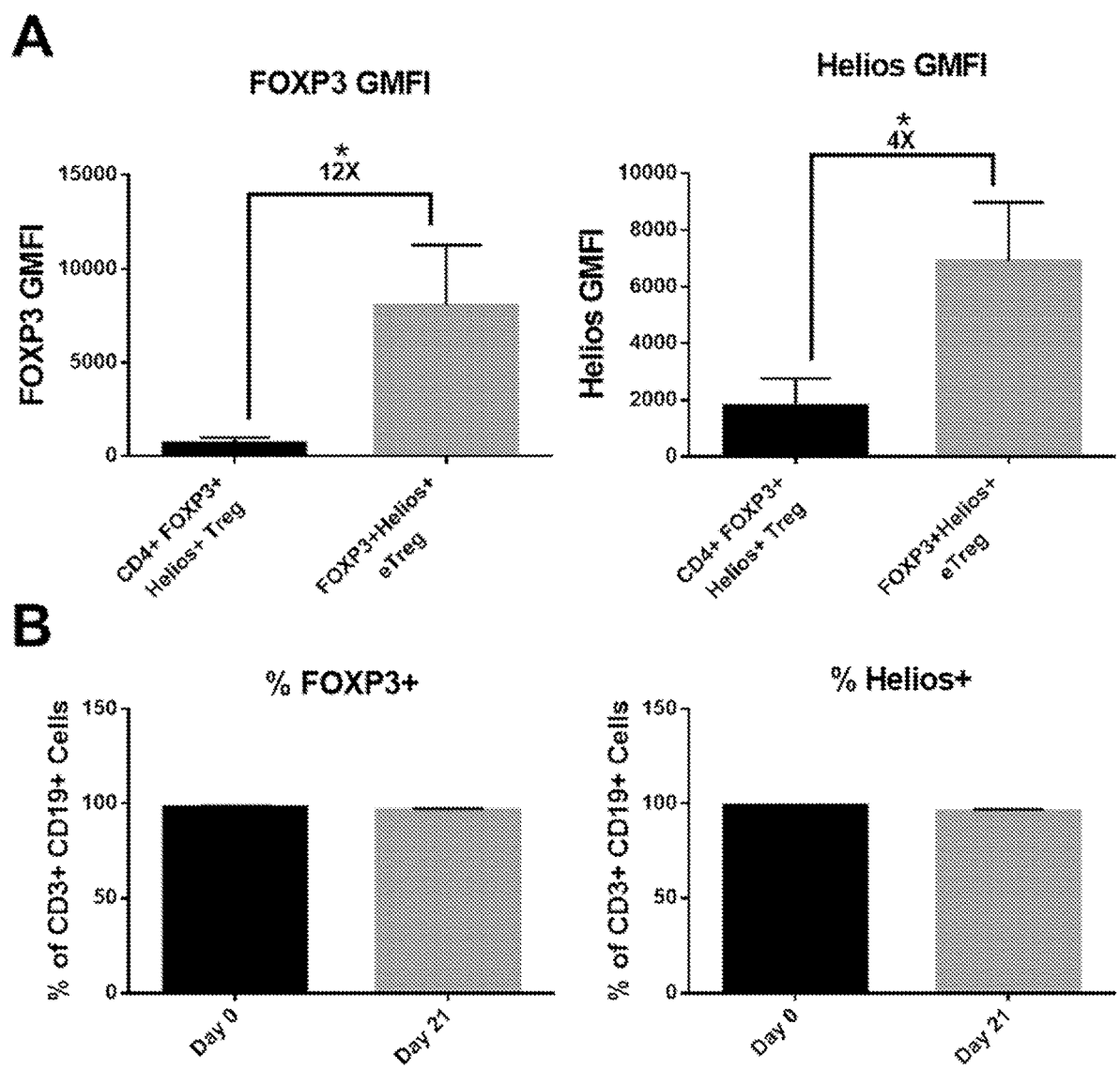
FIG. 3 shows that FOXP3+Helios+ eTregs maintain high expression of FOXP3 and Helios in vitro and in vivo. A) CD4+ FOXP3+ Helios+ Tregs from peripheral blood and FOXP3+Helios+ (aka FOXP3+Hel-FL) eTregs were assessed via intracellular transcription factor staining and flow cytometry. Graphs summarize the GMFI of FOXP3 and Helios, n=4 and 4 different donors. B) CD3+ CD19+ transduced FOXP3+Helios+ eTregs were isolated from mice treated with eTregs 21 days post transduction and 12 days post injection. % FOXP3+ and % Helios+ were assessed via intracellular transcription factor staining and flow cytometry.

FOXP3+Helios+ eTregs expressed 12 times more FOXP3 (SEQ ID NO:4) and 4 times more Helios (SEQ ID NO:2 or 6) than endogenous CD4+ FOXP3+ Helios+ Tregs from fresh PBMCs (FIG. 3A). About 98% of FOXP3+ Helios+ cells retained high FOXP3 and Helios expression 21 days post-transduction and 12 days in vivo in mice (FIG. 3B). Thus, we generated eTregs strains that overexpress FOXP3, FOXP3+Hel-FL and FOXP3+Hel-Δ3B and an empty vector control with just ΔCD19+ΔCD34.

FOXP3+Hel-FL eTregs Delay Disease In Vivo in a xeno-GVHD Model

Figure 4:
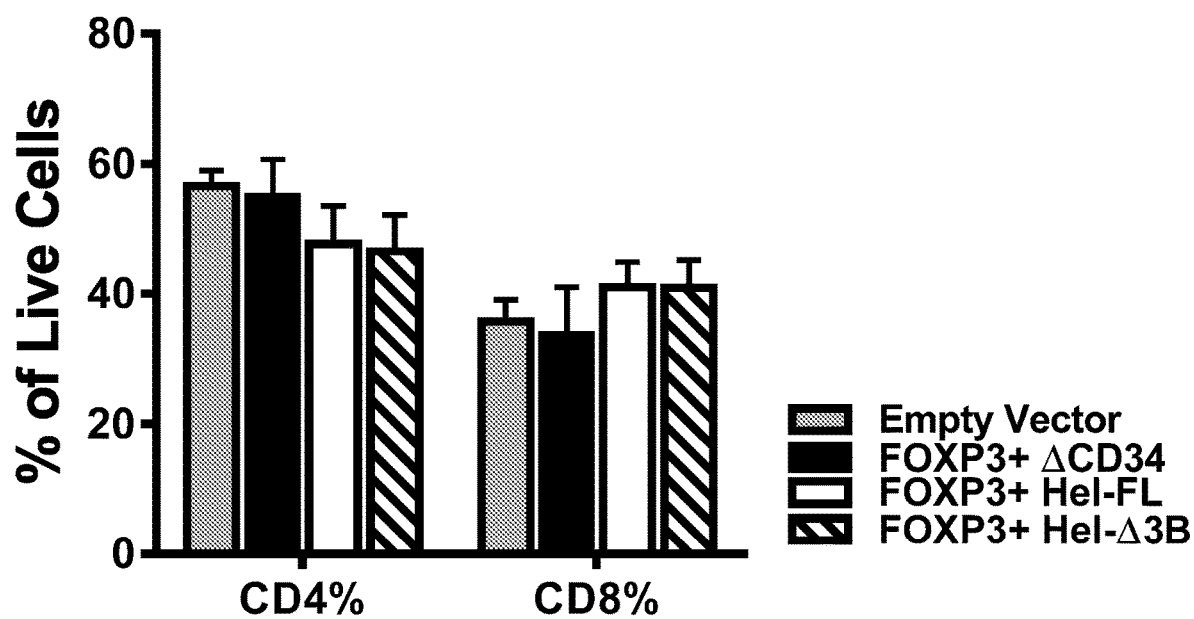
FIG. 4 is a graph showing relative ratio of CD4+ and CD8+ eTregs used for the xenoGVHD experiments. Prior to injection into mice, empty vector control cells (n=6), FOXP3 eTreg (n=6), FOXP3+HEL-FL eTregs (n=7) and FOXP3+ Hel-Δ3B eTregs (n=7) were assessed for surface expression of CD4 and CD8 expression via flow cytometry. T cells from 4 different donors were used. Comparison of all groups was performed using one-tailed Mann-Whitney test p≤0.05
Figure 5:
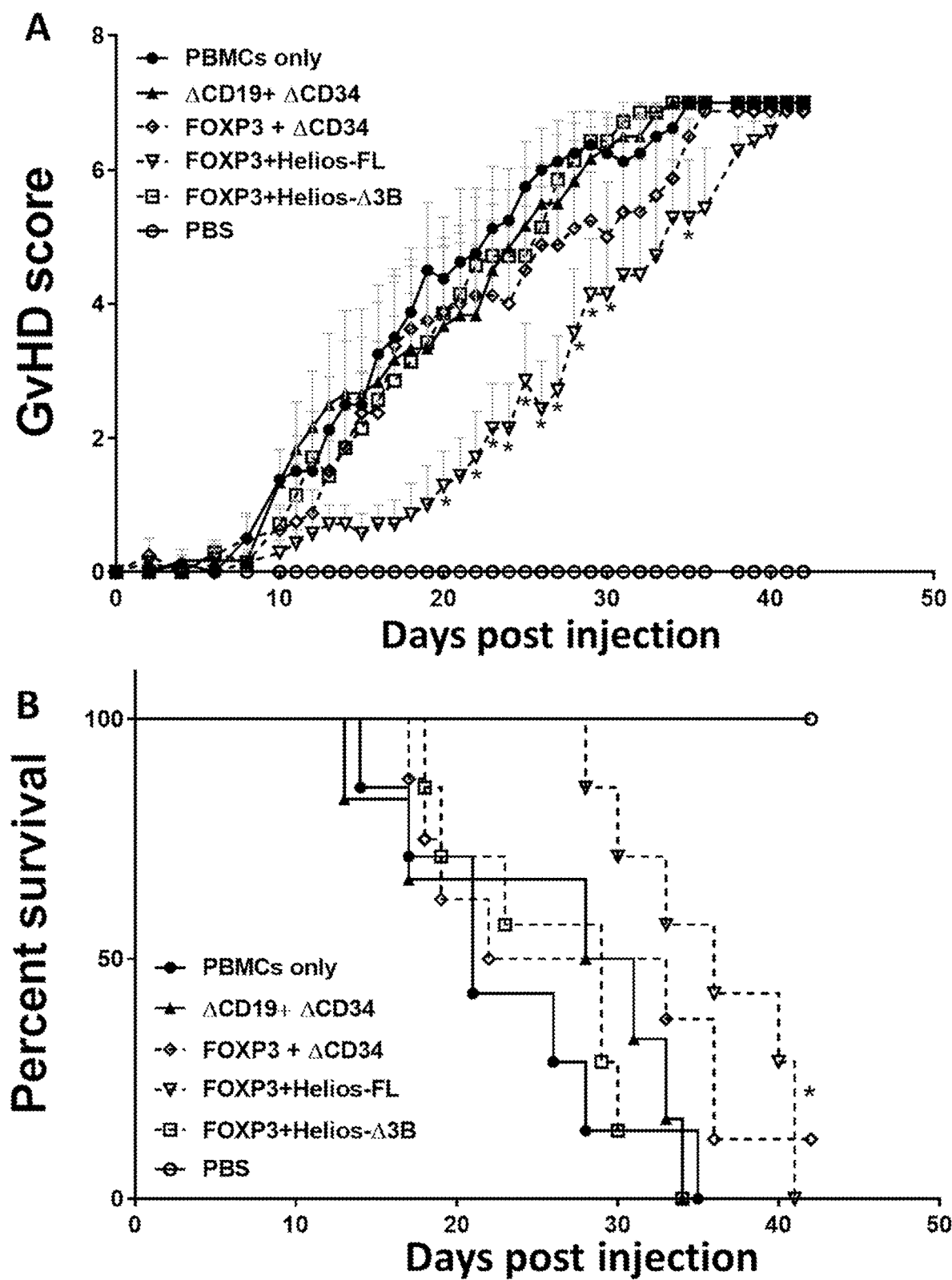
FIG. 5 shows that FOXP3+Hel-FL eTregs delay disease progression in a xenogeneic GVHD murine model. 8-12 week old NSG mice were sub-lethally irradiated. The next day, the mice were injected retro-orbitally with $10^7$ human PBMCs alone or with $5 \times 10^6$ empty vector control cells or eTregs. A) GVHD score was monitored until day of sacrifice. *=p<0.05 compared to PBMCs only based on a one-tailed Mann-Whitney test for each time point. A) Kaplan-Meier curve of survival. Death was marked when GVHD score was ≥7. *=p<0.05 compared to PBMCs only as determined by log-rank test. Treatment of mice with FOXP3+Helios-FL eTregs delays disease progression in a xenogeneic GVHD model while FOXP3+Helios-Δ3B eTregs do not delay disease.

In order to assess the suppressive capacity of each eTreg cell strain in vivo, we utilized a xenogeneic Graft Versus Host disease (xenoGVHD) model in which sublethally irradiated NSG mice were intravenously injected with human PBMCs without or with each eTreg cell strain or empty vector control cells. Injected eTregs had comparable CD4: CD8 ratios across all groups (FIG. 4). Mice treated with FOXP3+Hel-FL (aka FOXP3+Helios+) eTregs had significantly delayed GVHD progression compared to mice with PBMCs only (FIG. 5A). Additionally, FOXP3+Hel-FL eTregs significantly improved survival based on a log-rank test compared to mice with PBMCs only (FIG. 5B). Mice treated with FOXP3+Hel-FL eTregs had a median survival of 36 days compared to mice with PBMCs only, which had a median survival of 21 days. Interestingly, mice treated with FOXP3 or FOXP3+Hel-Δ3B eTregs did not significantly delay GVHD, with a median survivals of 27.5 days and 29 days respectively.

Next, irradiated NSG mice were injected with human PBMCs without or with each eTreg cell strain or empty vector control cells and euthanized at an early timepoint of 12 days to assess mice at different stages of disease. As observed in the long term xenoGVHD experiment, mice treated with FOXP3+Hel-FL had the lowest average GVHD score at this time point with a mean score of 0.6±0.4 compared to 2.8±0.86 for mice injected with PBMCs only (data not shown). Spleens from each mouse were processed into a single cell suspension and analyzed via flow cytometry. Even though all three eTreg cell strains conveyed these immunosuppressive effects in the spleen, FOXP3+Hel-FL eTregs were still the most effective at delaying GVHD. Serum cytokines from these early time point mice were analyzed via cytometric bead array and revealed many differences between the treatment groups. Compared to the empty vector control treated mice, all three eTreg strains decreased multiple pro-inflammatory proteins in the serum, including IL-4, TNFα, sFas, sFasL, granzymes A and B, perforin and granylysin. Interestingly, both FOXP3+Hel-FL and FOXP3+Hel-Δ3B eTregs decreased IL-6 in the serum and FOXP3 and FOXP3+Hel-FL eTregs decreased IFNγ. Thus, FOXP3+Hel-FL eTregs could effectively delay disease and improve survival in a xenoGVHD model, while FOXP3 and FOXP3+Hel-Δ3B eTregs could not, but the mechanism was unclear.

Hel-FL and Hel-Δ3B Co-Expression with FOXP3 Differentially Regulate CD4+ and CD8+ eTreg Suppression The ability of each eTreg strain to suppress T cell proliferation was also tested in vitro. In addition to total eTregs, CD4+ and CD8+ T cells were purified via magnetic bead separation and assayed separately. Freshly isolated human T cells were labeled with a proliferation dye and co-cultured with each eTreg cell strain, total, CD4+ or CD8+, at a 1:1 ratio. Cells were stimulated with anti-CD3 and anti-CD28 coated beads for four days before being assayed via flow cytometry. In agreement with the in vivo data, FOXP3+ Hel-FL total eTregs were the most effective at suppression compared with FOXP3+ and FOXP3+ Hel-Δ3B total eTregs, with a mean percent suppression of 46.21±12.54% vs 16.47±4.526% vs 21.67±8.658%, respectively (FIG. 6A). The same was true for CD4+ eTregs with FOXP3+ Hel-FL suppressing proliferation at a mean of 40.82±10.36% compared to 21.19±8.968% and 19.06±8.968% suppression by FOXP3+ and FOXP3+Hel-Δ3B CD4+ eTregs respectively (FIG. 6A). However, both FOXP+ Hel-FL and FOXP3+Hel-Δ3B overexpression in CD8+ eTregs was able to more effectively mediate suppression of T cell proliferation with a percent suppression of 45.85±7.794% and 48.30±10.88%, respectively, compared to FOXP3+ alone, which had a percent suppression of 21.68±11.01% (FIG. 6A). In conclusion, both CD4+ and CD8+ T cells transduced with FOXP3 and Hel-FL were the most effective at suppressing T cells in vitro compared to FOXP3 alone and FOXP3+ Hel-Δ3B. Both FOXP3+ Hel-FL and FOXP3+ Hel-Δ3B CD8+ eTregs were more effective than FOXP3+CD8+ eTregs alone at suppressing T cell proliferation. See also FIG. 6B.

Ectopic Overexpression of FOXP3 with and without Helios Reduces T Cell Survival In Vitro and In Vivo Previous studies reported that overexpression of FOXP3 in primary human T cells reduced proliferation in vitro, and ectopic expression of Helios in Jurkat cells, a human T cell line, also resulted in reduced survival in vitro. To determine whether the greater suppressive function of the Helios-expressing eTregs was due to enhanced eTreg survival, we compared the proliferation and survival of the eTreg cell strains in vitro. We observed that overexpression of FOXP3 in human T cells reduced proliferation over time and the addition of either isoform of Helios with FOXP3 expression further reduced proliferation (FIG. 7A). There was also an increase in activation-induced cell death in all three eTreg cell strains, with more death observed in both the Helios-expressing eTregs (FIG. 7B and FIG. 7C). This decreased survival in all eTreg strains was observed in vivo in the xenoGVHD mice euthanized at an early time point. Human T cells that are transduced with FOXP3 without or with either isoform of Helios have reduced proliferation compared to T cells transduced with an empty vector in vitro. However, overexpressing Hel-FL and Hel-Δ3B alone did not affect T cell proliferation. Average cell counts of eTregs growing in IL-2 supplemented media for 2 days starting on Day 3 post-transduction with Hel-FL and Hel-Δ3B alone did not show a significant impact on T cell proliferation (n=5 for each group from 4 different donors. *p≤0.05 in each comparison based on a one-tailed Wilcoxon test for each time point).

FOXP3 Overexpression without and with Helios Affects Human T Cell Expression of Treg Markers and Cytokine Production Overexpression of FOXP3 in primary human T cells has been shown to mediate expression of Treg markers; specifically, increased expression of CD25, GITR, CTLA-4 and decreased expression of CD127. We used multi-parameter flow cytometry to analyze expression of the following Treg markers on all three eTreg cell strains: CD25, CD127, CD73, CD39, CTLA-4, GITR, CCR4 and CD62L. Human T cell surface expression of CD39, CTLA-4, GITR and CD62L was not significantly affected by FOXP3 overexpression without and with Helios compared to empty vector control cells (data not shown). All three eTreg cell strains had significantly decreased CD127 expression on CD4+ eTregs and increased CCR4 expression on both CD4+ and CD8 eTregs (FIG. 8A). CD25 was significantly increased for both CD4+ and CD8+ eTregs with FOXP3+Hel-FL and only CD8+ eTregs with FOXP3+Hel-Δ3B.

Cytokine production by each eTreg cell strain was assessed via stimulation with plate bound anti-CD3 and anti-CD28 in the presence of Golgi transport inhibitors, Brefeldin A and monensin (FIG. 8B). In agreement with previously published data, FOXP3 overexpression reduced production of IL-2, IFNγ and IL-4 by CD4+ human T cells. FOXP3+ Hel-FL and FOXP3+ Hel-Δ3B eTregs also had a similar reduction in IL-2, IFNγ and IL-4 production by CD4+ T cells. FOXP3 ectopic expression with and without either isoform of Helios also reduced IL-2 production by CD8+. In summary, transduced human T cells expressing FOXP3+, FOXP3+ Hel-FL or FOXP3+Hel-Δ3B upregulate certain Treg surface markers and have reduced pro-inflammatory cytokine secretion.

Hel-FL and Hel-Δ3B Co-Expression with FOXP3 have Different Effects on the Enrichment of Genes in Cellular Pathways and Treg Transcriptional Signature Despite the differences in immunosuppression observed between FOXP3+ Hel-FL compared to FOXP3+ eTregs and FOXP3+Hel-Δ3B in vitro and in vivo, the strains unexpectedly had similar proliferation and survival, Treg markers, and cytokine secretion. Thus, we utilized RNA sequencing (RNA Seq) to determine if there were any differences between these eTreg cell strains at a transcriptional level. Three different healthy donor T cells were transduced with cDNA encoding FOXP3+, FOXP3+ Hel-FL, and FOXP3+ Hel-Δ3B. Then CD4+ and CD8+ T cells from each eTreg cell strain were separated via fluorescence-activated cell sorting (FACS). RNA was extracted from each sample and analyzed via RNA Seq.

Comparison of gene expression fold change revealed that adding either isoform of Helios to FOXP3-overexpressing CD4+ and CD8+ eTregs did change gene expression compared to FOXP3 alone (FIG. 9A). We then carried out Gene Set Enrichment Analysis (GSEA) pathway analysis using GSEA v3.0 from the Broad Institute and the Kyoto Encyclopedia of Genes and Genomes (KEGG) database. Both FOXP3+Hel-FL and FOXP3+Hel-Δ3B CD4+ and CD8+ eTregs had changes in pathway enrichment when compared to FOXP3 alone (FIG. 9B). Notably, there were more increases in pathway enrichment in the FOXP3+Hel-Δ3B vs FOXP3 comparison compared to the FOXP3+Hel-FL vs FOXP3 comparison in both CD4+ and CD8+ eTregs (FIG. 9B).

Figure 10B:
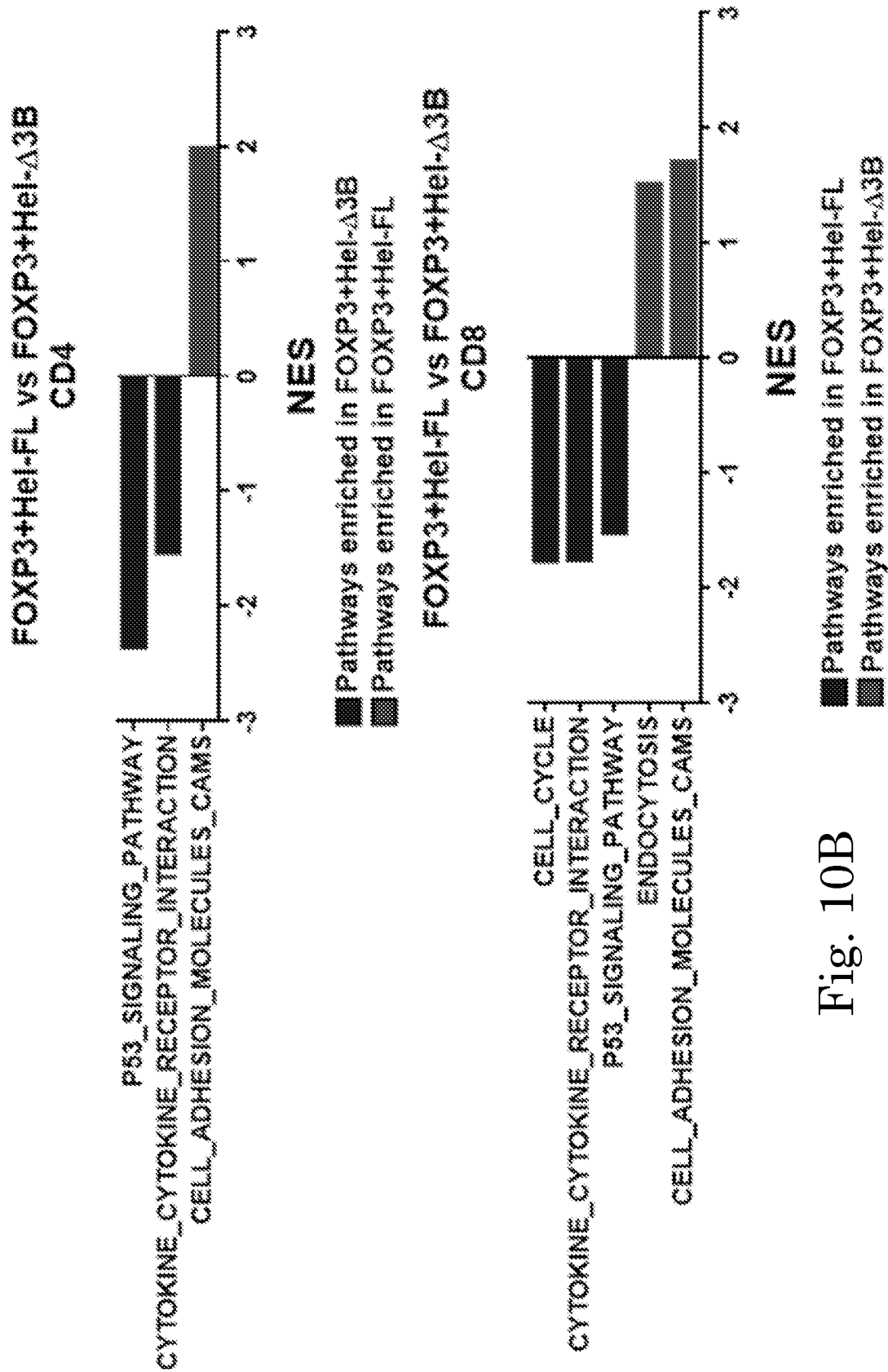

There were fewer differences in gene expression when comparing FOXP3+ Hel-FL and FOXP3+Hel-Δ3B eTregs (FIG. 10A). Despite the small differences in gene expression, FOXP3+Hel-FL had different enriched KEGG pathways when compared to FOXP3+ Hel-Δ3B in both CD4+ and CD8+ eTregs (FIG. 10B). Three of these enriched pathways were the same in CD4+ and CD8+FOXP3+Hel-FL eTregs: p53 signaling pathway, cell adhesion molecules and cytokine-cytokine receptor interaction. Interestingly, some of the genes that were changed in these two common pathways did differ between CD4+ and CD8+ eTregs (FIG. 11A-11C).

In order to determine changes in Treg-related genes in the eTreg cell strains, we generated lists of genes based on published comparisons of Tconvs vs Tregs. We compiled genes that were either up-regulated or down-regulated in Tregs compared to Tconvs, named the "TREG UP" and "TREG DOWN" gene lists respectively. We then analyzed whether adding Hel-FL or Hel-Δ3B to FOXP3-overexpressing eTregs led to up-regulation of the TREG UP genes and down-regulation of the TREG DOWN genes, indicating an increase in Treg signature. The results are shown in FIG. 12A-12C. Interestingly, FOXP3+Hel-Δ3B had more genes in the Treg signature that were differentially expressed than FOXP3+Hel-FL when compared to FOXP3. This was true for both CD4+ and CD8+ eTregs. Additionally, eTregs did change expression of Treg genes to make them more "Treg-like" when compared to FOXP3 in both CD4+ and CD8+ eTregs. Since all the Treg genes were not changed when comparing these two eTregs, FOXP3+Helios+ Tregs still have differences compared to endogenous Tregs (Table 2).

TABLE 2

FOXP3+ Helios+ eTregs do not change all Treg-related genes when compared to FOXP3+ eTregs. Raw cpms for a small subset of Treg signature genes that are unchanged when comparing FOXP3+ and FOXP3+ Helios+ in A) CD4+ eTregs and B) CD8+ eTregs.

| NAME | FOXP3 CPMs | | | FOXP3+ Helios CPMs | | |
|---|---|---|---|---|---|---|
| | FOX1 | FOX2 | FOX3 | FL1 | FL2 | FL3 |
| CD4+ | | | | | | |
| AARS | 106.0465 | 110.5766 | 100.9727 | 88.72041 | 107.4717 | 103.4746 |
| AARSD1 | 16.80381 | 16.07709 | 15.20292 | 14.06405 | 15.58886 | 15.26378 |
| ABCC1 | 142.1452 | 128.1066 | 148.2249 | 151.1072 | 131.987 | 133.688 |
| ABCG2 | 4.908611 | 2.474825 | 1.571418 | 2.733597 | 1.295662 | 1.090737 |
| ABHD1 | 0.422004 | 0.378098 | 0.694713 | 0.916362 | 0.480759 | 1.232897 |
| ABHD2 | 142.9255 | 142.7882 | 148.8191 | 151.7189 | 155.1016 | 137.4703 |
| ABHD6 | 6.203939 | 4.193454 | 7.491642 | 6.651753 | 4.637105 | 6.035413 |
| ABT1 | 53.75611 | 49.04967 | 45.82692 | 53.03178 | 51.5196 | 47.5925 |
| ACOT9 | 20.70105 | 15.73405 | 15.72149 | 22.02338 | 17.31891 | 20.52295 |
| ACSL6 | 58.50588 | 63.55249 | 112.1678 | 75.40081 | 54.99368 | 75.4852 |
| ACSM3 | 1.872772 | 2.318774 | 2.526693 | 3.115389 | 2.314461 | 2.319998 |
| ACTN4 | 657.0289 | 609.4911 | 653.0552 | 562.8443 | 574.1572 | 487.1843 |
| ADAM32 | 0.511314 | 0.830785 | 1.285639 | 1.282664 | 1.03312 | 1.052561 |
| ADAMTS10 | 2.590656 | 1.718629 | 5.993314 | 9.081617 | 4.50072 | 17.48815 |
| ADAMTSL3 | 0.815375 | 1.181385 | 1.753044 | 1.291473 | 0.612712 | 0.870045 |
| CD8+ | | | | | | |
| AARS | 93.87578 | 106.4882 | 114.5799 | 95.29567 | 109.727 | 109.2899 |
| AARSD1 | 15.81395 | 16.36825 | 15.16144 | 15.75138 | 15.58327 | 14.38107 |
| ABCC1 | 140.8865 | 134.8142 | 132.2136 | 156.352 | 131.9862 | 132.7824 |
| ABCG2 | 3.350105 | 2.638386 | 1.082767 | 2.226685 | 1.386639 | 0.640996 |
| ABHD1 | 0.327728 | 0.329798 | 0.190644 | 0.685109 | 0.583848 | 0.673687 |
| ABHD2 | 141.3453 | 144.4806 | 132.9189 | 135.0214 | 137.1708 | 124.7513 |
| ABHD6 | 8.375263 | 7.475426 | 8.120752 | 6.938222 | 5.656029 | 7.756055 |
| ABT1 | 51.96305 | 52.43791 | 52.86223 | 54.82809 | 52.40038 | 47.49782 |
| ACOT9 | 21.18468 | 17.18872 | 19.04587 | 22.40465 | 19.52388 | 21.59645 |
| ACSL6 | 95.67792 | 71.93192 | 130.033 | 83.25221 | 56.70005 | 88.60363 |
| ACSM3 | 1.951436 | 1.609049 | 2.535995 | 3.143499 | 2.23176 | 3.533812 |
| ACTN4 | 785.662 | 680.0171 | 751.5702 | 631.355 | 656.0571 | 613.207 |
| ADAM32 | 1.019961 | 1.362799 | 1.164748 | 0.935853 | 0.963714 | 1.209239 |
| ADAMTS10 | 2.840307 | 2.088722 | 3.286971 | 6.518702 | 5.400596 | 10.35209 |
| ADAMTSL3 | 1.210408 | 1.250668 | 1.250596 | 1.522859 | 0.942185 | 1.172703 |

In summary, Helios co-expression of either isoform with FOXP3 in CD4+ and CD8+ eTregs changed gene expression when compared to FOXP3 and this led to changes in gene enrichment of cellular pathways. Hel-Δ3B had more instances of increased enrichment of pathways than Hel-FL when co-expressed with FOXP3 in CD4+ and CD8+ eTregs. Additionally, there were differences in gene expression and pathway enrichment when directly comparing FOXP3+Hel-FL and FOXP3+Hel-Δ3B eTregs and some gene changes were different between CD4+ vs CD8+ eTregs from the same eTreg cell strain. Additionally, FOXP3+Hel-FL and FOXP3+Hel-Δ3B CD4+ and CD8+ eTregs had increased changes in Treg signature genes compared to FOXP3+ alone. Some of these genes were unique to either FOXP3+Hel-FL or FOXP3+Hel-Δ3B.

Discussion

Here we described a dual retroviral transduction system that was unexpectedly able to overexpress both FOXP3 and Helios in total human T cells and convert these T cells into CD4+ and CD8+ eTregs with immunosuppressive properties both in vitro and in vivo. Additionally, we are the first to describe differential roles for the two endogenous isoforms of Helios in mediating suppressive function in CD4+ and CD8+. Finally, we provided transcriptional profiling of human eTregs that expressed FOXP3+, FOXP3+Hel-FL, and FOXP3+Hel-Δ3B and compared these profiles to KEGG pathways and published Treg signatures. Together, these findings not only provide insight into the role of Helios and FOXP3 co-expression in Treg function but improve current human eTreg generation protocols and increase the potential for eTregs to be used in the clinic.

Helios has been described as a key Treg transcription factor for many years but its function in Tregs is still being defined. Experiments using Treg-specific Helios knock out mice have demonstrated that Helios plays a major role in mediating both CD4+ and CD8+ Treg function and survival. The Helios+ subset of human CD4+ Tregs have improved stability in pro-inflammatory environments compared to Helios-CD4+ Tregs. A subset of Helios+CD8+ Tregs have also been defined and have been shown to target T follicular helper cells. Our work demonstrated that co-expression of FOXP3 with Hel-FL in total human T cells was able to more effectively delay disease in a xenoGVHD model compared to FOXP3 alone. Both CD4+ and CD8+FOXP3+Hel-FL eTregs had the most suppressive capacity in vitro compared to FOXP3 alone. However, survival in vitro, Treg marker expression, and cytokine production were similar. There was a change in FOXP3+Hel-FL eTregs in expression of genes compared to FOXP3+ alone in immune pathways, such as cell adhesion molecules and JAK/STAT signaling, and Treg-related genes. This change in transcription was expected as ectopic expression of Helios and FOXP3 separately and together in mouse Tconvs mediated expression of different Treg signature genes. Further studies will be needed to investigate the roles of the genes altered by Hel-FL expression in Treg function.

An unexpected result was the differences between FOXP3+Hel-FL and FOXP3+Hel-Δ3B eTreg function. To the best of our knowledge, there have been no studies comparing the function of Hel-FL and Hel-Δ3B in primary human T cells. We demonstrated that FOXP3+ Hel-FL overexpression improves CD4+ eTreg suppressive activity, FOXP3+Hel-Δ3B overexpression does not. Interestingly, FOXP3+Hel-Δ3B does improve suppressive activity of CD8+ eTregs to a similar degree as FOXP3+Hel-FL eTregs. Both Hel-FL and Hel-Δ3B co-expression with FOXP3 changed gene expression when compared to FOXP3 alone and there were changes that were unique to each isoform of Helios.

Correlation of the gene changes in FOXP3+Hel-FL and FOXP3+ Hel-Δ3B with our functional studies could reveal more about the molecular mechanisms required to convey immunosuppressive properties to CD4+ and CD8+ T cells. For example, our RNASeq and GSEA data showed that FOXP3+Hel-FL CD4+ eTregs had increased gene enrichment in p53 signaling and cytokine-cytokine receptor interaction and decreased gene enrichment in cell adhesion molecules (CAMs) when compared to FOXP3+Hel-Δ3B CD4+ eTregs. p53 signaling is important for CD4+ Treg induction in mice. The different cytokine receptors that were upregulated on FOXP3+Hel-FL CD4+ eTregs were chemokine receptors such as CCR5 and CXCR6 which have been demonstrated to be expressed on endogenous human Tregs and these receptors drive immune cell trafficking to sites of inflammation. Finally, the only CAM that has been extensively studied in Treg function is ICAM-1 which is not differentially expressed in FOXP3-Hel-FL vs FOXP3-Hel-Δ3B CD4+ eTregs. The differences we observed in CAM expression between FOXP3+ Hel-FL and FOXP3+Hel-Δ3B CD4+ eTregs could be linked to T cell immunosuppressive function, though further studies are needed. Thus, the changes we found in these three KEGG pathways could explain why FOXP3+Hel-FL CD4+ eTregs were more effective at suppressing in vivo and in vitro than FOXP3+ Hel-Δ3B CD4+ eTregs.

The same three pathways were also changed in FOXP3+ Hel-Δ3B CD8+ compared to FOXP3+Hel-FL CD8+ eTregs but these two eTreg cell strains suppress equally well. Further examination revealed there were differences in the specific genes that were changed in these three pathways when comparing CD4+ and CD8+ FOXP3+Hel-Δ3B eTregs. Thus, the specific gene expression differences in these pathways that were unique to the CD4+ eTregs could identify the genes important in mediating T cell suppressive activity. Alternatively, CD8+ eTregs might not require these three pathways to suppress. Additionally, we found that both CD4+ and CD8+ FOXP3+Hel-Δ3B had a higher Treg signature compared to FOXP3+Hel-FL eTregs based on the number of genes that were differentially expressed in our Treg signature gene lists. However, based on the functional differences between FOXP3+Hel-FL and FOXP3+Hel-Δ3B CD4+ eTregs, it is likely the genes that are differentially expressed between these two eTreg cell strains that are critical to CD4+ T cell immunosuppressive function rather than the number of genes changed. Similarly, the gene expression differences between the FOXP3+Hel-FL and FOXP3+Hel-Δ3B CD8+ eTregs may not be critical to CD8+ T cell immunosuppression as these two cell strains suppress at a similar level.

These findings indicate that the endogenous isoforms of Helios play different roles in CD4+ vs CD8+ T cells. Hel-Δ3B lacks half an exon in a zinc finger domain, which would affect its ability to bind DNA. Thus, differences between the effect of FOXP3+Hel-Δ3B overexpression in CD4+ vs CD8+ T cells likely arises from epigenetic differences between the cell subsets and promoter accessibility. Another example of Ikaros family members playing different roles in CD4+ and CD8+ T cells is the critical role of Ikaros in CD8+ T cell development but not CD4+ development. Investigating the differences between FOXP3, FOXP3+Hel-FL and FOXP3+Hel-Δ3B CD4+ and CD8+ eTregs could help define which signaling pathways are critical for CD4+ and CD8+ Treg function. Further studies are required to elucidate the roles of these Helios splice variants in general T cell development and function.

Overall, we generated a novel protocol to genetically manipulate human T cells to express high levels of FOXP3 and Helios, which results in immunosuppressive CD4+ and CD8+ eTregs. FOXP3+ Hel-FL+ eTregs are more effective than FOXP3+ eTregs at suppressing both in vivo and in vitro and have changes in gene expression that affect immune pathway and Treg signature genes. We also discovered that Hel-FL and Hel-Δ3B affect CD4+ and CD8+ T cells differently when co-expressed with FOXP3. These new findings define new roles for endogenous Helios splice variants in both CD4+ and CD8+ Tregs and provide an improved human eTreg protocol that could be used to treat a variety inflammatory disease.

The invention claimed is:

1. A method of prophylactically and/or therapeutically treating a disease or condition in which it is desirable to suppress the immune system or reduce pro-inflammatory responses in a subject, said method comprising:
administering a composition comprising engineered human regulatory T cells (eTregs) to a subject in need thereof, said eTregs comprising ectopic overexpression of forkhead box P3 (FOXP3) and Ikaros transcription factor, wherein said eTregs comprise a first nucleic acid construct encoding said FOXP3 and a second separate nucleic acid construct encoding said Ikaros transcription factor.

2. The method of claim 1, wherein said composition comprises a therapeutically effective dosage of said eTregs suspended in a pharmaceutically acceptable medium or vehicle.

3. The method of claim 1, wherein said administrating reduces, mitigates, delays, inhibits, or alleviates one or more symptoms of the disease or condition in the subject.

4. The method of claim 1, wherein said eTregs maintain stable expression levels of FOXP3 for at least 12 days in vivo.

5. The method of claim 1, wherein said eTregs mediate suppression of T cell proliferation in said subject after said administering.

6. The method of claim 1, wherein the disease or condition is selected from the group consisting of diabetes, multiple sclerosis, graft vs. host disease (GVHD), allograft/transplant rejection, inflammatory bowel disease, lupus, rheumatoid arthritis, and other chronic inflammatory diseases.

7. The method of claim 1, wherein said method is used for treatment or inhibition of transplant rejection.

8. The method of claim 1, wherein said eTregs have expression levels of FOXP3 of at least 5 times that of natural Tregs.

9. The method of claim 1, wherein said Ikaros transcription factor is Helios.

10. The method of claim 9, wherein said composition comprises at least CD8+ Treg cells with ectopic overexpression of FOXP3 and Helios (CD8+FOXP3+Helios+eTregs).

11. The method of claim 9, wherein said composition comprises CD4+ Treg cells with ectopic overexpression of FOXP3 and Helios (CD4+FOXP3+Helios+eTregs).

12. The method of claim 9, wherein said eTregs comprise a mixture of CD8+ and CD4+ eTregs, each overexpressing FOXP3 and Helios.

13. The method of claim 9, wherein said eTregs have expression levels of Helios of at least 2 times that of natural Tregs.

14. The method of claim 1, wherein said eTregs further comprise at least one targeting moiety expressed on the surface of said eTreg.

15. The method of claim 1, further comprising preparing said eTregs prior to said administration, said preparing comprising:
collecting a biological sample from said subject, wherein said sample is peripheral blood, umbilical cord blood, lymph node, or thymus;
isolating mononuclear cells from said sample;
activating and expanding T cells from said mononuclear cells to yield a total T cell population;

first contacting said total T cell population with a first nucleic acid construct encoding Ikaros transcription factor and separating Ikaros transcription factor transduced T cells after said first contacting, second contacting said total T cell population with a second nucleic acid construct encoding FOXP3 and separating FOXP3 transduced T cells after said second contacting, wherein said first and second contacting steps are carried out sequentially in order or in reverse order, wherein said transduced cells are FOXP3+ and Ikaros transcription factor+ eTregs; and suspending said eTregs in a pharmaceutically acceptable medium or vehicle for administration to said subject.

16. The method of claim 15, wherein said Ikaros transcription factor is Helios, wherein said transduced cells are FOXP3+ and Helios+ eTregs.

* * * * *

SEQUENCE LISTING

<160> NUMBER OF SEQ ID NOS: 12

<210> SEQ ID NO 1
<211> LENGTH: 1578
<212> TYPE: DNA
<213> ORGANISM: Artificial Sequence
<220> FEATURE:
<223> OTHER INFORMATION: IKZF2 cDNA encoding full length Helios

<400> SEQUENCE: 1

```
atggaaacag aggctattga tggctatata acgtgtgaca atgagctttc acccgaaagg      60
gagcactcca atatggcaat tgacctcacc tcaagcacac ccaatggaca gcatgcctca     120
ccaagtcaca tgacaagcac aaattcagta aagctagaaa tgcagagtga tgaagagtgt     180
gacaggaaac ccctgagccg tgaagatgag atcaggggcc atgatgaggg tagcagccta     240
gaagaacccc taattgagag cagcgaggtg gctgacaaca ggaaagtcca ggagcttcaa     300
ggcgagggag gaatccggct tccgaatggt aaactgaaat gtgacgtctg tggcatggtt     360
tgcattgggc ccaatgtgct tatggtacat aaaaggagtc acactggtga acgcccttc      420 cactgtaacc agtgtggagc ttcttttact cagaagggca accttctgag acacataaag     480
ttacactctg gagagaagcc gttcaaatgt cctttctgta gctacgcctg tagaagaagg     540
gacgccctca caggacacct caggacccat tctgtgggta acctcacaa gtgcaactac      600 tgtggacgaa gctacaagca gcgcagttca ctggaggagc acaaggaacg ctgccacaac     660
tatctccaga atgtcagcat ggaggctgct gggcaggtca tgagtcacca tgtacctcct     720
atggaagatt gtaaggaaca agagcctatt atggacaaca atatttctct ggtgcctttt     780
gagagacctg ctgtcataga gaagctcacg gggaatatgg aaaacgtaa aagctccact      840 ccacaaaagt ttgtgggga aaagctcatg cgattcagct acccagatat tcactttgat      900
atgaacttaa catatgagaa ggaggctgag ctgatgcagt ctcatatgat ggaccaagcc     960
atcaacaatg caatcaccta ccttggagct gaggccttc accctctgat gcagcaccg     1020 ccaagcacaa tcgctgaagt ggcccccagtt ataagctcag cttattctca ggtctatcat    1080
ccaaatagga tagaaagacc cattagcagg gaaactgctg atagtcatga aacaacatg     1140 gatggcccca tctctctcat cagaccaaag agtcgacccc aggaaagaga ggcctctccc    1200
agcaatagct gcctggattc cactgactca gaaagcagcc atgatgacca ccagtcctac    1260
caaggacacc ctgccttaaa tcccaagagg aaacaaagcc cagcttacat gaaggaggat    1320
gtcaaagctt tggatactac caaggctcct aagggctctc tgaaggacat ctacaaggtc    1380
ttcaatggag aaggagaaca gattagggcc ttcaagtgtg agcactgccg agtcctttc     1440 ctagaccatg tcatgtacac cattcacatg ggttgccatg gctaccggga cccactggaa    1500
tgcaacatct gtggctacag aagccaggac cgttatgagt tttcatcaca cattgttcga    1560
ggggagcaca cattccac                                                  1578
```

<210> SEQ ID NO 2
<211> LENGTH: 526
<212> TYPE: PRT
<213> ORGANISM: Homo sapiens
<220> FEATURE:
<221> NAME/KEY: MISC_FEATURE
<222> LOCATION: (1)..(526)
<223> OTHER INFORMATION: Helios full length isoform

<400> SEQUENCE: 2

```
Met Glu Thr Glu Ala Ile Asp Gly Tyr Ile Thr Cys Asp Asn Glu Leu
1               5                   10                  15

Ser Pro Glu Arg Glu His Ser Asn Met Ala Ile Asp Leu Thr Ser Ser
            20                  25                  30

Thr Pro Asn Gly Gln His Ala Ser Pro Ser His Met Thr Ser Thr Asn
        35                  40                  45

Ser Val Lys Leu Glu Met Gln Ser Asp Glu Cys Asp Arg Lys Pro
50                  55                  60

Leu Ser Arg Glu Asp Glu Ile Arg Gly His Asp Glu Gly Ser Ser Leu
65                  70                  75                  80

Glu Glu Pro Leu Ile Glu Ser Ser Val Ala Asp Asn Arg Lys Val
                85                  90                  95

Gln Glu Leu Gln Gly Glu Gly Gly Ile Arg Leu Pro Asn Gly Lys Leu
                100                 105                 110

Lys Cys Asp Val Cys Gly Met Val Cys Ile Gly Pro Asn Val Leu Met
            115                 120                 125

Val His Lys Arg Ser His Thr Gly Glu Arg Pro Phe His Cys Asn Gln
130                 135                 140

Cys Gly Ala Ser Phe Thr Gln Lys Gly Asn Leu Leu Arg His Ile Lys
145                 150                 155                 160

Leu His Ser Gly Glu Lys Pro Phe Lys Cys Pro Phe Cys Ser Tyr Ala
                165                 170                 175

Cys Arg Arg Arg Asp Ala Leu Thr Gly His Leu Arg Thr His Ser Val
                180                 185                 190

Gly Lys Pro His Lys Cys Asn Tyr Cys Gly Arg Ser Tyr Lys Gln Arg
                195                 200                 205

Ser Ser Leu Glu Glu His Lys Glu Arg Cys His Asn Tyr Leu Gln Asn
            210                 215                 220

Val Ser Met Glu Ala Ala Gly Gln Val Met Ser His His Val Pro Pro
225                 230                 235                 240

Met Glu Asp Cys Lys Glu Gln Glu Pro Ile Met Asp Asn Asn Ile Ser
                245                 250                 255

Leu Val Pro Phe Glu Arg Pro Ala Val Ile Glu Lys Leu Thr Gly Asn
                260                 265                 270

Met Gly Lys Arg Lys Ser Ser Thr Pro Gln Lys Phe Val Gly Glu Lys
                275                 280                 285

Leu Met Arg Phe Ser Tyr Pro Asp Ile His Phe Asp Met Asn Leu Thr
290                 295                 300

Tyr Glu Lys Glu Ala Glu Leu Met Gln Ser His Met Met Asp Gln Ala
305                 310                 315                 320

Ile Asn Asn Ala Ile Thr Tyr Leu Gly Ala Glu Ala Leu His Pro Leu
                325                 330                 335

Met Gln His Pro Pro Ser Thr Ile Ala Glu Val Ala Pro Val Ile Ser
            340                 345                 350

Ser Ala Tyr Ser Gln Val Tyr His Pro Asn Arg Ile Glu Arg Pro Ile
                355                 360                 365

Ser Arg Glu Thr Ala Asp Ser His Glu Asn Asn Met Asp Gly Pro Ile
            370                 375                 380

Ser Leu Ile Arg Pro Lys Ser Arg Pro Gln Glu Arg Glu Ala Ser Pro
385                 390                 395                 400
```

```
Ser Asn Ser Cys Leu Asp Ser Thr Asp Ser Glu Ser Ser His Asp Asp
            405                 410                 415

His Gln Ser Tyr Gln Gly His Pro Ala Leu Asn Pro Lys Arg Lys Gln
        420                 425                 430

Ser Pro Ala Tyr Met Lys Glu Asp Val Lys Ala Leu Asp Thr Thr Lys
    435                 440                 445

Ala Pro Lys Gly Ser Leu Lys Asp Ile Tyr Lys Val Phe Asn Gly Glu
450                 455                 460

Gly Glu Gln Ile Arg Ala Phe Lys Cys Glu His Cys Arg Val Leu Phe
465                 470                 475                 480

Leu Asp His Val Met Tyr Thr Ile His Met Gly Cys His Gly Tyr Arg
                485                 490                 495

Asp Pro Leu Glu Cys Asn Ile Cys Gly Tyr Arg Ser Gln Asp Arg Tyr
            500                 505                 510

Glu Phe Ser Ser His Ile Val Arg Gly Glu His Thr Phe His
            515                 520                 525
```

```
<210> SEQ ID NO 3
<211> LENGTH: 1287
<212> TYPE: DNA
<213> ORGANISM: Artificial Sequence
<220> FEATURE:
<223> OTHER INFORMATION: FOXP3 codon optimized cDNA

<400> SEQUENCE: 3
aaccccagac ccggaaagcc ttctgcccct tctctggccc tgggaccttc tcctggcgcc      60
tccccatctt ggagagccgc ccctaaagcc agcgatctgc tgggagctag aggccctggc     120
ggcacatttc agggcaggga tctgagaggc ggagcccacg cttctagcag cagcctgaac     180
cccatgcccc ctagccagct gcagctgcct acactgcctc tcgtgatggt ggcccctagc     240
ggagctagac tgggccctct gcctcatctg caggccctgc tgcaggacag acccacttc      300 atgcaccagc tgagcaccgt ggatgcccac gccagaacac ctgtgctgca ggtgcacccc     360
ctggaaagcc ctgccatgat cagcctgacc ccccctacaa ccgctaccgg cgtgttcagc     420
ctgaaggcca gacctggact gccccctggc atcaatgtgg ccagcctgga atgggtgtcc     480
cgcgaacctg ccctgctgtg caccttcccc aatcccagcg cccccagaaa ggacagcaca     540
ctgtctgccg tgccccagag cagctatccc tgctggccta acggcgtgtg caagtggcct     600
ggctgcgaga aggtgttcga ggaacccgag acttcctga gcactgccaa ggccgaccat      660
ctgctggacg agaaaggcag agcccagtgt ctgctgcagc gcgagatggt gcagagcctg     720
gaacagcagc tggtgctgga aaagaaaag ctgagcgcca tgcaggccca cctggctgga     780
aagatggccc tgacaaaggc cagcagcgtg gccagctctg acaagggcag ctgctgcatt     840
gtggccgctg gctctcaggg acctgtggtg cctgcttgga gcggacctag agaggccccc     900
gatagcctgt tgccgtgcg agacacctg tgggcagcc acggcaactc taccttcccc       960
gagttcctgc acaacatgga ctacttcaag ttccacaaca tgaggccccc cttcacctac    1020
gccaccctga tcagatgggc cattctggaa gccccgaga agcagcggac cctgaacgaa     1080
atctaccact ggtttacccg gatgttcgcc ttcttcagaa accaccccgc cacctggaag    1140
aacgccatcc ggcacaatct gagcctgcac aagtgcttcg tgcgggtgga aagcgagaag    1200
ggcgccgtgt ggacagtgga cgagctggaa tttcggaaga gcggtcccca gaggcccagc    1260
cggtgtagca atcctacacc tggacct                                        1287
```

```
<210> SEQ ID NO 4
<211> LENGTH: 429
<212> TYPE: PRT
<213> ORGANISM: Artificial Sequence
<220> FEATURE:
<223> OTHER INFORMATION: FOXP3 codon optimized protein sequence

<400> SEQUENCE: 4

Asn Pro Arg Pro Gly Lys Pro Ser Ala Pro Ser Leu Ala Leu Gly Pro
1               5                   10                  15

Ser Pro Gly Ala Ser Pro Ser Trp Arg Ala Ala Pro Lys Ala Ser Asp
                20                  25                  30

Leu Leu Gly Ala Arg Gly Pro Gly Gly Thr Phe Gln Gly Arg Asp Leu
            35                  40                  45

Arg Gly Gly Ala His Ala Ser Ser Ser Leu Asn Pro Met Pro Pro
        50                  55                  60

Ser Gln Leu Gln Leu Pro Thr Leu Pro Leu Val Met Val Ala Pro Ser
65                  70                  75                  80

Gly Ala Arg Leu Gly Pro Leu Pro His Leu Gln Ala Leu Leu Gln Asp
                85                  90                  95

Arg Pro His Phe Met His Gln Leu Ser Thr Val Asp Ala His Ala Arg
            100                 105                 110

Thr Pro Val Leu Gln Val His Pro Leu Glu Ser Pro Ala Met Ile Ser
        115                 120                 125

Leu Thr Pro Pro Thr Thr Ala Thr Gly Val Phe Ser Leu Lys Ala Arg
130                 135                 140

Pro Gly Leu Pro Pro Gly Ile Asn Val Ala Ser Leu Glu Trp Val Ser
145                 150                 155                 160

Arg Glu Pro Ala Leu Leu Cys Thr Phe Pro Asn Pro Ser Ala Pro Arg
                165                 170                 175

Lys Asp Ser Thr Leu Ser Ala Val Pro Gln Ser Ser Tyr Pro Leu Leu
            180                 185                 190

Ala Asn Gly Val Cys Lys Trp Pro Gly Cys Glu Lys Val Phe Glu Glu
        195                 200                 205

Pro Glu Asp Phe Leu Lys His Cys Gln Ala Asp His Leu Leu Asp Glu
    210                 215                 220

Lys Gly Arg Ala Gln Cys Leu Leu Gln Arg Glu Met Val Gln Ser Leu
225                 230                 235                 240

Glu Gln Gln Leu Val Leu Glu Lys Glu Lys Leu Ser Ala Met Gln Ala
                245                 250                 255

His Leu Ala Gly Lys Met Ala Leu Thr Lys Ala Ser Ser Val Ala Ser
            260                 265                 270

Ser Asp Lys Gly Ser Cys Cys Ile Val Ala Ala Gly Ser Gln Gly Pro
        275                 280                 285

Val Val Pro Ala Trp Ser Gly Pro Arg Glu Ala Pro Asp Ser Leu Phe
    290                 295                 300

Ala Val Arg Arg His Leu Trp Gly Ser His Gly Asn Ser Thr Phe Pro
305                 310                 315                 320

Glu Phe Leu His Asn Met Asp Tyr Phe Lys Phe His Asn Met Arg Pro
                325                 330                 335

Pro Phe Thr Tyr Ala Thr Leu Ile Arg Trp Ala Ile Leu Glu Ala Pro
            340                 345                 350

Glu Lys Gln Arg Thr Leu Asn Glu Ile Tyr His Trp Phe Thr Arg Met
        355                 360                 365
```

```
Phe Ala Phe Arg Asn His Pro Ala Thr Trp Lys Asn Ala Ile Arg
370                 375                 380

His Asn Leu Ser Leu His Lys Cys Phe Val Arg Val Glu Ser Glu Lys
385                 390                 395                 400

Gly Ala Val Trp Thr Val Asp Glu Leu Glu Phe Arg Lys Lys Arg Ser
                405                 410                 415

Gln Arg Pro Ser Arg Cys Ser Asn Pro Thr Pro Gly Pro
                420                 425
```

```
<210> SEQ ID NO 5
<211> LENGTH: 1500
<212> TYPE: DNA
<213> ORGANISM: Artificial Sequence
<220> FEATURE:
<223> OTHER INFORMATION: IKZF2 cDNA encoding shortened Helios isoform

<400> SEQUENCE: 5
atggaaacag aggctattga tggctatata acgtgtgaca atgagctttc acccgaaagg     60
gagcactcca atatggcaat tgacctcacc tcaagcacac ccaatggaca gcatgcctca    120
ccaagtcaca tgacaagcac aaattcagta aagctagaaa tgcagagtga tgaagagtgt    180
gacaggaaac ccctgagccg tgaagatgag atcaggggcc atgatgaggg tagcagccta    240
gaagaacccc taattgagag cagcgaggtg gctgacaaca ggaaagtcca ggagcttcaa    300
ggcgagggag gaatccggct tccgaatggt gaacgcccct ccactgtaa ccagtgtgga    360 gcttctttta ctcagaaggg caaccttctg agacacataa agttacactc tggagagaag    420
ccgttcaaat gtccttctg tagctacgcc tgtagaagaa gggacgccct cacaggacac    480
ctcaggaccc attctgtggg taaacctcac aagtgcaact actgtggacg aagctacaag    540
cagcgcagtt cactggagga gcacaaggaa cgctgccaca actatctcca gaatgtcagc    600
atggaggctg ctgggcaggt catgagtcac catgtacctc ctatggaaga ttgtaaggaa    660
caagagccta ttatggacaa caatatttct ctggtgcctt ttgagagacc tgctgtcata    720
gagaagctca cggggaatat gggaaaacgt aaaagctcca ctccacaaaa gtttgtgggg    780
gaaaagctca tgcgattcag ctacccagat attcactttg atatgaactt aacatatgag    840
aaggaggctg agctgatgca gtctcatatg atggaccaag ccatcaacaa tgcaatcacc    900
taccttggag ctgaggccct tcaccctctg atgcagcacc cgccaagcac aatcgctgaa    960
gtggccccag ttataagctc agcttattct caggtctatc atccaaatag gatagaaaga   1020
cccattagca gggaaactgc tgatagtcat gaaaacaaca tggatggccc catctctctc   1080
atcagaccaa agagtcgacc ccaggaaaga gaggcctctc cagcaatag ctgcctggat   1140 tccactgact cagaaagcag ccatgatgac caccagtcct accaaggaca ccctgcctta   1200
aatcccaaga ggaaacaaag cccagcttac atgaaggagg atgtcaaagc tttggatact   1260
accaaggctc ctaagggctc tctgaaggac atctacaagg tcttcaatgg agaaggagaa   1320
cagattaggg ccttcaagtg tgagcactgc cgagtcctt tcctagacca tgtcatgtac   1380
accattcaca tgggttgcca tggctaccgg gacccactgg aatgcaacat ctgtggctac   1440
agaagccagg accgttatga gttttcatca cacattgttc gagggagca cacattccac   1500
```

```
<210> SEQ ID NO 6
<211> LENGTH: 500
<212> TYPE: PRT
<213> ORGANISM: Homo sapiens
<220> FEATURE:
<221> NAME/KEY: MISC_FEATURE
```

<222> LOCATION: (1)..(500)
<223> OTHER INFORMATION: Helios shortened isoform

<400> SEQUENCE: 6

```
Met Glu Thr Glu Ala Ile Asp Gly Tyr Ile Thr Cys Asp Asn Glu Leu
1               5                   10                  15

Ser Pro Glu Arg Glu His Ser Asn Met Ala Ile Asp Leu Thr Ser Ser
            20                  25                  30

Thr Pro Asn Gly Gln His Ala Ser Pro Ser His Met Thr Ser Thr Asn
        35                  40                  45

Ser Val Lys Leu Glu Met Gln Ser Asp Glu Cys Asp Arg Lys Pro
    50                  55                  60

Leu Ser Arg Glu Asp Glu Ile Arg Gly His Asp Gly Ser Ser Leu
65                  70                  75                  80

Glu Glu Pro Leu Ile Glu Ser Ser Glu Val Ala Asp Asn Arg Lys Val
                85                  90                  95

Gln Glu Leu Gln Gly Glu Gly Gly Ile Arg Leu Pro Asn Gly Glu Arg
            100                 105                 110

Pro Phe His Cys Asn Gln Cys Gly Ala Ser Phe Thr Gln Lys Gly Asn
        115                 120                 125

Leu Leu Arg His Ile Lys Leu His Ser Gly Glu Lys Pro Phe Lys Cys
130                 135                 140

Pro Phe Cys Ser Tyr Ala Cys Arg Arg Arg Asp Ala Leu Thr Gly His
145                 150                 155                 160

Leu Arg Thr His Ser Val Gly Lys Pro His Lys Cys Asn Tyr Cys Gly
                165                 170                 175

Arg Ser Tyr Lys Gln Arg Ser Ser Leu Glu Glu His Lys Glu Arg Cys
            180                 185                 190

His Asn Tyr Leu Gln Asn Val Ser Met Glu Ala Ala Gly Gln Val Met
        195                 200                 205

Ser His His Val Pro Pro Met Glu Asp Cys Lys Glu Gln Glu Pro Ile
210                 215                 220

Met Asp Asn Asn Ile Ser Leu Val Pro Phe Glu Arg Pro Ala Val Ile
225                 230                 235                 240

Glu Lys Leu Thr Gly Asn Met Gly Lys Arg Lys Ser Ser Thr Pro Gln
                245                 250                 255

Lys Phe Val Gly Glu Lys Leu Met Arg Phe Ser Tyr Pro Asp Ile His
            260                 265                 270

Phe Asp Met Asn Leu Thr Tyr Glu Lys Glu Ala Glu Leu Met Gln Ser
        275                 280                 285

His Met Met Asp Gln Ala Ile Asn Asn Ala Ile Thr Tyr Leu Gly Ala
290                 295                 300

Glu Ala Leu His Pro Leu Met Gln His Pro Pro Ser Thr Ile Ala Glu
305                 310                 315                 320

Val Ala Pro Val Ile Ser Ser Ala Tyr Ser Gln Val Tyr His Pro Asn
                325                 330                 335

Arg Ile Glu Arg Pro Ile Ser Arg Glu Thr Ala Asp Ser His Glu Asn
            340                 345                 350

Asn Met Asp Gly Pro Ile Ser Leu Ile Arg Pro Lys Ser Arg Pro Gln
        355                 360                 365

Glu Arg Glu Ala Ser Pro Ser Asn Ser Cys Leu Asp Ser Thr Asp Ser
370                 375                 380

Glu Ser Ser His Asp Asp His Gln Ser Tyr Gln Gly Pro Ala Leu
385                 390                 395                 400
```

```
Asn Pro Lys Arg Lys Gln Ser Pro Ala Tyr Met Lys Glu Asp Val Lys
            405                 410                 415

Ala Leu Asp Thr Thr Lys Ala Pro Lys Gly Ser Leu Lys Asp Ile Tyr
        420                 425                 430

Lys Val Phe Asn Gly Glu Gly Glu Gln Ile Arg Ala Phe Lys Cys Glu
    435                 440                 445

His Cys Arg Val Leu Phe Leu Asp His Val Met Tyr Thr Ile His Met
450                 455                 460

Gly Cys His Gly Tyr Arg Asp Pro Leu Glu Cys Asn Ile Cys Gly Tyr
465                 470                 475                 480

Arg Ser Gln Asp Arg Tyr Glu Phe Ser Ser His Ile Val Arg Gly Glu
                485                 490                 495

His Thr Phe His
            500

<210> SEQ ID NO 7
<211> LENGTH: 24
<212> TYPE: DNA
<213> ORGANISM: Artificial Sequence
<220> FEATURE:
<223> OTHER INFORMATION: Forward primer

<400> SEQUENCE: 7
tgatggctat ataacgtgtg acaa                                          24

<210> SEQ ID NO 8
<211> LENGTH: 22
<212> TYPE: DNA
<213> ORGANISM: Artificial Sequence
<220> FEATURE:
<223> OTHER INFORMATION: Reverse primer

<400> SEQUENCE: 8
ctcacacttg aaggccctaa tc                                            22

<210> SEQ ID NO 9
<211> LENGTH: 993
<212> TYPE: DNA
<213> ORGANISM: Artificial Sequence
<220> FEATURE:
<223> OTHER INFORMATION: codon optimized delta-CD19

<400> SEQUENCE: 9 cccctcggc tgctgttctt cctgctgttc ctgaccccta tggaagtgcg gcccgaggaa     60 ccctggtcg tgaaagtgga gagggcgac aacgccgtgc tgcagtgtct gaagggcacc    120
tccgatggcc ctacccagca gctgacatgg tccagagaga gccccctgaa gcccttcctg    180
aagctgagcc tgggactgcc tggcctgggc atccatatga ggccactggc catctggctg    240
ttcatcttca cgtgtccca gcagatgggc ggcttctacc tgtgtcagcc tggcccccca    300
agcgagaaag cctggcagcc tggctggacc gtgaacgtgg aaggatctgg cgagctgttc    360
cggtggaacg tgtccgatct gggcggactg ggctgcggcc tgaagaacag aagcagcgag    420
ggccctagca gccccagcgg caaactgatg agccccaagc tgtacgtgtg gcccaaggac    480
cggcccgaga tttgggaagg cgagcctcct tgcctgcccc ccagagacag cctgaatcag    540
agcctgagcc aggacctgac aatgccccct ggcagcacac tgtggctgag ctgtggcgtg    600
ccacccgact ctgtgtccag aggccctctg agctggaccc acgtgcaccc taagggccct    660
aagagcctgc tgtccctgga actgaaggac gacagacccg ccagagatat gtgggtcatg    720
```

```
gaaaccggcc tgctgctgcc tagagccacc gctcaggatg ccggaaagta ctactgccac    780
cggggcaacc tgaccatgag cttccacctg gaaatcaccg ccagaccgt gctgtggcac    840 tggctgctga aaccggcgg atggaaagtg tccgccgtga ccctggccta cctgatcttc    900
tgcctgtgct ccctcgtggg catcctgcat ctgcagcggg ctctggtgct gcggcggaag    960
agaaagagaa tgaccgaccc cacccgcaga ttc                                993
```

<210> SEQ ID NO 10
<211> LENGTH: 331
<212> TYPE: PRT
<213> ORGANISM: Artificial Sequence
<220> FEATURE:
<223> OTHER INFORMATION: truncated delta-CD19

<400> SEQUENCE: 10

```
Pro Pro Arg Leu Leu Phe Phe Leu Leu Phe Leu Thr Pro Met Glu Val
1               5                   10                  15

Arg Pro Glu Glu Pro Leu Val Val Lys Val Glu Glu Gly Asp Asn Ala
                20                  25                  30

Val Leu Gln Cys Leu Lys Gly Thr Ser Asp Gly Pro Thr Gln Gln Leu
            35                  40                  45

Thr Trp Ser Arg Glu Ser Pro Leu Lys Pro Phe Leu Lys Leu Ser Leu
        50                  55                  60

Gly Leu Pro Gly Leu Gly Ile His Met Arg Pro Leu Ala Ile Trp Leu
65                  70                  75                  80

Phe Ile Phe Asn Val Ser Gln Gln Met Gly Gly Phe Tyr Leu Cys Gln
                85                  90                  95

Pro Gly Pro Pro Ser Glu Lys Ala Trp Gln Pro Gly Trp Thr Val Asn
            100                 105                 110

Val Glu Gly Ser Gly Glu Leu Phe Arg Trp Asn Val Ser Asp Leu Gly
        115                 120                 125

Gly Leu Gly Cys Gly Leu Lys Asn Arg Ser Ser Glu Gly Pro Ser Ser
130                 135                 140

Pro Ser Gly Lys Leu Met Ser Pro Lys Leu Tyr Val Trp Ala Lys Asp
145                 150                 155                 160

Arg Pro Glu Ile Trp Glu Gly Glu Pro Pro Cys Leu Pro Pro Arg Asp
                165                 170                 175

Ser Leu Asn Gln Ser Leu Ser Gln Asp Leu Thr Met Ala Pro Gly Ser
            180                 185                 190

Thr Leu Trp Leu Ser Cys Gly Val Pro Pro Asp Ser Val Ser Arg Gly
        195                 200                 205

Pro Leu Ser Trp Thr His Val His Pro Lys Gly Pro Lys Ser Leu Leu
210                 215                 220

Ser Leu Glu Leu Lys Asp Asp Arg Pro Ala Arg Asp Met Trp Val Met
225                 230                 235                 240

Glu Thr Gly Leu Leu Leu Pro Arg Ala Thr Ala Gln Asp Ala Gly Lys
                245                 250                 255

Tyr Tyr Cys His Arg Gly Asn Leu Thr Met Ser Phe His Leu Glu Ile
            260                 265                 270

Thr Ala Arg Pro Val Leu Trp His Trp Leu Leu Arg Thr Gly Gly Trp
        275                 280                 285

Lys Val Ser Ala Val Thr Leu Ala Tyr Leu Ile Phe Cys Leu Cys Ser
290                 295                 300
```

Leu Val Gly Ile Leu His Leu Gln Arg Ala Leu Val Leu Arg Arg Lys
305                 310                 315                 320

Arg Lys Arg Met Thr Asp Pro Thr Arg Arg Phe
                325                 330

<210> SEQ ID NO 11
<211> LENGTH: 945
<212> TYPE: DNA
<213> ORGANISM: Artificial Sequence
<220> FEATURE:
<223> OTHER INFORMATION: codon optimized delta-CD34

<400> SEQUENCE: 11

| | | | | | |
|---|---|---|---|---|---|
| ctcgttagaa | gaggcgctag | agctggcccc | agaatgccta | gaggatggac | agctctgtgc | 60 |
| ctgctgagcc | tgctgcctag | cggctttatg | agcctggaca | caacggcac | cgccacacct | 120 |
| gaactgccta | cacagggcac | cttcagcaat | gtgtctacca | acgtgtccta | ccaagagaca | 180 |
| accacaccta | gcacactggg | cagcacatct | ctgcaccctg | tgtctcagca | cggcaatgag | 240 |
| gccaccacca | acatcaccga | gacaaccgtg | aagttcacct | ctacctccgt | gattaccagc | 300 |
| gtgtacggca | acaccaacag | cagcgtgcag | agccagacaa | gcgtgatcag | caccgtgttc | 360 |
| acaacccctg | ccaatgtgtc | cacaccagaa | accacactga | gcccagcct | gtctcctgga | 420 |
| aacgtgtccg | atctgagcac | cacctctaca | agcctggcca | cctctcctac | aaagccctac | 480 |
| acaagcagca | gccccatcct | gagcgatatc | aaggccgaga | tcaagtgcag | cggcatccgg | 540 |
| gaagtgaagc | tgacccaggg | catctgcctg | aacagaaca | agaccagcag | ctgcgccgag | 600 |
| ttcaagaagg | acagaggcga | aggactggcc | agagtgctgt | gtggcgaaga | acaggccgat | 660 |
| gctgatgctg | cgctcaagt | gtgctctctg | ctgctggctc | agtctgaagt | gcggcctcag | 720 |
| tgtctgttgc | tggtgctggc | caacagaacc | gagatcagca | gcaaactgca | gctgatgaag | 780 |
| aagcaccaga | gcgacctgaa | gaagctgggc | atcctggact | tcaccgagca | ggatgtggcc | 840 |
| tctcaccaga | gctacagcca | gaaaaccctg | atcgccctgg | tcacatctgg | cgctctgctg | 900 |
| gctgtgctgg | gaatcaccgg | ctactttctg | atgaatcgga | gattc | | 945 |

<210> SEQ ID NO 12
<211> LENGTH: 315
<212> TYPE: PRT
<213> ORGANISM: Artificial Sequence
<220> FEATURE:
<223> OTHER INFORMATION: truncated delta-CD34

<400> SEQUENCE: 12

Leu Val Arg Arg Gly Ala Arg Ala Gly Pro Arg Met Pro Arg Gly Trp
1               5                   10                  15

Thr Ala Leu Cys Leu Leu Ser Leu Leu Pro Ser Gly Phe Met Ser Leu
                20                  25                  30

Asp Asn Asn Gly Thr Ala Thr Pro Glu Leu Pro Thr Gln Gly Thr Phe
            35                  40                  45

Ser Asn Val Ser Thr Asn Val Ser Tyr Gln Glu Thr Thr Thr Pro Ser
        50                  55                  60

Thr Leu Gly Ser Thr Ser Leu His Pro Val Ser Gln His Gly Asn Glu
65                  70                  75                  80

Ala Thr Thr Asn Ile Thr Glu Thr Thr Val Lys Phe Thr Ser Thr Ser
                85                  90                  95

Val Ile Thr Ser Val Tyr Gly Asn Thr Asn Ser Ser Val Gln Ser Gln
            100                 105                 110

-continued

```
Thr Ser Val Ile Ser Thr Val Phe Thr Thr Pro Ala Asn Val Ser Thr
        115                 120             125
Pro Glu Thr Thr Leu Lys Pro Ser Leu Ser Pro Gly Asn Val Ser Asp
    130                 135             140
Leu Ser Thr Thr Ser Thr Ser Leu Ala Thr Ser Pro Thr Lys Pro Tyr
145                 150                 155                 160
Thr Ser Ser Ser Pro Ile Leu Ser Asp Ile Lys Ala Glu Ile Lys Cys
                165                 170                 175
Ser Gly Ile Arg Glu Val Lys Leu Thr Gln Gly Ile Cys Leu Glu Gln
            180                 185                 190
Asn Lys Thr Ser Ser Cys Ala Glu Phe Lys Lys Asp Arg Gly Glu Gly
        195                 200                 205
Leu Ala Arg Val Leu Cys Gly Glu Glu Gln Ala Asp Ala Asp Ala Gly
        210                 215                 220
Ala Gln Val Cys Ser Leu Leu Leu Ala Gln Ser Glu Val Arg Pro Gln
225                 230                 235                 240
Cys Leu Leu Leu Val Leu Ala Asn Arg Thr Glu Ile Ser Ser Lys Leu
                245                 250                 255
Gln Leu Met Lys Lys His Gln Ser Asp Leu Lys Lys Leu Gly Ile Leu
            260                 265                 270
Asp Phe Thr Glu Gln Asp Val Ala Ser His Gln Ser Tyr Ser Gln Lys
        275                 280                 285
Thr Leu Ile Ala Leu Val Thr Ser Gly Ala Leu Leu Ala Val Leu Gly
        290                 295                 300
Ile Thr Gly Tyr Phe Leu Met Asn Arg Arg Phe
305                 310                 315
```